(12) United States Patent
Henrich et al.

(10) Patent No.: US 8,288,549 B2
(45) Date of Patent: Oct. 16, 2012

(54) GLYCINE B ANTAGONIST

(75) Inventors: Markus Henrich, Munzenberg (DE);
Angela Bauer, Mainz (DE); Jens Nagel, Blankensee (DE); Meik Sladek, Bad Soden-Salmünster (DE); Christopher Graham Raphael Parsons, Nidderau (DE); Wojciech Danysz, Nidderau (DE); Valerjans Kauss, Rigariga (LV); Jevgenijs Rozhkovs, Riga (LV); Igors Starchenkovs, Riga (LV); Dina Trifanova, Riga (LV)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 12/998,246

(22) PCT Filed: Sep. 30, 2009

(86) PCT No.: PCT/EP2009/007022
§ 371 (c)(1),
(2), (4) Date: Mar. 29, 2011

(87) PCT Pub. No.: WO2010/037533
PCT Pub. Date: Apr. 8, 2010

(65) Prior Publication Data
US 2011/0190342 A1    Aug. 4, 2011

Related U.S. Application Data

(60) Provisional application No. 61/194,722, filed on Sep. 30, 2008.

(30) Foreign Application Priority Data

Sep. 30, 2008   (EP) ..................................... 08253183

(51) Int. Cl.
C07D 215/54   (2006.01)
C07D 401/12   (2006.01)
C07D 409/12   (2006.01)
C07D 409/14   (2006.01)

(52) U.S. Cl. ......................... 546/156; 546/159; 546/162

(58) Field of Classification Search .................... None
See application file for complete search history.

(56) References Cited

U.S. PATENT DOCUMENTS

2005/0026915 A1   2/2005 DeVita et al.
2006/0103058 A1   5/2006 Wada et al.

OTHER PUBLICATIONS

Vippagunta et al., "Crystalline Solids", 48 Adv. Drug Delivery Rev. 3-26 (2001).*
Rautio et al., Prodrugs: Design and Clinical Applications, 7 Nat. Rev. Drug Dis. 255-70 (2008).*
D. Catarzi, et al., "Competitive gly/NMDA receptor antagonists" Current Topics in Medicinal Chemistry, vol. 6, p. 809-821, 2006.
International Search Report and Written Opinion for PCT/EP2009/007022 of Oct. 23, 2009.
Ornstein, P. L. et al., "Structure-Activity studies of 6-substituted decahydroisoquinoline-3-carboxylic acid AMPA receptor antagonists" Journal of Medicinal Chemistry, vol. 39, No. 11, p. 2232-2244, May 24, 1996.

* cited by examiner

*Primary Examiner* — Janet Andres
*Assistant Examiner* — Timothy R Rozof
(74) *Attorney, Agent, or Firm* — Hueschen and Sage

(57) ABSTRACT

The invention relates to quinoline derivatives as well as their pharmaceutically acceptable salts. The invention further relates to a process for the preparation of such compounds. The compounds of the invention are glycine B antagonists and are therefore useful for the control and prevention of various disorders, including neurological disorders.

12 Claims, No Drawings

GLYCINE B ANTAGONIST

FIELD OF THE INVENTION

The present invention relates to novel quinoline derivatives which may act as glycine B antagonists, methods for their synthesis and the treatment and/or prevention of various diseases and disorders, including neurological disorders, by administration of such substances.

BACKGROUND OF THE INVENTION

Glutamate is a major excitatory transmitter in the central nervous system and is believed to be involved in many pathological and excitotoxic processes; therefore, there is a great deal of interest in the development of glutamate antagonists for therapeutic uses. Glutamate activates three major types of ionotropic receptors: α-amino-3-hydroxy-5-methyl-4-isoazolepropionic acid (AMPA), kainate, and N-methyl-D-aspartate (NMDA) as well as several types of metabotropic receptors. Antagonism of NMDA receptors potentially has a wide range of therapeutic applications. Functional inhibition of NMDA receptors may be achieved through actions at different recognition sites, such as the primary transmitter site, the strychnine insensitive glycine site (glycine B), the polyamine site, and the phencyclidine site located inside the cation channel.

Receptor desensitization may represent a physiological process serving as an endogenous control mechanism to prevent long term neurotoxic activation of glutamate receptors but allow their transient physiological activation. In the case of the NMDA receptor, the co-agonist glycine is an endogenous ligand inhibiting such desensitization via activation of the glycine B site. It is noteworthy that ischemia increases not only the concentration of extracellular glutamate but also that of glycine and, although this latter effect is less pronounced, it actually persists for a longer period of time. Thus, glycine B antagonists may restore normal synaptic transmission under such conditions by increasing NMDA receptor desensitization to its physiological level. It has been suggested that glycine B antagonists may offer a better therapeutic window than agents acting at other recognition sites of the NMDA receptor complex.

Therefore, glycine B antagonists, such as glycine B antagonists restricted to action in the peripheral nervous system (PNS), may be useful for the treatment and/or prevention of pain, including acute pain, chronic pain, allodynia, hyperalgesia, visceral pain, phantom pain, post-operative pain, neuropathic pain, peripheral neuropathy including, for example peripheral neuropathy induced by nociception, inflammation, ischemia, viral infection (HZV), traumatic and other mechanical nerve injury, cancer, diabetes mellitus, HIV infection, fibromyalgia, trigeminus neuralgia, inflammatory bowel diseases (IBD), irritative bowel syndrome (IBS), arthritis including rheumatoid arthritis, osteoarthritis (degenerative joint disease), multiple sclerosis (MS) and gout (metabolic arthritis).

Glycine B antagonists may also be useful for the treatment and/or prevention of acute insults, including cerebral ischemia, cerebral infarct, brain oedema, anoxia, inner ear insult, inner ear insult in tinnitus, head or brain or spinal cord trauma, head or brain or spinal cord injuries, trauma, sound- or drug-induced inner ear insult, ischaemia resulting from cardiac arrest or stroke or bypass operations or transplants, acute pain, hypoxia, perinatal hypoxia, and ischaemia;

chronic insults, such as neurodegenerative disorders, including Morbus Huntington, Alzheimer's disease Creutzfeld-Jakob's syndrome/disease, bovine spongiform encephalopathy (BSE) prion related infections, diseases involving mitochondrial dysfunction, diseases involving β-amyloid and/or tauopathy, Down's syndrome, motor neuron diseases, amyotrophic lateral sclerosis (ALS), olivoponto-cerebellar atrophy, Parkinson's disease, Neuronal Ceroid Lipofuscinosis, AIDS dementia complex, AIDS-related dementia, dementia related to HIV infections, HIV-1 encephalopathy, AIDS encephalopathy, Korsakoff syndrome, vascular dementia, and corticobasal degeneration;

neurological disorders, including tinnitus, hearing loss, sound- or drug-induced tinnitus, haloperidol-induced dyskinesias, dopaminomimetic-induced dyskinesias, chorea, Huntington's chorea, athetosis, dystonia, stereotypy, ballism, tardive dyskinesias, tic disorder, spasmodic torticollis, blepharospasm, focal and generalized dystonia, nystagmus, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, L-dopa-induced dykinesias, L-dopa-induced dykinesias in Parkinson's disease therapy, dyskinesias, dyskinesia in Huntington's disease, drug induced dyskinesias, neuroleptic-induced dyskinesias, neurodegenerative cerebellar ataxias, centrally induced neuropathic pain, convulsions, epileptic convulsions, epilepsy, temporal lobe epilepsy, myoclonic epilepsy, tremor, dementia in Alzheimer's disease, dementia in Korsakoff syndrome, dementia, hereditary cerebellar ataxias, sleep disorders, movement disorders, essential tremor, muscle spasms, and spasticity;

psychological/psychiatric disorders, including generalized anxiety disorder, obsessive-compulsive disorder, panic disorder, posttraumatic stress disorder, social phobia, phobic disorders, substance-induced anxiety disorder, delusional disorder, schizoaffective disorder, schizophreniform disorder, substance-induced psychotic disorder, delirium, post-operative cognitive deficit (POCD), cognitive impairment, learning impairment, anxiety disorders, panic disorders, anxiety and panic disorders, social anxiety disorder (SAD), attention deficit hyperactivity disorder (ADHD), attention deficit syndrome (ADS), dementia, posttraumatic stress disorder (PTSD), schizophrenia, positive or cognitive or negative symptoms of schizophrenia, major depressive disorder, major depression, depression, bipolar manic-depressive disorder, sleep disorders, agoraphobia, bulimia nervosa, eating disorders, obesity, obesity-related disorders, obesity abuse, food addiction, binge eating disorders, and hyperactivity in children;

drug/alcohol abuse, including craving (e.g., for drugs of abuse), abuse, addiction, nicotine addiction, nicotine abuse, alcohol addiction, alcohol abuse, opiate addiction, opiate abuse, cocaine addiction, cocaine abuse, amphetamine addiction, and amphetamine abuse;

skin diseases, including atopic dermatitis, itching, skin lesions induced by severe itching or atopic dermatitis, systemic sclerosis, pruritic conditions, and pruritis;

diseases of the gastro-intestinal tract and metabolic diseases, including diarrhoea, hepatic encephalopathy, hypoglycaemia, gastroesophageal reflux disease (GERD), gastrointestinal dysfunction, lower esophageal sphincter (LES) disease, functional gastrointestinal disorders, dyspepsia, vomiting, urinary incontinence, and regurgitation;

diseases of the immune system, including Sjogren's syndrome, systemic lupus erythematosus, and multiple sclerosis (MS);

eye diseases, including eye injuries, eye diseases, eye disorders, glaucoma, retinopathy, and macular degeneration;

diseases of the respiratory tract, including respiratory tract infection, chronic laryngitis, asthma, reflux-related asthma, and lung disease;

migraine; autism; restless leg syndrome (RLS); Tourette syndrome; micturition disorders; neuromuscular disorder in the lower urinary tract; and drug tolerance to opioids.

A number of quinoline derivatives have been previously described.

U.S. Pat. No. 7,084,156 discloses 2-aminoquinolines of general formula (I) as melanin concentrating hormone receptor antagonists:

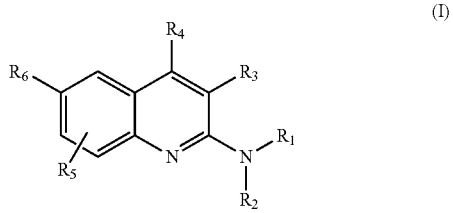

wherein $R_1$ and $R_2$ represent, e.g., hydrogen, $C_{1-6}$alkyl, cycloalkyl, heterocycloalkyl, aryl (wherein these groups may be further substituted); $R_3$ represents e.g., hydrogen, halogen, $C_{1-8}$alkyl, perfluoro$C_{1-6}$alkyl, cycloalkyl, aryl, heteroaryl, $OR^7$, $NR^7R^7$, $CO_2R^7$ (wherein $R^7$ represents, e.g., hydrogen, $C_{1-6}$alkyl, aryl, heteroaryl, cycloalkyl); $R_4$ represents, e.g., hydrogen, halogen, $C_{1-6}$alkyl, trifluoromethyl, cycloalkyl, $OR^7$, $NR^7R^7$, $CO_2R^7$; $R_5$ represents, e.g., hydrogen, halogen, $C_{1-6}$alkyl, perfluoro$C_{1-6}$alkyl, $OR^7$, $NR^7R^7$; and $R^6$ represents, e.g., —$(CH_2)_n$—$R^7$, —$(CH_2)_n$-aryl-$R^7$, —$(CH_2)_n$-heteroaryl-$R^7$, —$(CH_2)_n$—$NR^7C(O)$—$R^7$, —$(CH_2)_n$—$N(R^7)_2$—$R^7$, wherein n represents 0 to 5 and wherein the hydrogen atoms of the $(CH_2)_n$ moiety may be further substituted.

U.S. Pat. No. 7,087,758 discloses quinoline compounds of general formula (I) as inhibitors of hYAK1 and hYAK3 kinases:

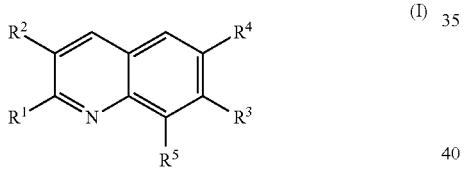

wherein $R^1$ represents, e.g., NH—$C_{1-6}$alkyl, NH—$C_{3-7}$cycloalkyl, NH-aryl, NH-Het (wherein these groups may be further substituted); $R^2$ represents, e.g., $CO_2H$, $CONH_2$, CHNOH; $R^3$ represents, e.g., H, OH, $C_{1-6}$alkyl, halogen; $R^4$ represents, e.g., H, $C_{1-6}$alkyl, $C_{3-7}$cycloalkyl, halogen; $R^5$ represents H or halogen.

US Published Application No. 2006/0106058 discloses 3-carboxy quinoline derivatives of general formula (I) as YAK3 inhibitors:

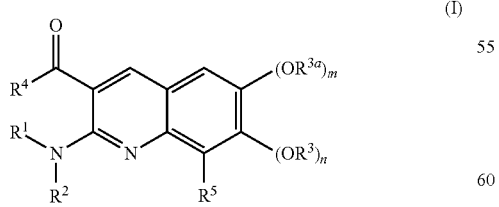

wherein $R^1$ represents H or $C_1$-$C_6$alkyl; $R^2$ represents $(Q)_q$-$(Q')_r$-$(Q^2)$, wherein Q represents $CH_2$, q represents 0-4, Q' represents O, NH, or CHOH, r represents 0 or 1, and $Q^2$ represents, H, $C_1$-$C_6$alkyl, aryl, heterocyclic, $C_3$-$C_7$cycloalkyl, C(O)$OR^b$ (wherein Rb represents H, or $C_2$-$C_4$alkenyl), or $NR^bR^b$, or heteroaryl, wherein $Q^2$ may be further substituted; $R^3$ and $R^{3a}$ represent H or $C_1$-$C_6$alkyl, or may combine to form a ring; m and n represent 0 or 1; $R^4$ represents OH, $NH(SO_2)R^c$, or $NR^b(R)$ (wherein $R^c$ represents aryl or $C_1$-$C_6$alkyl); and $R^5$ represents H or halogen.

US Published Application No. 2007/0197509 discloses compounds of general Formula (2) as modulators of gated ion channel activity:

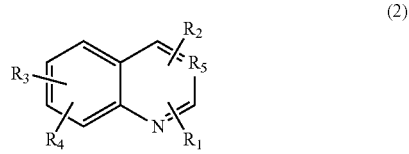

wherein $R_1$, $R_3$, and $R_4$ represent, e.g., hydrogen, optionally substituted amino, cyano, nitro, $CO_2H$, amide, halogen, $R_2$ represents, e.g., hydrogen, optional substituted amino, amide, halogen, $CO_2X^1$ (wherein $X^1$ represents hydrogen, $C_{1-6}$alkyl, amino, or optionally substituted aryl) as well as more complex substituents, and $R_5$ represents N, C, or CH.

U.S. Pat. No. 7,109,212 discloses quinoline and isoquinoline derivatives of general formula (I) as inflammation inhibitors:

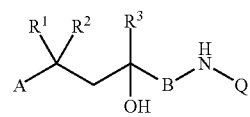

wherein A represents optionally substituted aryl, benzyl, or phenethyl; $R^1$ and $R^2$ represent hydrogen, methy, or ethyl or combine to form a ring; $R^3$ represents $C_{1-3}$alkyl optionally substituted by fluorine, B represents methylene (optionally substituted by methyl or ethyl) or carbonyl; and Q represents an optionally substituted quinolinyl or isoquinolinyl group.

International Publication No. WO 02/26713 discloses antiparasitic compounds of general Formula (I):

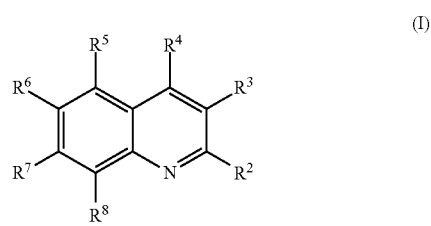

wherein $R^2$-$R^8$ represent, e.g., hydrogen, $C_1$-$C_{20}$alkyl, $C_6$-$C_{15}$aryl, halo, $NR^{10}R^{11}$, $COOR^{10}$ (wherein $R^{10}$ and $R^{11}$ represent hydrogen, optionally substituted $C_1$-$C_{20}$alkyl, and optionally substituted $C_6$-$C_{15}$aryl).

U.S. Pat. No. 4,962,203 discloses compounds of general Formula I as selective antagonists of leukotrienes of $D_4$:

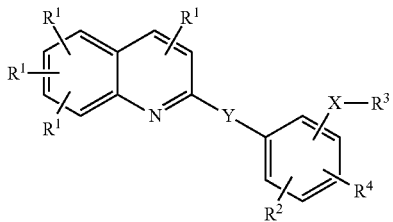

wherein $R^1$ represents, e.g., H, halogen, $C_1$-$C_8$alkyl, $OR^2$, $NR^2R^2$, $COOR^2$, $NO_2$ (wherein $R^2$ represents, e.g., H, $C_1$-$C_8$alkyl); $R^3$ represents -$(A)_m$-$(CR^2{=}CR^2)_p$—$(CR^2R^2)_m$-Q; A represents $CR^2R^4$ or $C{=}O$; Q represents, e.g., $COOR^2$, tetrazole; $R^4$ represents, e.g., H, halogen, NO2; Y represents e.g., $(CR^2{=}CR^2)_n$, —X—$CR^2R^2$, —$CR^2R^2$—X; m represents 0-8; n represents 1-2; and p represents 0-2.

U.S. Pat. No. 5,801,180 discloses compounds of general formula (1) as useful in treating various ischemic heart diseases:

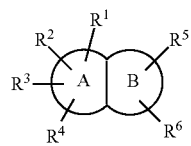

wherein ring A represents a benzene ring, a pyridine ring, or a cyclohexane ring; ring B represents a pyridine ring, a pyrimidine ring, or an imidazole ring; $R^1$-$R^4$ represent, e.g., hydrogen, halogen, lower alkyl optionally substituted by halogen, lower alkoxy, acylamino, carboxy, $NR^{45}R^{46}$ (wherein $R^{45}$ and $R^{46}$ represent hydrogen or lower alkyl or combine to form a ring); $R^5$ represents, e.g., hydrogen, halogen, hydroxyl, hydrazino, lower alkyl, carboxyl; $R^6$ represents, e.g., hydrogen, halogen, hydroxyl, amino, lower alkyl, —$N(R^{17})$—Y—$R^{18}$ (wherein $R^{17}$ represents hydrogen, lower alkyl, acyl, lower alkoxyalkyl, carboxyalkyl, or hydroxyalkyl, Y represents $(CH_2)_q$ (wherein q represents 1 to 8, and wherein the $CH_2$ group may be substituted) and $R^{18}$ represents hydrogen, hydroxyl, carboxyl, cyano, optionally substituted heteroaryl, or optionally substituted cycloalkyl.

THE PRESENT INVENTION

We have determined that certain quinoline derivatives are glycine B antagonists. Therefore, these substances may be therapeutically beneficial in the treatment of conditions which involve excitotoxicity and malfunctioning of glutamatergic neurotransmission. These substances may be administered in the form of a pharmaceutical composition, wherein they are present together with one or more pharmaceutically acceptable diluents, carriers, or excipients.

OBJECTS OF THE INVENTION

It is an object of the present invention to provide novel pharmaceutical compounds which are glycine B antagonists and pharmaceutical compositions thereof. It is a further object of the invention to provide a novel method of treating, eliminating, alleviating, palliating, or ameliorating undesirable conditions, including CNS conditions, associated with excitotoxicity and malfunctioning of glutamatergic neurotransmission by employing a compound of the invention or a pharmaceutical composition containing the same.

Yet additional objects will become apparent hereinafter, and still further objects will be apparent to one skilled in the art.

SUMMARY OF THE INVENTION

What we therefore believe to be comprised by our invention may be summarized inter alia in the following words: A compound selected from those of Formula I

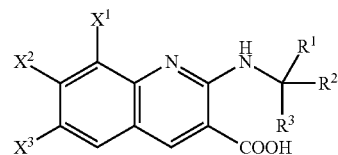

wherein
$X^1$ represents hydrogen, halogen, nitro, trifluoromethyl, $C_{1-6}$alkyl, $C_{1-6}$alkoxy, hydroxy-$C_{1-6}$alkyl, $C_{1-6}$alkoxy-$C_{1-6}$alkyl, or amino-$C_{1-6}$alkyl, acylamino-$Cl_{1-6}$alkyl;
$X^2$ represents hydrogen, halogen, nitro, trifluoromethyl, $C_{1-6}$alkyl, $C_{1-6}$alkoxy, aryl-$C_{1-6}$alkoxy, or heteroaryl-$C_{1-6}$alkoxy;
$X^3$ represents hydrogen, $C_{1-6}$alkyl, halogen, nitro, or trifluoromethyl;
$R^1$ represents COOH, $COOR^4$, $CONH_2$, $CONHR^5$, $CONR^5R^6$, or $CH_2OH$,
$R^2$ represents hydrogen, $CONH_2$, $CH_2OH$, $C_{1-6}$alkyl, $C_{2-6}$alkenyl, $C_{2-6}$alkynyl, hydroxy-$C_{1-6}$alkyl, amino-$C_{1-6}$ alkyl, carboxy-$C_{1-6}$ alkyl, $C_{1-6}$alkoxy-$C_{1-6}$alkyl, carbamoyl-$C_{1-6}$alkyl, aryl, heteroaryl, cyclo-$C_{3-12}$alkyl, cyclo-$C_{3-12}$alkyl-$C_{1-6}$alkyl, cyclo-$C_{3-12}$alkoxy-$C_{1-6}$ alkyl, aryloxy-$C_{1-6}$alkyl, heteroaryloxy-$C_{1-6}$alkyl, arylsulfanyl-$C_{1-6}$alkyl, heteroarylsulfanyl-$C_{1-6}$alkyl, aryl-$C_{1-6}$alkyl, heteroaryl-$C_{1-6}$alkyl, cyclo-$C_{3-12}$alkyl-$C_{1-6}$ alkyl, aryl-$C_{1-6}$alkoxy, heteroaryl-$C_{1-6}$alkoxy, aryl-$C_{1-6}$alkoxy-$C_{1-6}$alkyl, heteroaryl-$C_{1-6}$alkoxy-$C_{1-6}$alkyl, heteroaryl-$C_{1-6}$alkylsulfanyl-$C_{1-6}$alkyl, arylamino-$C_{1-6}$ alkyl, heteroarylamino-$C_{1-6}$alkyl, cyclo-$C_{3-12}$alkyl-amino-$C_{1-6}$alkyl, carboxy-$C_{1-6}$alkylamino-$C_{1-6}$alkyl, acylamino-$C_{1-6}$alkyl, arylsulfonylamino-$C_{1-6}$alkyl, $C_{1-6}$alkylsulfonylamino-$C_{1-6}$alkyl, $C_{1-6}$alkylaminocarbonyl-$C_{1-6}$alkyl, cyclo-$C_{3-12}$alkylaminocarbonyl-$C_{1-6}$ alkyl, arylaminocarbonyl-$C_{1-6}$alkyl, heteroarylaminocarbonyl-$C_{1-6}$alkyl, aryl-$C_{1-6}$alkylaminocarbonyl-$C_{1-6}$alkyl, heteroaryl-$C_{1-6}$alkylaminocarbonyl-$C_{1-6}$ alkyl, hydroxy-$C_{1-6}$alkylaminocarbonyl-$C_{1-6}$alkyl, carboxy-$C_{1-6}$alkylaminocarbonyl-$C_{1-6}$alkyl, di-($C_{1-6}$ alkyl)aminocarbonyl-$C_{1-6}$alkyl, heteroaryloxy-aryl$C_{1-6}$ alkyl, aryl$C_{1-6}$alkoxy-aryl$C_{1-6}$alkyl, heteroarylamino-aryl-$C_{1-6}$alkyl, aryl$C_{1-6}$alkyl-heteroaryl-$C_{1-6}$alkyl, or heteroarylamino-$C_{1-6}$alkyl-aryl-$C_{1-6}$alkyl;
$R^3$ represents hydrogen, $C_{1-6}$alkyl, hydroxy-$C_{1-6}$alkyl, or carboxy-$C_{1-6}$alkyl,
or $R^2$ and $R^3$ together with the carbon atom to which they are attached represent a 3, 4, 5, 6 or 7-membered ring having from 0-3 heteroatoms selected from oxygen, nitrogen, and sulfur, which ring may optionally be partially unsaturated may optionally be fused to an aryl or heteroaryl ring;

$R^4$ represents $C_{1-6}$alkyl, hydroxy-$C_{1-6}$alkyl, $C_{1-6}$alkoxy-$C_{1-6}$alkyl, di-$C_{1-6}$alkylamino-$C_{1-6}$alkyl, aryl-$C_{1-6}$alkyl, or aryloxy-$C_{1-6}$alkyl;

$R^5$ and $R^6$, which may be the same or different, each independently represent $C_{1-6}$alkyl, cyclo-$C_{3-12}$alkyl, $C_{3-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl;

or $R^5$ and $R^6$ may together represent —$(CH_2)_m$— with m being 3, 4, 5 or 6, or $R^5$ and $R^6$ together with the nitrogen atom they are attached may represent a 4, 5, 6 or 7-membered ring which may be saturated or unsaturated, and wherein the ring in addition to the nitrogen atom may contain an additional heteroatom selected from sulfur, oxygen and nitrogen and may be substituted by one or more substituents selected from COOH, $CONH_2$, $CONHR^5$, $C_{1-6}$alkyl, hydroxy-$C_{1-6}$alkyl, carboxy-$C_{1-6}$alkyl, carbamoyl-$C_{1-6}$alkyl, cyclo-$C_{3-12}$alkyl, $C_{2-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl, arylamino, heteroarylamino, aryl-$C_{1-6}$alkylamino, and heteroaryl-$C_{1-6}$alkylamino;

wherein the term "aryl" means phenyl or naphthyl, or phenyl substituted by one or more substituents selected independently from a halogen, amino, hydroxy, nitro, cyano, COOH, $COOR^4$, $CONH_2$, $CONHR^5$, $CONR^5R^6$, $CH_2OH$, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo-$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$alkylamino, hydroxy-$C_{1-6}$alkylamino, carboxy-$C_{1-6}$ alkylamino, $C_{1-6}$alkyl, di-($C_{1-6}$alkyl)amino, acylamino, di-($C_{1-6}$alkyl)amino-$C_{1-6}$alkyl, carboxy-$C_{1-6}$ alkylamino-$C_{1-6}$alkyl, $C_{1-6}$alkylamino-$C_{1-6}$alkoxy, di-($C_{1-6}$alkyl)amino-$C_{1-6}$alkoxy, carboxy-$C_{1-6}$alkylamino-$C_{1-6}$ alkoxy, $C_{1-6}$alkylsulfonylamino, arylsulfonylamino, $C_{1-6}$alkylsulfonylamino-$C_{1-6}$alkyl, $C_{1-6}$alkyl-aminosulfonyl, di-($C_{1-6}$alkyl)aminosulfonyl, arylaminosulfonyl, heteroarylaminosulfonyl, $C_{1-6}$alkylaminocarbonyl-$C_{1-6}$ alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$alkylaminocarbonyl-$C_{1-6}$alkyl, carboxy-$C_{1-6}$alkylaminocarbonyl-$C_{1-6}$alkyl, di-($C_{1-6}$alkyl)aminocarbonyl-$C_{1-6}$alkyl, aryl$C_{2-6}$alkynyl, and heteroaryl$C_{2-6}$alkynyl;

and the term "heteroaryl" means an aromatic 5-6 membered ring comprising one to four heteroatoms selected from oxygen, sulfur and nitrogen, or a bicyclic group containing a 5-6 membered ring comprising one to four heteroatoms selected from oxygen, sulfur and nitrogen fused with a benzene ring or with a 5-6 membered ring comprising one to four heteroatoms selected from oxygen, sulfur and nitrogen, wherein the heteroaryl is optionally substituted by one or more substituents selected independently from a halogen, amino, hydroxy, nitro, cyano, COOH, $COOR^4$, $CONH_2$, $CONHR^5$, $CONR^5R^6$, $CH_2OH$, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$alkylamino, hydroxy-$C_{1-6}$alkylamino, carboxy-$C_{1-6}$ alkylamino, $C_{1-6}$alkylamino-$C_{1-6}$alkyl, di-($C_{1-6}$alkyl) amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$ alkoxy, di-($C_{1-6}$alkyl)amino-$C_{1-6}$alkoxy, carboxy-$C_{1-6}$ alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkylaminosulfonyl, di-($C_{1-6}$alkyl)aminosulfonyl, arylaminosulfonyl, heteroarylaminosulfonyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$ alkylaminocarbonyl-$C_{1-6}$alkyl, carboxy-$C_{1-6}$ alkylaminocarbonyl-$C_{1-6}$alkyl, and di-($C_{1-6}$alkyl)aminocarbonyl-$C_{1-6}$alkyl;

its optical isomers, polymorphs, analogs, derivatives, prodrugs, and pharmaceutically-acceptable acid and base addition salts, hydrates and solvates thereof.

Such a compound of Formula I, wherein $R^2$ represents hydrogen, $CH_2OH$, $C_{1-6}$alkyl, hydroxy-$C_{1-6}$alkyl, amino-$C_{1-6}$ alkyl, carboxy-$C_{1-6}$alkyl, carbamoyl-$C_{1-6}$alkyl, aryl, aryl-$C_{1-6}$alkyl, heteroaryl-$C_{1-6}$alkyl, cyclo-$C_{3-12}$alkyl-$C_{1-6}$ alkyl, aryl-$C_{1-6}$alkoxy-$C_{1-6}$alkyl, heteroarylamino-$C_{1-6}$ alkyl, acylamino-$C_{1-6}$alkyl, arylaminocarbonyl-$C_{1-6}$alkyl, aryl-$C_{1-6}$alkylaminocarbonyl-$C_{1-6}$alkyl, heteroaryloxy-aryl$C_{1-6}$alkyl, aryl$C_{1-6}$alkoxy-aryl-$C_{1-6}$alkyl, heteroarylamino-aryl-$C_{1-6}$alkyl, aryl-$C_{1-6}$alkyl-heteroaryl-$C_{1-6}$alkyl, or heteroarylamino-$C_{1-6}$alkyl-aryl-$C_{1-6}$alkyl; $R^3$ represents hydrogen or $R^2$ and $R^3$ together with the carbon atom to which they are attached form a 3, 4, 5, 6, or 7-membered ring which is optionally fused to an aryl ring.

Such a compound of Formula I, wherein $R^2$ represents aryl-$C_{1-6}$alkyl, heteroaryl-$C_{1-6}$alkyl, cyclo-$C_{3-12}$alkyl-$C_{1-6}$ alkyl, heteroarylamino-$C_{1-6}$alkyl, heteroaryloxy-aryl$C_{1-6}$ alkyl, aryl-$C_{1-6}$alkoxy-$C_{1-6}$alkyl, or aryl$C_{1-6}$alkoxy-aryl-$C_{1-6}$ alkyl; and $R^3$ represents hydrogen.

Such a compound of Formula I, wherein $X^1$, $X^2$, and $X^3$ each independently represent hydrogen, halogen, $CF_3$, or $C_{1-6}$alkyl.

Such a compound of Formula I, wherein $X^1$, $X^2$, and $X^3$ each independently represent hydrogen, halogen, $CF_3$, or methyl.

Such a compound of Formula I, wherein $X^1$ and $X^2$ each independently represent hydrogen, halogen, $CF_3$ or methyl and $X^3$ represents halogen, $CF_3$ or methyl.

Such a compound of Formula I, wherein $X^1$ and $X^2$ each independently represent hydrogen, halogen, or methyl and $X^3$ represents halogen.

Such a compound of Formula I, wherein $R^1$ represents COOH, $CONH_2$, $CONHR^5$, or $CH_2OH$.

Such a compound of Formula I, wherein $X^1$ and $X^2$ each independently represent hydrogen, chlorine, bromine or methyl, and $X^3$ represents chlorine or bromine, and $R^1$ represents COOH.

A further aspect of the invention relates to a compound of Formula I, which is selected from those of Formula IA

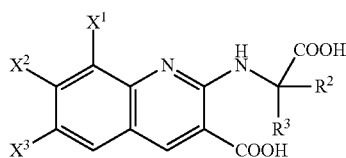

wherein $X^1$, $X^2$, $X^3$, $R^2$, and $R^3$ are as defined above for Formula I, and optical isomers, polymorphs, analogs, derivatives, prodrugs, and pharmaceutically-acceptable acid and base addition salts, hydrates, and solvates thereof.

Such a compound of Formula IA, wherein $R^2$ represents aryl-$C_{1-6}$alkyl, heteroaryl-$C_{1-6}$alkyl, cyclo-$C_{3-12}$alkyl-$C_{1-6}$alkyl, heteroarylamino-$C_{1-6}$alkyl, heteroaryloxy-aryl$C_{1-6}$alkyl, aryl-$C_{1-6}$alkoxy-$C_{1-6}$alkyl, or aryl$C_{1-6}$alkoxy-aryl-$C_{1-6}$alkyl; and $R^3$ represents hydrogen.

Such a compound of Formula IA, wherein $X^1$, $X^2$, and $X^3$ each independently represent hydrogen, halogen, $CF_3$, or $C_{1-6}$alkyl.

Such a compound of Formula IA, wherein $X^1$, $X^2$, and $X^3$ each independently represent hydrogen, halogen, $CF_3$, or methyl.

Such a compound of Formula IA, wherein $X^1$ and $X^2$ each independently represent hydrogen, halogen, $CF_3$ or methyl, and $X^3$ represents halogen, $CF_3$ or methyl.

Such a compound of Formula IA, wherein $X^1$ and $X^2$ each independently represent hydrogen, halogen, or methyl, and $X^3$ represents halogen.

Such a compound of Formula IA, wherein $X^1$ and $X^2$ each independently represent hydrogen, chlorine, bromine or methyl, and $X^3$ represents chlorine or bromine.

Specific compounds of Formula I within the present invention include but are not limited to:

2-((S)-1-Carboxy-2-phenyl-ethylamino)-6-chloro-quinoline-3-carboxylic acid,
2-[1-Carboxy-2-(1H-indol-3-yl)-ethylamino]-6-chloro-quinoline-3-carboxylic acid,
2-(1-Carboxy-butylamino)-6-chloro-quinoline-3-carboxylic acid,
2-(Carboxymethyl-amino)-6-chloro-quinoline-3-carboxylic acid,
2-[(Carboxy-phenyl-methyl)-amino]-6-chloro-quinoline-3-carboxylic acid,
2-((R)-1-Carboxy-2-phenyl-ethylamino)-6-chloro-quinoline-3-carboxylic acid,
6-Chloro-2-((R)-2-hydroxy-1-phenylethylamino)-quinoline-3-carboxylic acid,
2-{(S)-1-Carboxy-2-[4-(3-carboxy-6-chloroquinolin-2-yloxy)-phenyl]-ethylamino}-6-chloro-quinoline-3-carboxylic acid,
2-[(S)-1-Carboxy-2-(4-nitro-phenyl)-ethylamino]-6-chloro-quinoline-3-carboxylic acid,
6-Chloro-2-((R)-1-hydroxymethyl-2-phenyl-ethylamino)-quinoline-3-carboxylic acid,
6-Chloro-2-((S)-2-hydroxy-1-phenyl-ethylamino)-quinoline-3-carboxylic acid,
2-[(R)-1-Carboxy-2-(1H-indol-3-yl)-ethylamino]-6-chloro-quinoline-3-carboxylic acid,
6-Chloro-2-((S)-1-hydroxymethyl-2-phenyl-ethylamino)-quinoline-3-carboxylic acid,
6-Chloro-2-[(S)-1-hydroxymethyl-2-(1H-indol-3-yl)-ethylamino]-quinoline-3-carboxylic acid,
2-[(S)-1-Carboxy-2-(1-methyl-1H-indol-3-yl)-ethylamino]-6-chloro-quinoline-3-carboxylic acid,
2-((S)-5-Benzyloxycarbonylamino-1-carboxy-pentylamino)-6-chloro-quinoline-3-carboxylic acid,
2-[(S)-1-Carboxy-2-(4-methoxy-phenyl)-ethylamino]-6-chloro-quinoline-3-carboxylic acid,
2-[1-Carboxy-2-(5-methoxy-1H-indol-3-yl)-ethylamino]-6-chloro-quinoline-3-carboxylic acid,
2-((R)-2-Benzyloxy-1-carboxy-ethylamino)-6-chloro-quinoline-3-carboxylic acid,
2-[(R)-1-Carboxy-2-(1-methyl-1H-indol-3-yl)-ethylamino]-6-chloro-quinoline-3-carboxylic acid,
2-[1-Carboxy-2-(5-methyl-1H-indol-3-yl)-ethylamino]-6-chloro-quinoline-3-carboxylic acid,
2-[(S)-2-(4-Benzyloxy-phenyl)-1-carboxy-ethylamino]-6-chloro-quinoline-3-carboxylic acid,
2-[(S)-1-Carboxy-2-(4-chloro-phenyl)-ethylamino]-6-chloro-quinoline-3-carboxylic acid,
2-(1-Carboxy-indan-1-ylamino)-6-chloro-quinoline-3-carboxylic acid,
2-[1-Carboxy-2-(5-fluoro-1H-indol-3-yl)-ethylamino]-6-chloro-quinoline-3-carboxylic acid,
2-(1-Carboxy-ethylamino)-6-chloro-quinoline-3-carboxylic acid,
2-((S)-5-Amino-1-carboxy-pentylamino)-6-chloro-quinoline-3-carboxylic acid,
2-(1-Carboxy-3-phenyl-propylamino)-6-chloro-quinoline-3-carboxylic acid,
2-[1-Carboxy-2-(1H-imidazol-4-yl)-ethylamino]-quinoline-3-carboxylic acid,
erythro-2-(1-Carboxy-2-phenyl-propylamino)-6-chloro-quinoline-3-carboxylic acid,
threo-2-(1-Carboxy-2-phenyl-propylamino)-6-chloro-quinoline-3-carboxylic acid,
2-((S)-1-Carboxy-2-phenyl-ethylamino)-6,7-dichloro-quinoline-3-carboxylic acid,
2-[1-Carboxy-2-(6-fluoro-1H-indol-3-yl)-ethylamino]-6-chloro-quinoline-3-carboxylic acid,
2-[(S)-1-Carboxy-2-(4-hydroxy-phenyl)-ethylamino]-6-chloro-quinoline-3-carboxylic acid,
2-((S)-1-Carboxy-2-cyclohexyl-ethylamino)-6-chloro-quinoline-3-carboxylic acid,
2-[(R)-1-Carboxy-2-(1H-indol-3-yl)-ethylamino]-6,7-dichloro-quinoline-3-carboxylic acid,
2-[(S)-1-Carboxy-2-(3,4-dihydroxy-phenyl)-ethylamino]-6-chloro-quinoline-3-carboxylic acid,
2-[1-Carboxy-2-(3-carboxy-6-chloro-quinolin-2-ylamino)-ethylamino]-6-chloro-quinoline-3-carboxylic acid,
2-[1-Carboxy-2-(4-fluoro-phenyl)-ethylamino]-6-chloro-quinoline-3-carboxylic acid,
2-[1-Carboxy-2-(2-fluoro-phenyl)-ethylamino]-6-chloro-quinoline-3-carboxylic acid,
2-[(S)-1-Carboxy-2-(4-hydroxy-3-nitro-phenyl)-ethylamino]-6-chloro-quinoline-3-carboxylic acid,
2-((S)-1-Carboxy-2-phenyl-ethylamino)-6,8-dichloro-quinoline-3-carboxylic acid,
6-Chloro-2-[1-(naphthalen-2-ylcarbamoyl)-ethylamino]-quinoline-3-carboxylic acid,
2-((R)-1-Carboxy-2-phenyl-ethylamino)-quinoline-3-carboxylic acid,
2-[(R)-1-Carboxy-2-(1H-indol-3-yl)-ethylamino]-quinoline-3-carboxylic acid,
2-[1-(1-Carbamoyl-2-phenyl-ethylcarbamoyl)-2-phenyl-ethylamino]-6-chloro-quinoline-3-carboxylic acid,
6-Bromo-2-((R)-1-carboxy-2-phenyl-ethylamino)-quinoline-3-carboxylic acid,
2-{(S)-2-[3-Amino-4-(3-carboxy-6-chloro-quinolin-2-yloxy)-phenyl]-1-carboxy-ethylamino}-6-chloro-quinoline-3-carboxylic acid, 2-[(S)-2-(3-Amino-4-hydroxy-phenyl)-1-carboxy-ethylamino]-6-chloro-quinoline-3-carboxylic acid,
2-[(S)-1-Carboxy-4-(6-chloro-3-carboxy-quinolin-2-ylamino)-butylamino]-6-chloro-quinoline-3-carboxylic acid,
2-[(S)-1-Carboxy-2-(3-chloro-4-hydroxy-phenyl)-ethylamino]-6-chloro-quinoline-3-carboxylic acid,
2-[1-Carboxy-2-(3-fluoro-4-hydroxy-phenyl)-ethylamino]-6-chloro-quinoline-3-carboxylic acid,
2-[1-Carboxy-2-(4-carboxy-phenyl)-ethylamino]-6-chloro-quinoline-3-carboxylic acid,
2-[1-[1-Carboxy-2-(4-carboxy-phenyl)-ethylcarbamoyl]-2-(4-carboxy-phenyl)-ethylamino]-6-chloro-quinoline-3-carboxylic acid,
2-((S)-1-Carboxy-2-pyridin-4-yl-ethylamino)-6-chloro-quinoline-3-carboxylic acid,
6,8-Dibromo-2-(1-carboxy-2-phenyl-ethylamino)-quinoline-3-carboxylic acid,
2-[1-Carboxy-2-(3,5-dimethyl-pyrazol-1-yl)-ethylamino]-6-chloro-quinoline-3-carboxylic acid,
2-[2-(4-Amino-phenyl)-1-carboxy-ethylamino]-6-chloro-quinoline-3-carboxylic acid,
2-{1-Carboxy-2-[4-(3-carboxy-6-chloro-quinolin-2-ylamino)-phenyl]-ethylamino}-6-chloro-quinoline-3-carboxylic acid,
2-[1-[1-Carboxy-2-(3-carboxy-phenyl)-ethylcarbamoyl]-2-(3-carboxy-phenyl)-ethylamino]-6-chloro-quinoline-3-carboxylic acid,
2-[1-Carboxy-2-(3-methoxy-phenyl)-ethylamino]-6-chloro-quinoline-3-carboxylic acid,
2-[1-Carboxy-2-(4-phenylethynyl-phenyl)-ethylamino]-6-chloro-quinoline-3-carboxylic acid,
2-[1-Carboxy-2-(3-hydroxy-phenyl)-ethylamino]-6-chloro-quinoline-3-carboxylic acid,
2-[1-Carboxy-2-(3-hydroxy-phenyl)-ethylamino]-6,8-dichloro-quinoline-3-carboxylic acid,
2-[1-Carboxy-2-(2-methyl-benzooxazol-5-yl)-ethylamino]-6-chloro-quinoline-3-carboxylic acid,
2-[1-Carboxy-2-(phenylcarbamoyl-ethylamino)]-6-chloro-quinoline-3-carboxylic acid,
2-[1-Carboxy-2-(1H-indol-3-yl)-ethylamino]-6,8-dichloro-quinoline-3-carboxylic acid,
2-[1-Carboxy-2-(2-chloro-5-methoxy-phenyl)-ethylamino]-6-chloro-quinoline-3-carboxylic acid,
6-Chloro-2-[2-hydroxy-1-(3-methoxy-phenylcarbamoyl)-ethylamino]-quinoline-3-carboxylic acid,
6-Chloro-2-(phenylcarbamoyl-methyl-amino)-quinoline-3-carboxylic acid,
6,8-Dichloro-2-(phenylcarbamoyl-methyl-amino)-quinoline-3-carboxylic acid,
2-[1-Carboxy-2-(2-methoxy-phenyl)-ethylamino]-6-chloro-quinoline-3-carboxylic acid,
2-(2-Carbamoyl-1-carboxy-ethylamino)-6-chloro-quinoline-3-carboxylic acid,
2-[1-Carboxy-2-(1-phenyl-ethylcarbamoyl)-ethylamino]-6-chloro-quinoline-3-carboxylic acid,
2-(2-Carboxy-1-phenylcarbamoyl-ethylamino)-6-chloro-quinoline-3-carboxylic acid,
6-Chloro-2-(2-hydroxy-1-phenylcarbamoyl-ethylamino)-quinoline-3-carboxylic acid,
2-(3-Carbamoyl-1-carboxy-propylamino)-6-chloro-quinoline-3-carboxylic acid,
2-{1-Carboxy-2-[1-(3-methyl-4-nitro-benzyl)-1H-imidazol-4-yl]-ethylamino}-6-chloro-quinoline-3-carboxylic acid,
2-(3-Carboxy-6-chloro-quinolin-2-ylamino)-3-phenyl-succinic acid,
2-{4-[2-(3-carboxy-6-chloro-quinolin-2-yl)amino-2-carboxy-ethyl]phenyl]-1-carboxy-ethylamino}-6-chloro-quinoline-3-carboxylic acid,
2-{2-[3-(3-carboxy-6-chloro-quinolin-2-yloxy)-phenyl]-1-carboxy-ethylamino}-6-chloro-quinoline-3-carboxylic acid,
2-{2-[3-[2-(3-carboxy-6-chloro-quinolin-2-yl)amino-2-carboxy-ethyl]-phenyl]-1-carboxy-ethylamino}-6-chloro-quinoline-3-carboxylic acid,
2-(1-Carboxy-2-thiophen-2-yl-ethylamino)-6-chloro-quinoline-3-carboxylic acid,
2-(1-Carbamoyl-2-phenyl-ethylamino)-6-chloro-quinoline-3-carboxylic acid,
6-Chloro-2-(1-methylcarbamoyl-2-phenyl-ethylamino)-quinoline-3-carboxylic acid,
6,8-Dichloro-2-(1-methylcarbamoyl-2-phenyl-ethylamino)-quinoline-3-carboxylic acid,
2-(2-Benzoylamino-1-carboxy-ethylamino)-6-chloro-quinoline-3-carboxylic acid,
6,8-Dichloro-2-(2-hydroxy-1-phenylcarbamoyl-ethylamino)-quinoline-3-carboxylic acid,
2-(1-Carboxy-2-phenylacetylamino-ethylamino)-6-chloro-quinoline-3-carboxylic acid,
2-[1-[1-Carboxy-2-(2-methoxy-phenyl)-ethylcarbamoyl]-2-(2-methoxy-phenyl)-ethylamino]-6-chloro-quinoline-3-carboxylic acid,
2-[1-[1-Carboxy-2-(2-chloro-5-methoxy-phenyl)-ethylcarbamoyl]-2-(2-chloro-5-methoxy-phenyl)-ethylamino]-6-chloro-quinoline-3-carboxylic acid,
2-[(1-Carboxy-2-thiophen-2-yl-ethylcarbamoyl)-2-thiophen-2-yl-ethylamino]-6-chloro-quinoline-3-carboxylic acid,
2-[1-Carboxy-2-(3-carboxy-phenyl)-ethylamino]-6-chloro-quinoline-3-carboxylic acid,
2-[1-[1-Carboxy-2-(4-phenylethynyl-phenyl)-ethylcarbamoyl]-2-(4-phenylethynyl-phenyl)-ethylamino]-6-chloro-quinoline-3-carboxylic acid,
2-(1-Carboxy-2-phenyl-ethylamino)-6-chloro-8-methylquinoline-3-carboxylic acid,
2-{1-Carboxy-2-[4-(quinolin-2-yloxy)-phenyl]-ethylamino}-6-chloro-quinoline-3-carboxylic acid,
2-[1-Carboxy-2-(1H-indol-3-yl)-ethylamino]-6-chloro-8-methylquinoline-3-carboxylic acid,
2-[1-Carboxy-2-(3-fluoro-phenyl)-ethylamino]-6-chloro-quinoline-3-carboxylic acid,
2-(1-Carboxy-2-pyridin-3-yl-ethylamino)-6-chloro-quinoline-3-carboxylic acid,
2-{(S)-1-Carboxy-2-[4-(3-carboxy-pyridin-2-yloxy)-phenyl]-ethylamino}-6-chloro-quinoline-3-carboxylic acid,
2-{(S)-2-[4-(5-Bromo-pyridin-2-yloxy)-phenyl]-1-carboxy-ethylamino}-6-chloro-quinoline-3-carboxylic acid,
6-Bromo-2-[1-carboxy-2-(4-hydroxy-phenyl)-ethylamino]-quinoline-3-carboxylic acid,
6-Bromo-2-{1-carboxy-2-[4-(3-carboxy-quinolin-2-yloxy)-phenyl]-ethylamino}-quinoline-3-carboxylic acid,
2-{1-Carboxy-2-[4-(quinolin-4-ylamino)-phenyl]-ethylamino}-6-chloro-quinoline-3-carboxylic acid,
2-{1-Carboxy-2-[4-(3-carboxy-pyridin-2-ylamino)-phenyl]-ethylamino}-6-chloro-quinoline-3-carboxylic acid,
2-{1-Carboxy-2-[4-(7-chloro-quinolin-4-ylamino)-phenyl]-ethylamino}-6-chloro-quinoline-3-carboxylic acid,
2-{1-Carboxy-2-[3-(3-carboxy-6-bromo-quinolin-2-yloxy)-phenyl]-ethylamino}-6-bromo-quinoline-3-carboxylic acid,
2-{1-Carboxy-2-[4-(quinolin-2-ylamino)-phenyl]-ethylamino}-6-chloro-quinoline-3-carboxylic acid, 2-{(S)-1-Carboxy-2-[4-(quinolin-4-yloxy)-phenyl]-ethylamino}-6-chloro-quinoline-3-carboxylic acid,
2-{1-Carboxy-2-[4-(3-carboxy-quinolin-2-yloxy)-phenyl]-ethylamino}-6-chloro-quinoline-3-carboxylic acid,
6-Bromo-2-{2-[4-(5-bromo-pyridin-2-yloxy)-phenyl]-1-carboxy-ethylamino}-quinoline-3-carboxylic acid,
6-Bromo-2-{1-carboxy-2-[4-(quinolin-2-yloxy)-phenyl]-ethylamino}-quinoline-3-carboxylic acid,
2-[2-(4-Bromo-phenyl)-1-carboxy-ethylamino]-6-chloro-quinoline-3-carboxylic acid,
(S)-2-(3-Carboxy-6-chloro-quinolin-2-ylamino)-succinic acid ammonia hydrate,
2-[1-Carboxy-2-(3-fluoro-phenyl)-ethylamino]-6,8-dichloro-quinoline-3-carboxylic acid,
2-(3-Carboxy-6,8-dichloro-quinolin-2-ylamino)-3-phenyl-succinic acid,
2-(2-Benzyloxy-1-phenylcarbamoyl-ethylamino)-6-chloro-quinoline-3-carboxylic acid,
2-[(S)-1-Carboxy-2-(4-hydroxy-phenyl)-ethylamino]-6,8-dichloro-quinoline-3-carboxylic acid,
2-(3-Carboxy-6-chloro-quinolin-2-ylamino)-3-(3-fluoro-phenyl)-succinic acid,
2-((S)-1-Carboxy-2-phenyl-ethylamino)-6,8-dimethyl-quinoline-3-carboxylic acid,
2-(2-Benzylcarbamoyl-1-carboxy-ethylamino)-6-chloro-quinoline-3-carboxylic acid,
2-{(S)-1-Carboxy-2-[4-(3-carboxy-6,8-dichloro-quinolin-2-yloxy)-phenyl]-ethylamino}-6,8-dichloro-quinoline-3-carboxylic acid,
2-[(S)-1-Carboxy-2-(1-methyl-1H-indol-3-yl)-ethylamino]-6,8-dichloro-quinoline-3-carboxylic acid,
2-{(S)-1-Carboxy-2-[4-(6-chloro-quinolin-2-yloxy)-phenyl]-ethylamino}-6-chloro-quinoline-3-carboxylic acid,
2-{(S)-1-Carboxy-2-[4-(8-chloro-quinolin-2-yloxy)-phenyl]-ethylamino}-6-chloro-quinoline-3-carboxylic acid,
2-{(S)-1-Carboxy-2-[4-(3-chloro-pyridin-2-yloxy)-phenyl]-ethylamino}-6-chloro-quinoline-3-carboxylic acid,
2-{(S)-1-Carboxy-2-[4-(5-trifluoromethyl-pyridin-2-yloxy)-phenyl]-ethylamino}-6-chloro-quinoline-3-carboxylic acid,
2-{(S)-1-Carboxy-2-[4-(5-chloro-pyridin-2-yloxy)-phenyl]-ethylamino}-6-chloro-quinoline-3-carboxylic acid,
2-{(S)-1-Carboxy-2-[4-(3-trifluoromethyl-pyridin-2-yloxy)-phenyl]-ethylamino}-6-chloro-quinoline-3-carboxylic acid,
2-{(S)-1-Carboxy-2-[4-(5-phenyl-[1,6]naphthyridin-2-yloxy)-phenyl]-ethylamino}-6-chloro-quinoline-3-carboxylic acid,
2-{1-Carboxy-2-[4-(5-iodo-pyridin-2-yloxy)-phenyl]-ethylamino}-6-chloro-quinoline-3-carboxylic acid,
6-Chloro-2-[(S)-1-(2-methoxy-ethoxycarbonyl)-2-phenyl-ethylamino]-quinoline-3-carboxylic acid,
2-{(S)-1-Carboxy-2-[4-(5-methyl-pyridin-2-yloxy)-phenyl]-ethylamino}-6-chloro-quinoline-3-carboxylic acid,
2-{(S)-1-Carboxy-2-[4-(4-methyl-pyridin-2-yloxy)-phenyl]-ethylamino}-6-chloro-quinoline-3-carboxylic acid,
2-{(S)-1-Carboxy-2-[4-(3-methyl-pyridin-2-yloxy)-phenyl]-ethylamino}-6-chloro-quinoline-3-carboxylic acid,
2-(3-Carboxy-6-chloro-quinolin-2-ylamino)-3-(3,5-difluoro-phenyl)-succinic acid,
6-Chloro-2-[1-(2-dimethylamino-ethoxycarbonyl)-2-pyridin-2-yl-ethylamino]-quinoline-3-carboxylic acid,
6-Chloro-2-(1-ethoxycarbonyl-2-pyridin-2-yl-ethylamino)-quinoline-3-carboxylic acid,
2-{(S)-2-[4-(3-Bromo-pyridin-2-yloxy)-phenyl]-1-carboxy-ethylamino}-6-chloro-quinoline-3-carboxylic acid,
2-{(S)-1-Carboxy-2-[4-(3,5-dichloro-pyridin-2-yloxy)-phenyl]-ethylamino}-6-chloro-quinoline-3-carboxylic acid,
2-{(S)-2-[4-(5-Amino-pyridin-2-yloxy)-phenyl]-1-carboxy-ethylamino}-6-chloro-quinoline-3-carboxylic acid,
2-{(S)-1-Carboxy-2-[4-(7-chloro-quinolin-4-yloxy)-phenyl]-ethylamino}-6-chloro-quinoline-3-carboxylic acid,
2-{(S)-1-Carboxy-2-[4-(5-chloro-3-fluoro-pyridin-2-yloxy)-phenyl]-ethylamino}-6-chloro-quinoline-3-carboxylic acid,
2-{(S)-2-[4-(3-Bromo-pyridin-4-yloxy)-phenyl]-1-carboxy-ethylamino}-6-chloro-quinoline-3-carboxylic acid,
2-{(S)-2-[4-(7-Bromo-isoquinolin-1-yloxy)-phenyl]-1-carboxy-ethylamino}-6-chloro-quinoline-3-carboxylic acid,
2-{(S)-1-Carboxy-2-[4-(2-chloro-pyridin-4-yloxy)-phenyl]-ethylamino}-6-chloro-quinoline-3-carboxylic acid,
2-{(S)-2-[4-(6-Bromo-[1,8]naphthyridin-4-yloxy)-phenyl]-1-carboxy-ethylamino}-6-chloro-quinoline-3-carboxylic acid,
2-{(S)-1-Carboxy-2-[4-(6-methyl-pyridin-2-yloxy)-phenyl]-ethylamino}-6-chloro-quinoline-3-carboxylic acid,
2-(1-Carboxy-2-pyridin-2-yl-ethylamino)-6-chloro-quinoline-3-carboxylic acid,
6-Chloro-2-((S)-2-phenyl-1-propylcarbamoyl-ethylamino)-quinoline-3-carboxylic acid,
6-Chloro-2-((S)-2-phenyl-1-phenylcarbamoyl-ethylamino)-quinoline-3-carboxylic acid,
2-((S)-1-Carboxy-2-hydroxy-ethylamino)-6-chloro-quinoline-3-carboxylic acid,
6-Chloro-2-[(S)-1-(2-hydroxy-ethylcarbamoyl)-2-phenyl-ethylamino]-quinoline-3-carboxylic acid,
6-Chloro-2-[(S)-2-phenyl-1-(1H-tetrazol-5-ylcarbamoyl)-ethylamino]-quinoline-3-carboxylic acid,
2-[(S)-1-Carboxy-2-(1H-indol-3-yl)-ethylamino]-6,8-dichloro-quinoline-3-carboxylic acid,
2-((S)-1-Carboxy-2-thiophen-2-yl-ethylamino)-6-chloro-quinoline-3-carboxylic acid, and
optical isomers, polymorphs, analogs, derivatives, prodrugs, and pharmaceutically-acceptable acid and base addition salts, hydrates, and solvates thereof.

Moreover, the invention relates to a compound of Formula I as defined above, or an optical isomer, polymorph, analog, derivative, prodrug, pharmaceutically-acceptable acid or base addition salt, hydrate, or solvate thereof for the treatment or prevention of a condition associated with excitotoxicity and malfunctioning of glutamatergic neurotransmission, including for the conditions selected from those described earlier in the description.

Such conditions include pain, including acute pain, chronic pain, allodynia, hyperalgesia, visceral pain, phantom pain, post-operative pain, neuropathic pain, peripheral neuropathy including, for example peripheral neuropathy induced by nociception, inflammation, ischemia, viral infection (HZV), traumatic and other mechanical nerve injury, cancer, diabetes mellitus, HIV infection, fibromyalgia, trigeminus neuralgia, inflammatory bowel diseases (IBD), irritative bowel syndrome (IBS), arthritis including rheumatoid arthritis, osteoarthritis (degenerative joint disease), multiple sclerosis (MS) and gout (metabolic arthritis).

Such conditions also include acute insults, including cerebral ischemia, cerebral infarct, brain oedema, anoxia, inner ear insult, inner ear insult in tinnitus, head or brain or spinal cord trauma, head or brain or spinal cord injuries, trauma, sound- or drug-induced inner ear insult, ischaemia resulting from cardiac arrest or stroke or bypass operations or transplants, acute pain, hypoxia, perinatal hypoxia, and ischaemia; chronic insults, such as neurodegenerative disorders, including Morbus Huntington, Alzheimer's disease Creutzfeld-Jakob's syndrome/disease, bovine spongiform encephalopathy (BSE) prion related infections, diseases involving mitochondrial dysfunction, diseases involving β-amyloid and/or tauopathy, Down's syndrome, motor neuron diseases, amyotrophic lateral sclerosis (ALS), olivoponto-cerebellar atrophy, Parkinson's disease, Neuronal Ceroid Lipofuscinosis, AIDS dementia complex, AIDS-related dementia, dementia related to HIV infections, HIV-1 encephalopathy, AIDS encephalopathy, Korsakoff syndrome, vascular dementia, and corticobasal degeneration;

neurological disorders, including tinnitus, hearing loss, sound- or drug-induced tinnitus, haloperidol-induced dyskinesias, dopaminomimetic-induced dyskinesias, chorea, Huntington's chorea, athetosis, dystonia, stereotypy, ballism, tardive dyskinesias, tic disorder, spasmodic torticollis, blepharospasm, focal and generalized dystonia, nystagmus, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, L-dopa-induced dykinesias, L-dopa-induced dykinesias in Parkinson's disease therapy, dyskinesias, dyskinesia in Huntington's disease, drug induced dyskinesias, neuroleptic-induced dyskinesias, neurodegenerative cerebellar ataxias, centrally induced neuropathic pain, convulsions, epileptic convulsions, epilepsy, temporal lobe epilepsy, myoclonic epilepsy, tremor, dementia in Alzheimer's disease, dementia in Korsakoff syndrome, dementia, hereditary cerebellar ataxias, sleep disorders, movement disorders, essential tremor, muscle spasms, and spasticity;

psychological/psychiatric disorders, including generalized anxiety disorder, obsessive-compulsive disorder, panic disorder, posttraumatic stress disorder, social phobia, phobic disorders, substance-induced anxiety disorder, delusional disorder, schizoaffective disorder, schizophreniform disorder, substance-induced psychotic disorder, delirium, post-operative cognitive deficit (POCD), cognitive impairment, learning impairment, anxiety disorders, panic disorders, anxiety and panic disorders, social anxiety disorder (SAD), attention deficit hyperactivity disorder (ADHD), attention deficit syndrome (ADS), dementia, posttraumatic stress disorder (PTSD), schizophrenia, positive or cognitive or negative symptoms of schizophrenia, major depressive disorder, major depression, depression, bipolar manic-depressive disorder, sleep disorders, agoraphobia, bulimia nervosa, eating disorders, obesity, obesity-related-disorders, obesity abuse, food addiction, binge eating disorders, and hyperactivity in children;

drug/alcohol abuse, including craving (e.g., for drugs of abuse), abuse, addiction, nicotine addiction, nicotine abuse, alcohol addiction, alcohol abuse, opiate addiction, opiate abuse, cocaine addiction, cocaine abuse, amphetamine addiction, and amphetamine abuse;

skin diseases, including atopic dermatitis, itching, skin lesions induced by severe itching or atopic dermatitis, systemic sclerosis, pruritic conditions, and pruritis;

diseases of the gastro-intestinal tract and metabolic diseases including diarrhoea, hepatic encephalopathy, hypoglycaemia, gastroesophageal reflux disease (GERD), gastrointestinal dysfunction, lower esophageal sphincter (LES) disease, functional gastrointestinal disorders, dyspepsia, vomiting, urinary incontinence, and regurgitation;

diseases of the immune system, including Sjogren's syndrome, systemic lupus erythematosus, and multiple sclerosis (MS);

eye diseases, including eye injuries, eye diseases, eye disorders, glaucoma, retinopathy, and macular degeneration;

diseases of the respiratory tract, including respiratory tract infection, chronic laryngitis, asthma, reflux-related asthma, and lung disease;

migraine; autism; restless leg syndrome (RLS); Tourette syndrome; micturition disorders; neuromuscular disorder in the lower urinary tract; and drug tolerance to opioids.

Further, the invention relates to a compound of Formula I as defined above, or an optical isomer, polymorph, analog, derivative, prodrug, pharmaceutically-acceptable acid or base addition salt, hydrate, or solvate thereof for use in the treatment or prevention of NMDA excitotoxicity or malfunctioning glutamatergic neurotransmission.

Further, the invention relates to the use of a compound of Formula I as defined above or an optical isomer, polymorph, analog, derivative, prodrug, pharmaceutically-acceptable acid or base addition salt, hydrate, or solvate thereof for the manufacture of a medicament for the prevention and/or treatment of a condition associated with excitotoxicity and malfunctioning of glutamatergic neurotransmission. Such a use includes the use of such a compound for the manufacture of a medicament for the prevention and/or treatment of a condition in an animal including a human being which condition is associated with excitotoxicity and malfunctioning of glutamatergic neurotransmission, including conditions selected from those described earlier in the description.

Moreover, the invention relates to a method for treating or preventing a condition associated with excitotoxicity and malfunctioning of glutamatergic neurotransmission, including conditions selected from those described earlier in the description, such method comprising administering to a living animal, including a human, a therapeutically effective amount of a compound selected from those of Formula I as defined above or an optical isomer, polymorph, analog, derivative, prodrug, pharmaceutically-acceptable acid or base addition salt, hydrate, or solvate thereof.

A further aspect of the invention relates to such a method wherein the compound is administered in the form of a pharmaceutical composition thereof comprising at least one compound of Formula I in combination with one or more pharmaceutically-acceptable diluents, excipients, or carriers.

The compounds of the invention are suitable for administration in monotherapy or for combination therapy with other pharmaceutically active compounds. Examples of suitable other pharmaceutically active compounds include immunomodulators and agents active against central nervous system disorders such as other NMDA agonists or antagonists including glycine B antagonists.

Further, the invention relates to a pharmaceutical composition comprising as active ingredient at least one compound of Formula I as defined above, or an optical isomer, polymorph, analog, derivative, prodrug, pharmaceutically-acceptable acid or base addition salt, hydrate, or solvate thereof, together with one or more pharmaceutically acceptable excipients or vehicles.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, (i.e., methyl, ethyl, propyl, and isopropyl), straight and branched forms thereof.

As used herein and as far as it is not defined in a different manner elsewhere in this description or the accompanied claims, the term "$C_{1-6}$alkyl" represents straight or branched chain alkyl groups having 1, 2, 3, 4, 5 or 6 carbon atoms, examples of such alkyl groups include methyl, ethyl, n-propyl, 2-propyl, n-butyl, 2-butyl, iso-butyl, tert-butyl, n-pentyl, 2-pentyl, 3-pentyl, iso-pentyl, 2-methylbutyl, tert-amyl, n-hexyl, 2-hexyl, 3-hexyl, 1-methylpentyl, 2-methylpentyl, 3-methylpentyl, 4-methylpentyl, 2-dimethylbutyl, 3-dimethylbutyl, 2-ethylbutyl, and 3-ethylbutyl. Further, such alkyl groups may optionally be substituted by one or more fluorine, chlorine and/or bromine atoms and/or a carboxy or carbamoyl moiety; examples of halogenated alkyl moieties include —$CF_3$, —$CBr_3$, and —$CCl_3$. The term "$C_{2-6}$alkenyl" represents straight or branched chain alkenyl groups having 2, 3, 4, 5 or 6 carbon atoms. The term "cyclo$C_{3-12}$alkyl" represents monocyclic or bicyclic, or tricyclic alkyl groups having 3, 4, 5, 6, 7, 8, 9, 10, 11 or 12 carbon atoms, including cyclopropyl, cyclobutyl, cyclopentyl, cyclohexyl, bicyclo[2.2.1]heptyl and adamantanyl, wherein the "cyclo$C_{3-12}$alkyl"-ring is optionally substituted by one or more (e.g., 1, 2, 3, or 4) fluorine, chlorine, and/or bromine atoms. In the context of the present invention the term "di-($C_{1-6}$alkyl)amino" refers to an amino moiety in which the nitrogen atom of the amino group is substituted with two $C_{1-6}$alkyl groups, which may be the same or different, as defined above. Examples of di-$C_{1-6}$alkylamino groups include dimethylamino, diethylamino and N-methyl-N-isopropylamino. The term "aryl" represents phenyl or naphthyl, wherein the phenyl or naphthyl group is optionally substituted by one or more (e.g., 1, 2, 3, or 4) substituents, which may be the same or different, selected independently from a halogen, amino, hydroxy, nitro, cyano, COOH, $COOR^4$, $CONH_2$, $CONHR^5$, $CONR^5R^6$, $CH_2OH$, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo-$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, heteroaryl-$C_{1-6}$alkylamino, hydroxy-$C_{1-6}$alkylamino, carboxy-$C_{1-6}$alkylamino, $C_{1-6}$alkylamino-$C_{1-6}$alkyl, di-($C_{1-6}$alkyl)amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$alkoxy, di-($C_{1-6}$alkyl)amino-$C_{1-6}$alkoxy, carboxy-$C_{1-6}$alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkyl-aminosulfonyl, di-($C_{1-6}$alkyl)aminosulfonyl, arylaminosulfonyl, heteroarylaminosulfonyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$alkylaminocarbonyl-$C_{1-6}$alkyl, carboxy-$C_{1-6}$alkylaminocarbonyl-$C_{1-6}$ alkyl, di-($C_{1-6}$alkyl)aminocarbonyl-$C_{1-6}$alkyl, aryl$C_{2-6}$alkynyl, and heteroaryl$C_{2-6}$alkynyl. The term "heteroaryl" represents an aromatic 5-6 membered ring comprising one to four heteroatoms selected from oxygen, sulfur and nitrogen or a bicyclic ring system having one 5-6 membered ring comprising one to four heteroatoms selected from oxygen, sulfur and nitrogen fused with a benzene ring or a 5-6 membered ring comprising one to four heteroatoms selected from oxygen, sulfur and nitrogen, wherein the heteroaryl is optionally substituted by one or more (e.g., 1, 2, 3, or 4) substituents, which may be the same or different, selected independently from halogen, amino, hydroxy, nitro, cyano, COOH, $COOR^4$, $CONH_2$, $CONHR^5$, $CONR^5R^6$, CH2OH, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$alkylamino, hydroxy-$C_{1-6}$alkylamino, carboxy-$C_{1-6}$alkylamino, $C_{1-6}$alkylamino-$C_{1-6}$alkyl, di-($C_{1-6}$alkyl)amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$alkoxy, di-($C_{1-6}$alkyl)amino-$C_{1-6}$alkoxy, carboxy-$C_{1-6}$alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkylaminosulfonyl, di-($C_{1-6}$alkyl)aminosulfonyl, arylaminosulfonyl, heteroarylaminosulfonyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$ alkyl, heteroarylaminocarbonyl-$C_{1-6}$alkyl, hydroxy-$C_{1-6}$alkylaminocarbonyl-$C_{1-6}$alkyl, carboxy-$C_{1-6}$alkylaminocarbonyl-$C_{1-6}$alkyl, and di-($C_{1-6}$alkyl)aminocarbonyl-$C_{1-6}$alkyl; examples of such heteroaryl groups include furyl, thienyl, pyrrolyl, oxazolyl, isoxazolyl, thiazolyl, imidazolyl, pyrazolyl, oxadiazolyl, thiadiazolyl, tetrazolyl, pyridinyl, pyrimidinyl, pyrazinyl, pyridazinyl, benzofuryl, benzothienyl, indolyl, benzimidazolyl, benzoxazolyl, benzothiazolyl, quinolinyl, isoquinolinyl, quinazolinyl, quinoxalinyl. The term "acyl" represents $C_{1-6}$alkylcarbonyl, $C_{2-6}$alkenylcarbonyl, $C_{2-6}$alkynylcarbonyl, hydroxy-$C_{1-6}$alkylcarbonyl, carboxy-$C_{1-6}$alkylcarbonyl, $C_{1-6}$alkoxy-$C_{1-6}$alkylcarbonyl, arylcarbonyl, heteroarylcarbonyl, cyclo-$C_{3-12}$alkylcarbonyl, cyclo-$C_{3-12}$alkyl-$C_{1-6}$alkylcarbonyl, cyclo-$C_{3-12}$alkoxy-$C_{1-6}$alkylcarbonyl, aryloxy-$C_{1-6}$alkylcarbonyl, heteroaryloxy-$C_{1-6}$alkylcarbonyl, aryl-$C_{1-6}$alkylcarbonyl, heteroaryl-$C_{1-6}$alkylcarbonyl, cyclo-$C_{3-12}$alkyl-$C_{1-6}$alkylcarbonyl, aryl-$C_{1-6}$alkoxycarbonyl, heteroaryl-$C_{1-6}$alkoxycarbonyl, arylamino-$C_{1-6}$alkylcarbonyl, heteroarylamino-$C_{1-6}$alkylcarbonyl, cyclo-$C_{3-12}$alkylamino-$C_{1-6}$alkylcarbonyl, carboxy-$C_{1-6}$alkylamino-$C_{1-6}$alkylcarbonyl, arylsulfonylamino-$C_{1-6}$alkylcarbonyl, $C_{1-6}$alkylsulfonylamino-$C_{1-6}$alkylcarbonyl, and heterocyclylcarbonyl. The term "heterocyclyl" represents saturated 4-7 membered heterocycle containing one or two heteroatoms selected from oxygen, sulfur and nitrogen, examples of such heterocyclyl groups include azetidinyl, pyrrolidinyl, piperidinyl, azepanyl, tetrahydrofuryl, thiazolidinyl, morpholinyl, thiomorpholinyl, piperazinyl. The term "halogen" represents fluorine, chlorine, bromine and iodine.

The compounds of the present invention are named according to the IUPAC or CAS nomenclature system. Abbreviations which are well known to one of ordinary skill in the art may be used (e.g. "Ph" for phenyl, "Me" for methyl, "Et" for ethyl, "h" for hour or hours, and "rt" for room temperature).

The term "analog" or "derivative" is used herein in the conventional pharmaceutical sense, to refer to a molecule that structurally resembles a reference molecule, but has been modified in a targeted and controlled manner to replace one or more specific substituents of the reference molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, fewer side effects, etc.) is a drug design approach that is well known in pharmaceutical chemistry.

In addition, using methods known to those skilled in the art, analogs and derivatives of the compounds of the invention can be created which have improved therapeutic efficacy in controlling CNS diseases, i.e., higher potency and/or selectivity at a specific targeted receptor type, either greater or lower ability to penetrate mammalian blood-brain barriers (e.g., either higher or lower blood-brain barrier permeation rate), fewer side effects, etc.

The term "prodrug" is used herein in the conventional pharmaceutical sense, to refer to a molecule which undergoes a transformation in vivo (e.g., an enzymatic or chemical transformation) to release an active parent drug. Prodrugs of the compounds of Formula I of the present invention may be prepared by chemically modifying a functional group present in the compound of Formula I such that the chemically modified compound may undergo a transformation in vivo (e.g., enzymatic hydrolysis) to provide the compound of Formula I. Examples of functional groups present in the compounds of Formula I which may be modified to produce prodrugs include carboxy, hydroxy, amino, and thio groups. For example, a carboxy group may be modified to form an optionally substituted alkyl ester (e.g., wherein the alkyl moiety is optionally substituted by one or more groups such as alkoxy, dialkylamino); a hydroxy group may be modified to form an optionally substituted alkyl ether; an amino group may be modified to form an amide; and a thio group may be modified to form an optionally substituted alkylthio ether. Prodrugs of the compounds of Formula I of the present invention may be prepared according to conventional techniques which have been described in the art (see, for example, Stella V., et al., *Prodrugs: Challenges and Rewards*, AAPS Press/Springer, New York, 2007).

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

Compounds of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt or isomer is not critical, provided that it is non-toxic and does not substantially interfere with the desired pharmacological activity.

It will be appreciated by those skilled in the art that compounds of the invention having a chiral center may exist in and be isolated in optically active and racemic forms. Some compounds may exhibit polymorphism. It is to be understood that the present invention ecompasses any racemic, optically-active, polymorphic, tautomeric, or stereoisomeric form, or mixture thereof, of a compound of the invention, which possesses the useful properties described herein.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by selective crystallization of their diastereomeric salts with optically active acids. Alternatively, enantiomers may be separated by chromatographic techniques using chiral stationary phases. Pure stereoisomeric forms may also be derived from the corresponding pure stereoisomeric form of appropriate starting materials, provided that the reaction occurs stereoselectively. Stereoisomeric forms of Formula I are obviously intended to be included within the scope of this invention.

Addition Salts

For therapeutic use, salts of the compounds of Formula I are those wherein the counterion is pharmaceutically acceptable. However, salts of acids and bases, which are non-pharmaceutically acceptable, may also find use, for example, in the preparation and purification of pharmaceutically acceptable compounds. All salts whether pharmaceutically acceptable or not are included within the ambit of the present invention. The pharmaceutically acceptable salts as mentioned above are meant to comprise the therapeutically active non-toxic salt forms, which the compounds of Formula I are able to form. The latter can conveniently be obtained by treating the base form with such appropriate acids as inorganic acids, e.g. hydrohalic acids such as hydrochloric, hydrobromic and the like; sulfuric acid; nitric acid; phosphoric acid and the like; or organic acids such as acetic, propanoic, hydroxyacetic, 2-hydroxypropanoic, oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic and like acids. Conversely, the salt may be converted to the free base by treatment with alkali.

Pharmaceutical Compositions

The active ingredients of the compounds of the present invention, together with one or more conventional adjuvants, carriers, or diluents, may be placed into the form of pharmaceutical compositions and unit dosages thereof, and in such form may be employed as solids, such as coated or uncoated tablets or filled capsules, liquids, such as solutions, suspensions, emulsions, elixirs, or capsules filled with the same, or thin films/flash doses, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient of the compounds of the present invention commensurate with the intended daily dosage range to be employed. Tablets containing one (1) to one hundred (100) milligrams of active ingredient or, more broadly, zero point five (0.5) to five hundred (500) milligrams per tablet, are accordingly suitable representative unit dosage forms.

The term "excipient" applied to pharmaceutical compositions of the invention refers to an adjuvant, carrier, diluent, or vehicle with which a compound of the present invention is administered. Such pharmaceutical excipients may be sterile or non-sterile excipients commonly used for the formulation and production of solid, semi solid, liquid and sterile pharmaceutical compositions. These excipients may also be liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. A. R. Gennaro, $20^{th}$ Edition, describes suitable pharmaceutical carriers in "Remington: The Science and Practice of Pharmacy". The excipients may also be combinations of solids and liquids.

Method of Treating

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, including concurrently, simultaneously, or together with one or more pharmaceutically-acceptable excipients, carriers, or diluents, including in the form of a pharmaceutical composition thereof, whether by oral, rectal, or parental (including intravenous and subcutaneous) or in some cases even topical route, in an effective amount. Suitable dosage ranges are 1-1000 milligrams daily, optionally 10-500 milligrams daily, and optionally 50-500 milligrams daily, depending as usual upon the exact mode of administration, form in which administered, the indication toward which the administration is directed, the subject involved and the body weight of the subject involved, and the preference and experience of the physician or veterinarian in charge.

The term "treat" is used herein to mean to relieve or, alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a living animal body in need thereof.

The compounds of the present invention may be administered orally, topically, parenterally, or mucosally (e.g., buccally, by inhalation, or rectally) in dosage unit formulations containing conventional non-toxic pharmaceutically acceptable carriers. It is usually desirable to use the oral route. The compounds of the present invention may be administered orally in the form of a capsule, a tablet, or the like (see Remington: The Science and Practice of Pharmacy, 20$^{th}$ Edition). The orally administered medicaments may be administered in the form of a time-controlled release vehicle, including diffusion-controlled systems, osmotic devices, dissolution-controlled matrices, and erodible/degradable matrices.

For oral administration in the form of a tablet or capsule, the glycine B antagonist active component may be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like. For oral administration in liquid form, the glycine B antagonist active components may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms.

The tablets may be coated by methods well known in the art. The compounds of the present invention may be also introduced in beads, microspheres or microcapsules, e.g., fabricated from polyglycolic acid/lactic acid (PGLA). Liquid preparations for oral administration may take the form of, for example, solutions, syrups, emulsions or suspensions, or they may be presented as a dry product for reconstitution with water or other suitable vehicle before use. Preparations for oral administration may be suitably formulated to give controlled or postponed release of the active compound.

The compounds of the present invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

The compounds of the present invention may also be delivered by the use of monoclonal antibodies as individual carriers to which the compound molecules are coupled. The instant compounds may also be coupled with soluble polymers as targetable drug carriers. Such polymers include polyvinyl-pyrrolidone, pyran copolymer, polyhydroxy-propyl methacrylamide-phenol, polyhydroxy-ethyl-aspartamidephenol, or polyethyleneoxide-polylysine substituted with palmitoyl residues. Furthermore, the instant compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the compounds of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, e.g., gelatin for use in an inhaler or insufflator can be formulated containing a powder mix of the compound and a suitable powder base such as lactose or starch.

The formulations comprising the compounds of the present invention may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient of the compounds of the present invention can be in powder form for reconstitution with a suitable vehicle, e.g., sterile pyrogen-free water, before use.

The compounds of the present invention may also be formulated for rectal administration, e.g., as suppositories or retention enemas (e.g., containing conventional suppository bases such as cocoa butter or other glycerides).

The compositions comprising glycine B antagonists of the present invention may, if desired, be presented in a pack or dispenser device, which may contain one or more unit dosage forms containing the active ingredient and/or may contain different dosage levels to facilitate dosage titration. The pack may, for example, comprise metal or plastic foil, such as a blister pack. The pack or dispenser device may be accompanied by instructions for administration. The glycine B antagonists of the present invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. Compositions that exhibit large therapeutic indices are preferred.

Scheme I describes the preparation of compounds of Formula I of the present invention. All of the starting materials are prepared by procedures described in these schemes, by procedures well known to one of ordinary skill in organic chemistry or can be obtained commercially. All of the final compounds of the present invention are prepared by procedures described in these charts or by procedures analogous thereto, which procedures would be well known to one of ordinary skill in organic chemistry. All of the variables used in the schemes are as defined below or as in the claims.

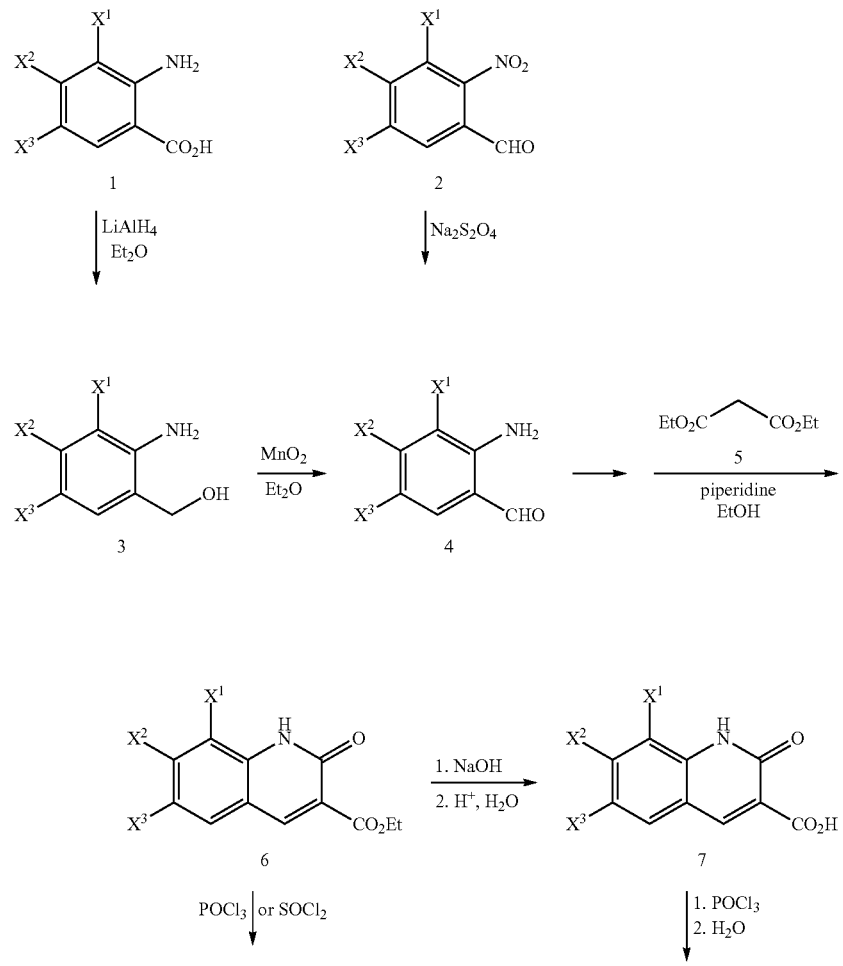

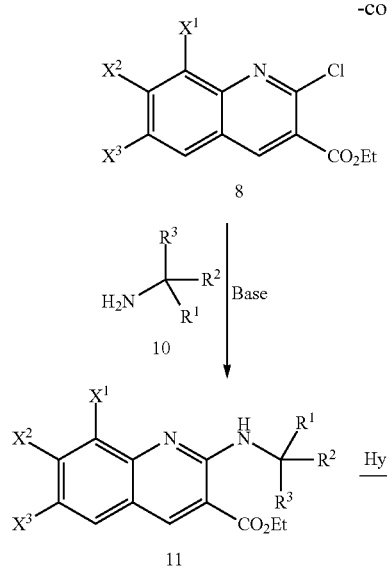
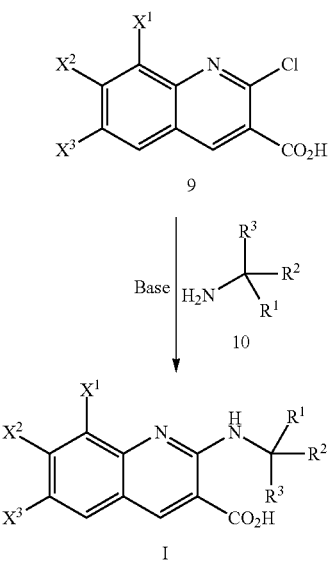

Compounds of the present invention may be prepared in two steps by arylation of amines 10 with esters of 2-chloroquinoline-3-carboxylic acids 8 to give esters of 2-(substituted)-aminoquinoline-3-carboxylic acids 11 which in turn are hydrolyzed by an appropriate aqueous inorganic base or mineral acid. Hydrolysis with inorganic base may give a salt of acid I. This may be, for example, a sodium salt if hydrolysis is performed with base such as sodium hydroxide. Alternatively, compounds of formula I may be obtained by direct arylation of amines 10 with 2-chloroquinoline-3-carboxylic acids 9. The amines 10 are commercially available or may be prepared according to well known literature procedures.

2-Chloroquinolines 8 and 9 are prepared by common synthetic procedures starting from corresponding quinoline-2-ones 6 and 7, respectively, by heating them with phosphorus oxychloride as shown in Scheme I, or, alternatively, by heating with thionyl chloride. Necessary esters of 2-oxo-1,2-dihydro-quinoline-3-carboxylic acid 6 are synthesized via a condensation reaction of 2-amino-benzaldehydes 4 with lower dialkyl malonates (e.g., diethyl malonate) in the presence of piperidine. In turn, 2-amino-benzaldehydes 4 may be prepared from an appropriate nitrobenzaldehyde 2 by reduction of the nitro group with sodium dithionite or by oxidation of the corresponding (2-amino-phenyl)-methanol 3 with, for example, manganese (IV) oxide.

It will be appreciated that in the above transformations it may be necessary or desirable to protect any sensitive groups in the molecule of the compound in question in order to avoid undesirable side reactions. The reaction products may be isolated and purified by standard laboratory techniques, such as extraction, chromatography and crystallization. Products isolated as a free base may be further converted into a hydrochloride or any other pharmaceutically acceptable salt according to known procedures. Products isolated as a free carboxylic acid may be converted into sodium salt or any other pharmaceutically acceptable salt according to known procedures.

It will be apparent to those skilled in the art that the described synthetic procedures are merely representative in nature and that alternative synthetic processes are known to one of ordinary skill in organic chemistry.

EXPERIMENTAL PART

The compounds and their preparation of the present invention will be better understood in connection with the following examples, which are intended as an illustration of and not a limitation upon the scope of the invention.

Hereinafter, "DMF" is defined as N,N-dimethylformamide, "HCl" as hydrochloric acid, "DMSO" as dimethyl sulfoxide, "NH$_4$OH" as ammonium hydroxide solution, "MeCN" as acetonitrile, "AcOH" as acetic acid, "EtOH" as ethanol, "MeOH" as methanol and SiO$_2$ as silica gel.

Synthesis of Starting Materials

Preparation of (2-amino-phenyl)-methanols (2) by reduction of 2-amino-benzoic acids (3)—General procedure 2-Amino-benzoic acid (14 mmol) in dry diethyl ether (15 mL) is added dropwise to an ice cooled solution of lithium aluminum hydride (15 mmol) in dry diethyl ether (100 mL) and stirred at room temperature for 2 h. Water (8 ml) is added dropwise, followed by 1M aqueous sodium hydroxide solution (13 mL). The organic layer is collected, dried over sodium sulfate and concentrated under reduced pressure. The crude product is used in the next step without further purification.

(2-Amino-5-chloro-phenyl)-methanol

Yield 88%; $^1$H NMR (DMSO): 4.31 (d, 5 Hz, 2H); 5.01 (br s, 2H); 5.11 (t, 5 Hz, 1H); 6.58 (d, 9 Hz, 1H); 6.94 (dd, 9 and 2 Hz, 1H) and 7.07 (d, 2 Hz, 1H).

(2-Amino-3,5-dichloro-phenyl)-methanol

Yield 98%; $^1$H NMR (DMSO): 4.38 (d, 5 Hz, 2H); 5.22 (br s, 2H); 5.33 (t, 5 Hz, 1H); 7.12 and 7.23 (both d, 3 Hz, both 1H).

(2-Amino-5-bromo-phenyl)-methanol

Yield 89%; $^1$H NMR (DMSO): 4.31 (d, 6 Hz, 2H); 5.04 (br s, 2H); 5.10 (t, 6 Hz, 1H); 6.54 (d, 8 Hz, 1H); 7.05 (dd, 8 and 2 Hz, 1H) and 7.18 (d, 3 Hz, 1H).

Oxidation of (2-amino-phenyl)-methanols (3) to 2-amino-benzaldehydes (4)—General procedure (2-Amino-phenyl)-methanol (12 mmol) in dry diethyl ether (25 mL) is added dropwise to a mixture of manganese dioxide (48 mmol) in dry diethyl ether (25 mL) and the mixture is stirred at rt overnight. The solution is filtered through a celite and the solvent is removed at reduced pressure. The crude product is used in the next step without further purification.

2-Amino-5-chloro-benzaldehyde

Yield 99%; $^1$H NMR (CDCl$_3$): 6.14 (br s, 2H); 6.61 (d, 9 Hz, 1H); 7.25 (dd, 9 and 2 Hz, 1H); 7.44 (d, 2 Hz, 1H) and 9.80 (s, 1H).

2-Amino-3,5-dichloro-benzaldehyde

Yield 93%; $^1$H NMR (DMSO): 7.26 (br s); 7.68 and 7.74 (both d, both 2 Hz, both 1H) and 9.83 (s, 1H).

2-Amino-5-bromo-benzaldehyde

Yield 87%; $^1$H NMR (DMSO): 6.72 (d, 9 Hz, 1H); 7.22 (br s, 2H); 7.39 (dd, 9 and 2 Hz, 1H); 7.72 (d, 2 Hz, 1H) and 9.76 (s, 1H).

General procedure for the preparation of 2-oxo-1,2-dihydro-quinoline-3-carboxylic acid ethyl esters (6)

To a solution of 2-amino-benzaldehyde (10 mmol) in EtOH (15 mL) is added diethyl malonate (14 mmol) and piperidine (0.01 mmol), and the mixture is stirred under reflux for 20 h. After cooling to rt, the solid is filtered, washed with cold ethanol and dried.

2-Oxo-1,2-dihydro-quinoline-3-carboxylic acid ethyl ester

Yield 34%.

6-Chloro-2-oxo-1,2-dihydro-quinoline-3-carboxylic acid ethyl ester

Yield 70%; $^1$H NMR (DMSO): 1.28 (t, 3H); 4.26 (q, 2H); 7.33 (d; 9 Hz, 1H); 7.62 (dd, 9 and 2 Hz, 1H); 7.94 (d, 2 Hz, 1H); 8.44 (s, 1H) and 8.93 (s, 1H).

6,8-Dichloro-2-oxo-1,2-dihydro-quinoline-3-carboxylic acid ethyl ester

Yield 72%; $^1$H NMR (DMSO): 1.29 (t, 3H); 4.28 (q, 2H); 7.91 and 7.97 (both d; both 3 Hz); 8.47 (s, 1H) and 11.52 (s, 1H).

6,7-Dichloro-2-oxo-1,2-dihydro-quinoline-3-carboxylic acid ethyl ester

Prepared from 2-amino-4,5-dichloro-benzaldehyde [Cordi A. A., Desos P, Randle J. C. R., Lepagnol *J. Bioorg. Med. Chem.* 1995, 3 (2), 129.] Yield 33%.

6-Bromo-2-oxo-1,2-dihydro-quinoline-3-carboxylic acid ethyl ester

Yield 72%; $^1$H NMR (DMSO): 1.28 (t, 3H); 4.25 (q, 2H); 7.25 (d; 9 Hz, 1H); 7.73 (dd, 9 and 2 Hz, 1H); 8.07 (d, 2 Hz, 1H); 8.43 (s, 1H) and 12.15 (s, 1H).

6,8-Dibromo-2-oxo-1,2-dihydro-quinoline-3-carboxylic acid ethyl ester

Prepared from 2-amino-3,5-dibromo-benzaldehyde [Dickson N. J., Dyall L. K. *Austr. J. Chem.* 1980, 33 (1) 91.] Yield 81%; $^1$H NMR (DMSO): 1.28 (t, 3H); 4.27 (q, 2H); 8.12 and 8.13 (both d; both 3 Hz, both 1H); 8.46 (s, 1H) and 10.89 (br s, 1H).

6-Chloro-8-methyl-2-oxo-1,2-dihydro-quinoline-3-carboxylic acid ethyl ester

Prepared from 2-amino-3-methyl-5-chloro-benzaldehyde [Rybinov V. I., Mustafina M. Ya., Gorelic M. V. *Zhurnal Organicheskoi Khimii.* 1992, 28 (10), 2219.] Yield 76%; $^1$H NMR (DMSO): 1.30 (t, 3H); 2.43 (s, 3H); 4.28 (q; 2H); 7.53 (s; 1H); 7.81 (s, 1H); 8.44 (s, 1H); 11.33 (br s, 1H).

6-Bromo-8-methyl-2-oxo-1,2-dihydro-quinoline-3-carboxylic acid ethyl ester

Prepared from 2-amino-5-bromo-3-methyl-benzaldehyde [Rybinov V. I., Mustafina M. Ya., Gorelic M. V. *Zhurnal Organicheskoi Khimii.* 1992, 28 (10), 2219.] Yield 51%; $^1$H NMR (DMSO): 1.30 (t, 3H); 2.42 (s, 3H); 4.28 (q, 2H); 7.64 (s; 1H); 7.94 (s, 1H); 8.44 (s, 1H); 11.32 (br s, 1H).

General procedure for the preparation of 2-oxo-1,2-dihydro-quinoline-3-carboxylic acids (7)

A solution of 2-oxo-1,2-dihydro-quinoline-3-carboxylic acid ethyl ester (6) (0.5 mmol) in THF or EtOH (5 mL) and a solution of sodium hydroxide (5 mmol) in water (5 mL) is heated at reflux for 1 h. After cooling the reaction mixture is acidified by addition of 2N HCl, and the precipitated solid is collected on filter, washed with water and dried.

6-Chloro-2-oxo-1,2-dihydro-quinoline-3-carboxylic acid

Yield 69%; $^1$H NMR (DMSO): 7.47 (d, 1H); 7.77 (dd, 1H); 8.16 (d, 1H); 8.91 (s, 1H).

6-Bromo-2-oxo-1,2-dihydro-quinoline-3-carboxylic acid

Yield 82%; $^1$H NMR (DMSO): 7.42 (d, 1H); 7.89 (dd, 1H); 8.30 (d, 1H); 8.91 (s, 1H).

6,8-Dichloro-quinoline-3-carboxylic acid

Yield 90%; $^1$H NMR (DMSO): 8.02 (d, 1H); 8.14 (d, 1H); 8.85 (s, 1H).

6-Chloro-8-methyl-2-oxo-1,2-dihydro-quinoline-3-carboxylic acid

Yield 68%; ¹H NMR (DMSO): 7.67 (s, 1H); 8.02 (s, 1H); 8.91 (s, 1H); 12.43 (br s, 1H).

6-Bromo-8-methyl-2-oxo-1,2-dihydro-quinoline-3-carboxylic acid

Yield 80%; ¹H NMR (DMSO): 7.80 (s, 1H); 8.17 (s, 1H); 8.91 (s, 1H); 12.42 (br s, 1H); 14.60 (br s, 1H).

General procedure for the preparation of 2-chloro-quinoline-3-carboxylic acids (9) and ethyl esters (8)

A suspension of 2-oxo-1,2-dihydro-quinoline-3-carboxylic acid (7) or ethyl ester (8) (3 mmol) in phosphoryl chloride (10 ml) is heated at reflux for 4 h. The reaction mixture is cooled and slowly poured into a mixture of ice and water (200 mL). A white precipitate is collected by filtration, washed with water and dried.

2-Chloro-quinoline-3-carboxylic acid ethyl ester

Yield 83%.

2,6-Dichloro-quinoline-3-carboxylic acid ethyl ester

Yield 99%; mp 125-127° C.; ¹H NMR (DMSO): 1.35 (t, 3H); 4.39 (q, 2H); 7.94 (dd; 9 and 2 Hz, 1H); 8.03 (d, 9 Hz, 1H); 8.33 (d, 2 Hz, 1H) and 8.92 (s, 1H).

2,6,8-Trichloro-quinoline-3-carboxylic acid ethyl ester

Yield 99%; mp 147-149° C.; ¹H NMR (DMSO): 1.35 (t, 3H); 4.40 (q, 2H); 8.25 and 8.32 (both d, 2 Hz, both 1H) and 8.97 (s, 1H).

2,6,7-Trichloro-quinoline-3-carboxylic acid ethyl ester

Yield 95%.

6-Bromo-2-chloro-quinoline-3-carboxylic acid ethyl ester

Yield 98%; mp 129-130° C.; ¹H NMR (DMSO): 1.35 (t, 3H); 4.39 (q, 2H); 7.94 (d; 9 Hz, 1H); 8.05 (dd, 9 and 2 Hz, 1H); 8.48 (d, 2 Hz, 1H) and 8.91 (s, 1H).

6,8-Dibromo-2-chloro-quinoline-3-carboxylic acid ethyl ester

Yield 95%; mp 153-154° C.; ¹H NMR (DMSO): 1.39 (t, 3H); 4.40 (q, 2H); 8.48 and 8.51 (both d, 2 Hz, both 1H) and 8.95 (s, 1H).

2,6-Dichloro-8-methyl-quinoline-3-carboxylic acid ethyl ester

Yield 91%; ¹H NMR (DMSO): 1.37 (t, 3H); 2.67 (s, 3H); 4.41 (q, 2H); 7.88 (s, 1H); 8.17 (s, 1H); 8.90 (s, 1H).

2-Bromo-6-chloro-8-methyl-quinoline-3-carboxylic acid ethyl ester

Yield 98%; ¹H NMR (DMSO): 1.37 (t, 3H); 2.66 (s, 3H); 4.39 (q, 2H); 7.98 (s, 1H); 8.32 (s, 1H); 8.89 (s, 1H).

2,6-Dichloro-quinoline-3-carboxylic acid

Yield 54%; ¹H NMR (DMSO): 7.92 (dd; 1H); 8.03 (d, 1H); 8.32 (d, 1H) and 8.91 (s, 1H).

Determination of Enantiomeric Purity

Chiral compounds may be analyzed for enantiomeric purity using HPLC.

As a representative example, the substance obtained according to the procedure described in Example 1 (i.e., (2-((S)-1-Carboxy-2-phenyl-ethylamino)-6-chloro-quinoline-3-carboxylic acid, obtained using L-phenylalanine as a starting material) may be analyzed using the following chromatographical conditions:

Column: Chiralpak AD-H, 4.6×250 mm, 5 µm particle size; mobile phase:

Hexane:EtOH:TFA, 94:6:0.1. Flow rate 0.75 ml/min; Column temperature 25° C. Pressure 45 bar. Detection UV-254 nm.

Two peaks are registered with Rt 25.94 min (area 98.8%) and Rt 41.99 min (area 1.2%). Calculated enantiomeric excess ee 97.6%.

Analysis of racemic sample prepared from DL-phenylalanine according to the procedure described in Example 1 displayed the same separation.

Analysis of the sample enriched by (2%) substance obtained according to the procedure described in Example 6 (2-((R)-1-Carboxy-2-phenyl-ethylamino)-6-chloro-quinoline-3-carboxylic acid, obtained using D-phenylalanine as a starting material) resulted in an increase of peak with Rt 39.32 min.

Example 1

2-((S)-1-Carboxy-2-phenyl-ethylamino)-6-chloro-quinoline-3-carboxylic acid

A mixture of 2,6-dichloroquinoline-3-carboxylic acid (243 mg, 1 mmol), L-phenylalanine (330 mg, 2 mmol) and potassium carbonate (415 mg, 3 mmol) in water (3 mL) is stirred for 24 h at 135° C. in closed reaction vial. After cooling, the reaction mixture is acidified by addition of 2N HCl, and the precipitated solid is collected on filter, washed with water and recrystallized from DMF-water to give the title compound (211 mg, 57%) as yellow needles.

Mp 153-159° C.; ¹H-NMR (200 MHz, DMSO-d₆); δ (ppm) 3.05-3.30 (m, 2H), 4.89-4.99 (m, 1H); 7.23 (m, 5H); 7.46-7.70 (m, 2H); 7.94 (s, 1H); 8.69 (s, 1H); 8.87 (d, 1.7 Hz, 1H); LC MS m/z 371 (MH+).

Example 2

2-[1-Carboxy-2-(1H-indol-3-yl)-ethylamino]-6-chloro-quinoline-3-carboxylic acid In close analogy to the procedure described in Example 1, 2,6-dichloroquinoline-3-carboxylic acid is reacted with DL-tryptophan to provide the title compound in 42% yield as yellow needles (recrystallization from isopropanol).

Mp >140° C. (decomp.); ¹H-NMR (200 MHz, DMSO-d₆), δ (ppm) 3.20-3.39 (m, 2H); 4.93-5.01 (m, 1H); 6.89-7.32 (m, 5H); 7.46-7.60 (m, 2H); 7.94 (s, 1H); 8.68 (s, 1H); 8.92 (d, 7.0 Hz, 1H); 10.88 (s, 1H).

Example 3

2-(1-Carboxy-butylamino)-6-chloro-quinoline-3-carboxylic acid

In close analogy to the procedure described in Example 1, 2,6-dichloroquinoline-3-carboxylic acid is reacted with DL-2-aminopentanoic acid to provide the title compound in 15% yield as yellow needles (flash chromatography on $SiO_2$, eluent MeCN, $H_2O$, AcOH-20, 1, 0.3).

Mp >160° C. (decomp.); $^1$H-NMR (200 MHz, DMSO-$d_6$), δ (ppm) 0.78 (t, 6.9 Hz, 3H); 1.20-1.35 (m, 2H); 1.65-1.85 (m, 2H); 4.32-4.45 (m, 1H); 7.30-7.40 (m, 2H); 7.66 (s, 1H); 8.38 (s, 1H); 10.10 (d, 6.0 Hz, 1H).

Example 4

2-(Carboxymethyl-amino)-6-chloro-quinoline-3-carboxylic acid

In close analogy to the procedure described in Example 1, 2,6-dichloroquinoline-3-carboxylic acid is reacted with glycine to provide the title compound in 52% yield as yellow needles (recrystallization from EtOH/water).

Mp >215° C. (decomp.); $^1$H-NMR (200 MHz, DMSO-$d_6$), δ (ppm) 4.19 (s, 2H); 7.42-7.53 (m, 2H); 7.87 (s, 1H); 8.60 (s, 1H); 9.44 (br s, 1H).

Example 5

2-[(Carboxy-phenyl-methyl)-amino]-6-chloro-quinoline-3-carboxylic acid

In close analogy to the procedure described in Example 1, 2,6-dichloroquinoline-3-carboxylic acid is reacted with DL-phenylglycine to provide the title compound in 33% yield as yellow needles (recrystallization from DMF/water).

Mp >185° C. (decomp.); $^1$H-NMR (200 MHz, DMSO-$d_6$), δ (ppm) 5.73 (d, 6.8 Hz, 1H); 7.31-7.62 (m, 7H); 7.98 (s, 1H); 8.77 (s, 1H); 9.10 (d, 5.6 Hz, 1H).

Example 6

2-((R)-1-Carboxy-2-phenyl-ethylamino)-6-chloro-quinoline-3-carboxylic acid

In close analogy to the procedure described in Example 1, 2,6-dichloroquinoline-3-carboxylic acid is reacted with D-phenylalanine to provide the title compound in 45% yield as yellow needles (recrystallization from MeOH/water).

Mp 157-172° C. (decomp.); $^1$H-NMR (200 MHz, DMSO-$d_6$), δ (ppm) 3.06-3.30 (m, 2H); 4.95 (q, 6.3 Hz, 1H); 7.20-7.30 (m, 5H); 7.50 (d, 8.6 Hz, 1H); 7.60 (dd, 9.6, 1.8 Hz, 1H); 7.97 (d, 1.8 Hz, 1H); 8.53 (d, 5.8 Hz, 1H); 8.74 (s, 1H).

Example 7

6-Chloro-2-((R)-2-hydroxy-1-phenylethylamino)-quinoline-3-carboxylic acid

In close analogy to the procedure described in Example 1, 2,6-dichloroquinoline-3-carboxylic acid is reacted with D-phenylglycinol to provide the title compound in 23% yield as yellow needles (flash chromatography on $SiO_2$, eluent $CHCl_3$, MeOH, AcOH—15, 1, 0.2).

Mp 242-245° C. (decomp.); $^1$H-NMR (200 MHz, DMSO-$d_6$), δ (ppm) 3.68-3.82 (m, 2H); 5.38 (br s, 1H); 7.18-7.56 (m, 6H); 7.53 (d, 9.0 Hz, 1H); 7.93 (s, 1H); 8.73 (s, 1H); 8.92 (s, 1H).

Example 8

2-{(S)-1-Carboxy-2-[4-(3-carboxy-6-chloroquinolin-2-yloxy)-phenyl]-ethylamino}-6-chloro-quinoline-3-carboxylic acid In close analogy to the procedure described in Example 1, 2,6-dichloroquinoline-3-carboxylic acid is reacted with L-tyrosine to provide the title compound in 13% yield as yellow needles (flash chromatography on $SiO_2$, eluent $CHCl_3$, MeOH, AcOH—10, 1, 0.2).

Mp >250° C. (decomp.); $^1$H-NMR (200 MHz, DMSO-$d_6$), δ (ppm) 3.10-3.40 (m, 2H); 4.93 (br s, 1H); 7.07 (d, 7.8 Hz, 2H); 7.28 (d, 8.0 Hz, 2H); 7.49-7.64 (m, 4H); 7.85 (s, 1H); 8.13 (s, 1H); 8.61 (s, 1H); 8.67 (s, 1H); 9.53 (br s, 1H).

Example 9

2-[(S)-1-Carboxy-2-(4-nitro-phenyl)-ethylamino]-6-chloro-quinoline-3-carboxylic acid In close analogy to the procedure described in Example 1, 2,6-dichloroquinoline-3-carboxylic acid is reacted with 4-nitro-L-phenylalanine to provide the title compound in 61% yield as yellow needles (recrystallization from MeOH/water).

Mp 174-176° C.; $^1$H-NMR (200 MHz, DMSO-$d_6$), δ (ppm) 3.21-3.45 (m, 2H); 5.00 (br s, 1H); 7.45-7.54 (m, 4H); 7.88 (s, 1H); 8.10 (d, 8.6 Hz, 2H); 8.61 (s, 1H); 9.56 (br s, 1H).

Example 10

6-Chloro-2-((R)-1-hydroxymethyl-2-phenyl-ethylamino)-quinoline-3-carboxylic acid In close analogy to the procedure described in Example 1, 2,6-dichloroquinoline-3-carboxylic acid is reacted with D-phenylalaninol to provide the title compound in 22% yield as yellow needles (recrystallization from EtOH).

Mp 213-216° C.; $^1$H-NMR (200 MHz, DMSO-$d_6$), δ (ppm) 2.70-3.00 (m, 2H); 3.48 (d, 4.0 Hz, 2H); 4.42 (br s, 1H); 7.14-7.34 (m, 5H); 7.50-7.61 (m, 2H); 7.93 (s, 1H); 8.40 (br s, 1H); 8.70 (s, 1H).

Example 11

6-Chloro-2-((S)-2-hydroxy-1-phenyl-ethylamino)-quinoline-3-carboxylic acid

In close analogy to the procedure described in Example 1, 2,6-dichloroquinoline-3-carboxylic acid is reacted with L-phenylglycinol to provide the title compound in 31% yield as yellow needles (recrystallization from dioxane/water).

Mp 222-224° C.; $^1$H-NMR (200 MHz, DMSO-$d_6$), δ (ppm) 3.68-3.83 (m, 2H); 5.32-5.42 (m, 1H); 7.15-7.41 (m, 6H); 7.53 (dd, 8.8, 3.0 Hz, 1H); 7.93 (d, 3.0 Hz, 1H); 8.73 (s, 1H); 8.90 (br s, 1H).

Example 12

2-[(R)-1-Carboxy-2-(1H-indol-3-yl)-ethylamino]-6-chloro-quinoline-3-carboxylic acid In close analogy to the procedure described in Example 1, 2,6-dichloroquinoline-3-carboxylic acid is reacted with D-tryptophan to provide the title compound in 17% yield as yellow needles (flash chromatography on SiO$_2$, eluent MeCN, H$_2$O, AcOH—20, 1, 0.3).

Mp >250° C. (decomp.); $^1$H-NMR (200 MHz, DMS)-d$_6$), δ (ppm) 3.05-3.30 (m, 2H); 4.86 (br s, 1H); 6.92-7.06 (m, 2H); 7.18 (s, 1H); 7.30 (d, 7.6 Hz, 1H); 7.40 (s, 2H); 7.61 (d, 7.0 Hz, 1H); 7.75 (s, 1H); 8.42 (s, 1H); 10.60 (br s, 1H); 10.84 (br s, 1H).

Example 13

6-Chloro-2-((S)-1-hydroxymethyl-2-phenyl-ethylamino)-quinoline-3-carboxylic acid In close analogy to the procedure described in Example 1, 2,6-dichloroquinoline-3-carboxylic acid is reacted with L-phenylananinol to provide the title compound in 35% yield as yellow needles (recrystallization from acetone/CHCl$_3$).

Mp 213-216° C.; $^1$H-NMR (200 MHz, DMSO-d$_6$), δ (ppm) 2.72-3.00 (m, 2H); 3.48 (d, 4.4 Hz, 2H); 4.42 (br s, 1H); 7.15-7.34 (m, 5H); 7.50-7.61 (m, 2H); 7.93 (s, 1H); 8.39 (br s, 1H); 8.70 (s, 1H).

Example 14

6-Chloro-2-[(S)-1-hydroxymethyl-2-(1H-indol-3-yl)-ethylamino]-quinoline-3-carboxylic acid In close analogy to the procedure described in Example 1, 2,6-dichloroquinoline-3-carboxylic acid is reacted with L-tryptophanol to provide the title compound in 73% yield as yellow needles (recrystallization from EtOH).

Mp 213-217° C. (decomp.); $^1$H-NMR (200 MHz, DMSO-d$_6$), δ (ppm) 2.90-3.10 (m, 2H); 3.48-3.54 (m, 2H); 4.50 (br s, 1H); 7.00-7.16 (m, 3H); 7.31 (d, 8.0 Hz, 1H); 7.56-7.66 (m, 2H); 7.90-7.95 (m, 2H); 8.50 (br s, 1H); 8.73 (s, 1H); 10.79 (s, 1H).

Example 15

2-[(S)-1-Carboxy-2-(1-methyl-1H-indol-3-yl)-ethylamino]-6-chloro-quinoline-3-carboxylic acid In close analogy to the procedure described in Example 1, 2,6-dichloroquinoline-3-carboxylic acid is reacted with 1-methyl-L-tryptophan to provide the title compound in 21% yield as yellow needles (recrystallization from DMF/water).

Mp 185-191° C.; $^1$H-NMR (200 MHz, DMSO-d$_6$), δ (ppm) 3.00-3.40 (m, 2H); 3.70 (s, 3H); 4.90-5.10 (m, 1H); 6.92-7.14 (m, 3H); 7.35 (d, 8.2 Hz, 1H); 7.48-7.63 (m, 3H); 7.97 (s, 1H); 8.52 (d, 6.4 Hz, 1H); 8.74 (s, 1H).

Example 16

2-((S)-5-Benzyloxycarbonylamino-1-carboxy-pentylamino)-6-chloro-quinoline-3-carboxylic acid In close analogy to the procedure described in Example 1, 2,6-dichloroquinoline-3-carboxylic acid is reacted with N$_{(ε)}$-Cbz-L-lysine to provide the title compound in 43% yield as yellow needles (recrystallization from EtOH/water).

Mp 152-154° C.; $^1$H-NMR (200 MHz, DMSO-d$_6$), δ (ppm) 1.41 (br s, 4H); 1.75-1.95 (m, 2H); 2.95-3.05 (m, 2H); 4.65-4.78 (m, 1H); 4.96 (s, 2H); 7.25-7.40 (m, 6H); 7.46-7.62 (m, 2H); 7.98 (d, 2.2 Hz, 1H); 8.50 (d, 7.0 Hz, 1H); 8.77 (s, 1H).

Example 17

2-[(S)-1-Carboxy-2-(4-methoxy-phenyl)-ethylamino]-6-chloro-quinoline-3-carboxylic acid In close analogy to the procedure described in Example 1, 2,6-dichloroquinoline-3-carboxylic acid is reacted with 4-methoxy-L-phenylalanine to provide the title compound in 60% yield as yellow needles (recrystallization from EtOH).

Mp 155-158° C.; $^1$H-NMR (200 MHz, DMSO-d$_6$), δ (ppm) 2.96-3.21 (m, 2H); 3.67 (s, 3H); 4.80-4.89 (m, 1H); 6.80 (d, 8.6 Hz, 2H); 7.15 (d, 8.6 Hz, 2H); 7.43-7.55 (m, 2H); 7.88 (d, 2.0 Hz, 1H); 8.61 (s, 1H); 9.37 (br s, 1H).

Example 18

2-[1-Carboxy-2-(5-methoxy-1H-indol-3-yl)-ethylamino]-6-chloro-quinoline-3-carboxylic acid acetic acid salt In close analogy to the procedure described in Example 1, 2,6-dichloroquinoline-3-carboxylic acid is reacted with 5-methoxy-DL-tryptophan to provide the title compound in 85% yield as yellow needles (flash chromatography on SiO$_2$, eluent CHCl$_3$, MeOH, AcOH—10, 1, 0.2).

Mp >250° C. (decomp.); $^1$H-NMR (200 MHz, DMSO-d$_6$), δ (ppm) 1.88 (s, 3H); 3.05-3.30 (m, 2H); 3.53 (s, 3H); 4.78 (br s, 1H); 6.60 (d, 8.0 Hz, 1H); 6.94 (s, 1H); 7.10-7.20 (m, 2H); 7.38-7.45 (m, 2H); 7.70-7.80 (m, 1H); 8.43 (s, 1H); 10.17 (br s, 1H); 10.60 (br s, 1H).

Example 19

2-((R)-2-Benzyloxy-1-carboxy-ethylamino)-6-chloro-quinoline-3-carboxylic acid

In close analogy to the procedure described in Example 1, 2,6-dichloroquinoline-3-carboxylic acid is reacted with O-benzyl-D-serine to provide the title compound in 34% yield as yellow needles (recrystallization from DMF/water).

Mp 190-192° C. (decomp.); $^1$H-NMR (200 MHz, DMSO-d$_6$), δ (ppm) 3.79-3.85 (m, 1H); 3.94-4.01 (m, 1H); 4.53 (s, 2H); 4.92-5.02 (m, 1H); 7.20-7.35 (m, 5H); 7.47 (d, 9.4 Hz, 1H); 7.56-7.62 (m, 1H); 7.98 (d, 3.0 Hz, 1H); 8.75-8.83 (m, 2H).

Example 20

2-[(R)-1-Carboxy-2-(1-methyl-1H-indol-3-yl)-ethylamino]-6-chloro-quinoline-3-carboxylic acid In close analogy to the procedure described in Example 1, 2,6-dichloroquinoline-3-carboxylic acid is reacted with 1-methyl-D-tryptophan to provide the title compound in 87% yield as yellow needles (recrystallization from DMF/water).

Mp 148-150° C. (decomp.); $^1$H-NMR (200 MHz, DMSO-d$_6$), δ (ppm) 3.05-3.30 (m, 2H); 3.71 (s, 3H); 4.95-5.05 (m, 1H); 6.93-7.14 (m, 3H); 7.35 (d, 8.8 Hz, 1H); 7.49-7.64 (m, 3H); 7.97 (d, 1.8 Hz, 1H); 8.53 (d, 7.0 Hz, 1H); 8.74 (s, 1H).

Example 21

2-[1-Carboxy-2-(5-methyl-1H-indol-3-yl)-ethylamino]-6-chloro-quinoline-3-carboxylic acid In close analogy to the procedure described in Example 1, 2,6-dichloroquinoline-3-carboxylic acid is reacted with 5-methyl-DL-tryptophan to provide the title compound in 99% yield as yellow needles (recrystallization from DMF/water).

Mp 157-163° C. (decomp.); $^1$H-NMR (200 MHz, DMSO-d$_6$), δ (ppm) 2.29 (s, 3H); 3.05-3.30 (m, 2H); 4.95-5.05 (m, 1H); 6.85 (d, 8.4 Hz, 1H); 7.08-7.19 (m, 3H); 7.50-7.65 (m, 2H); 7.98 (d, 2.0 Hz, 1H); 8.55 (d, 7.0 Hz, 1H); 8.75 (s, 1H); 10.73 (s, 1H).

Example 22

2-[(S)-2-(4-Benzyloxy-phenyl)-1-carboxy-ethylamino]-6-chloro-quinoline-3-carboxylic acid In close analogy to the procedure described in Example 1, 2,6-dichloroquinoline-3-carboxylic acid is reacted with O-benzyl-L-tyrosine to provide the title compound in 32% yield as yellow needles (recrystallization from acetone/EtOH).

Mp 169-171° C.; $^1$H-NMR (200 MHz, DMSO-d$_6$), δ (ppm) 3.00-3.30 (m, 2H), 4.85-4.97 (m, 1H); 5.01 (s, 2H); 6.89 (d, 9.2 Hz, 2H); 7.13 (d, 8.8 Hz, 2H); 7.30-7.63 (m, 7H); 7.97 (d, 1.8 Hz, 1H); 8.55 (d, 5.8 Hz, 1H); 8.74 (s, 1H).

Example 23

2-[(S)-1-Carboxy-2-(4-chloro-phenyl)-ethylamino]-6-chloro-quinoline-3-carboxylic acid In close analogy to the procedure described in Example 1, 2,6-dichloroquinoline-3-carboxylic acid is reacted with 4-chloro-L-phenylalanine to provide the title compound in 63% yield as yellow needles (recrystallization from EtOH/water).

Mp 163-168° C.; $^1$H-NMR (200 MHz, DMSO-d$_6$), δ (ppm) 3.08-3.30 (m, 2H); 4.92-5.02 (m, 1H); 7.22 (d, 8.4 Hz, 2H); 7.31 (d, 8.6 Hz, 2H); 7.49-7.64 (m, 2H); 7.98 (d, 2.8 Hz, 1H); 8.48 (d, 6.8 Hz, 1H); 8.75 (s, 1H).

Example 24

2-(1-Carboxy-indan-1-ylamino)-6-chloro-quinoline-3-carboxylic acid

In close analogy to the procedure described in Example 1, 2,6-dichloroquinoline-3-carboxylic acid is reacted with DL-1-aminoindan-1-carboxylic acid to provide the title compound in 8% yield as yellow needles (flash chromatography on SiO$_2$, eluent CHCl$_3$, MeOH, AcOH—15, 1, 0.2 and recrystallization from MeOH).

Mp 141-144° C.; $^1$H-NMR (200 MHz, DMSO-d$_6$), δ (ppm) 2.14-2.60 (m, 2H); 3.00-3.20 (m, 2H); 7.14-7.46 (m, 5H); 7.59-7.78 (m, 1H); 7.99-8.07 (m, 1H); 8.44 (s), 8.55 (d, 7.0 Hz), 8.77 (s) and 8.92 (br s)—total 2H).

Example 25

2-[1-Carboxy-2-(5-fluoro-1H-indol-3-yl)-ethylamino]-6-chloro-quinoline-3-carboxylic acid In close analogy to the procedure described in Example 1, 2,6-dichloroquinoline-3-carboxylic acid is reacted with 5-fluoro-DL-tryptophan to provide the title compound in 90% yield as yellow needles (recrystallization from DMF/water).

Mp 146-162° C. (decomp.); $^1$H-NMR (200 MHz, DMSO-d$_6$), δ (ppm) 3.05-3.30 (m, 2H); 4.95-5.07 (m, 1H); 6.82-6.92 (m, 1H); 7.17-7.73 (m, 3H); 7.50-7.64 (m, 2H); 7.98 (d, 3.0 Hz, 1H); 8.55 (d, 7.6 Hz, 1H); 8.75 (s, 1H); 10.99 (br s, 1H).

Example 26

2-(1-Carboxy-ethylamino)-6-chloro-quinoline-3-carboxylic acid

In close analogy to the procedure described in Example 1, 2,6-dichloroquinoline-3-carboxylic acid is reacted with DL-2-aminopropionic acid to provide the title compound in 14% yield as yellow needles (flash chromatography on SiO$_2$, eluent CHCl$_3$, MeOH, AcOH—10, 1, 0.2 and recrystallization from DMF/water).

Mp 178-190° C.; $^1$H-NMR (200 MHz, DMSO-d$_6$), δ (ppm) 1.46 (d, 8.0 Hz, 3H); 4.62-4.78 (m, 1H); 7.47-7.68 (m, 2H); 7.98 (d, 1.8 Hz, 1H); 8.50 (d, 7.0 Hz, 1H); 8.76 (s, 1H).

Example 27

2-((S)-5-Amino-1-carboxy-pentylamino)-6-chloro-quinoline-3-carboxylic acid dihydrobromide In close analogy to the procedure described in Example 1, 2,6-dichloroquinoline-3-carboxylic acid is reacted with L-tryptophan to provide the title compound in moderate yield.

Mp 174-182° C.; $^1$H-NMR (200 MHz, DMSO-d$_6$), δ (ppm) 1.40-1.61 (m, 4H); 1.81-2.02 (m, 2H); 2.71-2.82 (m, 2H); 4.81 (br s, 1H); 7.50-7.80 (m, 5H); 8.04 (s, 1H); 8.85 (br s, 2H). Anal. Found (C$_{16}$H$_{18}$ClN$_3$O$_4$×2HBr) (%): C, 37.76; H, 4.12; N, 7.71.

Example 28

2-(1-Carboxy-3-phenyl-propylamino)-6-chloro-quinoline-3-carboxylic acid

In close analogy to the procedure described in Example 1, 2,6-dichloroquinoline-3-carboxylic acid is reacted with DL-homophenylalanine to provide the title compound in 77% yield as yellow needles (recrystallization from EtOH).

Mp 179-182° C. (decomp.); $^1$H-NMR (200 MHz, DMSO-d$_6$), δ (ppm) 2.03-2.25 (m, 2H); 2.69 (t, 7.3 Hz, 2H); 4.67-4.77 (m, 1H); 7.16-7.28 (m, 5H); 7.43-7.63 (m, 2H); 7.99 (d, 2.0 Hz, 1H); 8.58 (d, 6.8 Hz, 1H); 8.78 (s, 1H). Anal. Found (C$_{20}$H$_{17}$ClN$_2$O$_4$) (%): C, 62.18; H, 4.23; N, 7.19.

Example 29

2-[1-Carboxy-2-(1H-imidazol-4-yl)-ethylamino]-quinoline-3-carboxylic acid

In close analogy to the procedure described in Example 1, 2,6-dichloroquinoline-3-carboxylic acid is reacted with DL-histidine to provide the title compound in 33% yield as yellow needles (recrystallization from DMF/water).

Mp 223-228° C. (decomp.); $^1$H-NMR (200 MHz, DMSO-d$_6$), δ (ppm) 3.05-3.27 (m, 2H); 4.92 (br s, 1H); 6.99 (s, 1H); 7.44-7.59 (m, 2H); 7.84 (s, 1H); 7.92 (s, 1H); 8.66 (s, 1H); 8.97 (br s, 1H).

Example 30 threo-2-(1-Carboxy-2-phenyl-propylamino)-6-chloro-quinoline-3-carboxylic acid

In close analogy to the procedure described in Example 1, 2,6-dichloroquinoline-3-carboxylic acid is reacted with β-methyl-DL-phenylalanine hydrochloride and crude product is separated by flash chromatography on SiO$_2$ using CHCl$_3$, MeOH, AcOH—15, 1, 0.2 as eluent. Fractions with R$_f$ 0.30 are combined, evaporated in vacuo and the residue is recrystallized from DMF-water to provide the threo-isomer of title compound in 22% yield as yellow needles.

Mp 173-181° C.; $^1$H-NMR (400 MHz, DMSO-d$_6$); δ (ppm) 1.35 (d, 7.2 Hz, 3H); 3.40-3.50 (m, 1H); 4.94-4.98 (m, 1H); 7.19-7.35 (m, 5H); 7.49-7.61 (m, 2H); 7.96 (s, 1H); 8.38 (d, 7.2 Hz, 1H); 8.71 (s, 1H).

Example 31 erythro-2-(1-Carboxy-2-phenyl-propylamino)-6-chloro-quinoline-3-carboxylic acid

Chromatographical separation of the crude product from Example 30 is continued. Fractions with R$_f$ 0.20 are combined, evaporated in vacuo and the residue is recrystallized from MeOH-water to provide the erythro-isomer of title compound in 14% yield as yellow needles.

Mp 193-197° C.; $^1$H-NMR (400 MHz, DMSO-d$_6$); δ (ppm) 1.39 (d, 7.2 Hz, 3H); 3.40-3.50 (m, 1H); 4.97 (br s, 1H); 7.13-7.30 (m, 5H); 7.42-7.58 (m, 2H); 7.94 (d, 2.4 Hz, 1H); 8.70 (br s, 1H); 8.73 (s, 1H).

Example 32

2-((S)-1-Carboxy-2-phenyl-ethylamino)-6,7-dichloro-quinoline-3-carboxylic acid

A mixture of 2,6,7-trichloroquinoline-3-carboxylic acid ethyl ester (80 mg, 0.26 mmol), L-phenylalanine (80 mg, 0.52 mmol) and potassium carbonate (180 mg, 1.31 mmol) in DMF (1 mL) is stirred for 22 h at 130° C. in closed reaction vial. After cooling the reaction mixture is diluted with water, acidified by addition of 2N HCl, and the precipitated solid is collected on filter, washed with water and air dried to give the title compound (40 mg, 38%) as yellow powder.

Mp 141-143° C.; $^1$H-NMR (200 MHz, DMSO-d$_6$), δ (ppm) 3.05-3.30 (m, 2H); 4.94-5.03 (m, 1H); 7.20-7.35 (m, 5H); 7.74 (s, 1H); 8.23 (s, 1H); 8.61 (d, 7.8 Hz, 1H); 8.79 (s, 1H).

Example 33

2-[1-Carboxy-2-(6-fluoro-1H-indol-3-yl)-ethylamino]-6-chloro-quinoline-3-carboxylic acid In close analogy to the procedure described in Example 1, 2,6-dichloroquinoline-3-carboxylic acid is reacted with 6-fluoro-DL-tryptophan to provide the title compound in 42% yield as yellow needles (recrystallization from MeOH).

Mp 170-174° C.; $^1$H-NMR (200 MHz, DMSO-d$_6$), δ (ppm) 3.05-3.30 (m, 2H); 4.95-5.06 (m, 1H); 6.75-6.84 (m, 1H); 7.04-7.14 (m, 2H); 7.43-7.64 (m, 3H); 7.98 (s, 1H); 8.52 (d, 7.0 Hz, 1H); 8.74 (s, 1H); 10.96 (s, 1H).

Example 34

2-[(S)-1-Carboxy-2-(4-hydroxy-phenyl)-ethylamino]-6-chloro-quinoline-3-carboxylic acid In close analogy to the procedure described in Example 1, 2,6-dichloroquinoline-3-carboxylic acid is reacted with L-tyrosine (2 eq.) to provide the title compound in 71% yield as yellow needles (recrystallization from acetone/water).

Mp 176-188° C.; $^1$H-NMR (200 MHz, DMSO-d$_6$), δ (ppm) 2.94-3.18 (m, 2H); 4.82-4.92 (m, 1H); 6.63 (d, 9.0 Hz, 2H); 7.00 (d, 8.8 Hz, 2H); 7.47-7.62 (m, 2H); 7.97 (d, 3.0 Hz, 1H); 8.49 (d, 6.8 Hz, 1H); 8.74 (s, 1H); 9.22 (br s, 1H).

Example 35

2-((S)-1-Carboxy-2-cyclohexyl-ethylamino)-6-chloro-quinoline-3-carboxylic acid

In close analogy to the procedure described in Example 1, 2,6-dichloroquinoline-3-carboxylic acid is reacted with L-α-aminocyclohexanepropionic acid to provide the title compound in 97% yield as yellow needles.

Mp 160-168° C.; $^1$H-NMR (200 MHz, DMSO-d$_6$), δ (ppm) 0.88 (m, 6H); 1.50-1.82 (m, 7H); 4.69-4.80 (m, 1H); 7.43-7.61 (m, 2H); 7.96 (d, 2.0 Hz, 1H); 8.62 (d, 5.6 Hz, 1H); 8.73 (s, 1H).

Example 36

2-[(R)-1-Carboxy-2-(1H-indol-3-yl)-ethylamino]-6,7-dichloro-quinoline-3-carboxylic acid In close analogy to the procedure described in Example 32, 2,6,7-trichloroquinoline-3-carboxylic acid ethyl ester is reacted with D-tryptophan (heating for 39 h) to provide the title compound in 29% yield as pale yellow powder.

Mp >250° C.; $^1$H-NMR (200 MHz, DMSO-d$_6$), δ (ppm) 3.05-3.30 (m, 2H); 4.97-5.06 (m, 1H); 6.93-7.08 (m, 2H); 7.15 (s, 1H); 7.31 (d, 7.0 Hz, 1H); 7.49 (d, 7.2 Hz, 1H); 7.70 (s, 1H); 8.22 (s, 1H); 8.66 (d, 5.8 Hz, 1H); 8.78 (s, 1H); 10.90 (s, 1H).

Example 37

2-[(S)-1-Carboxy-2-(3,4-dihydroxy-phenyl)-ethylamino]-6-chloro-quinoline-3-carboxylic acid In close analogy to the procedure described in Example 1, 2,6-dichloroquinoline-3-carboxylic acid is reacted with 3,4-dihydroxy-L-phenylalanine to provide the title compound in 50% yield as yellow needles (recrystallization from acetone/toluene).

Mp 143-160° C. (decomp.); $^1$H-NMR (200 MHz, DMSO-d$_6$), δ (ppm) 2.82-3.11 (m, 2H); 4.79-4.88 (m, 1H); 6.45 (d, 7.8 Hz, 1H); 6.57-6.61 (m, 2H); 7.48-7.63 (m, 2H); 7.98 (d, 2.8 Hz, 1H); 8.49 (d, 6.8 Hz, 1H); 8.74 (br s, 3H).

Example 38

2-[1-Carboxy-2-(3-carboxy-6-chloro-quinolin-2-ylamino)-ethylamino]-6-chloro-quinoline-3-carboxylic acid ammonium salt In close analogy to the procedure described in Example 1, 2,6-dichloroquinoline-3-carboxylic acid is reacted with DL-2,3-diaminopropionic acid to provide the title compound in 23% yield as yellow needles (recrystallization from MeOH/water/NH$_4$OH).

Mp >260° C. (decomp.); $^1$H-NMR (200 MHz, DMSO-d$_6$), δ (ppm) 3.88-3.98 (m, 1H); 4.12-4.24 (m, 1H); 4.98 (br s, 1H); 7.41-7.55 (m, 5H); 7.85-7.95 (m, 2H); 8.60-8.68 (m, 2H); 9.43 (br s, 2H).

Example 39

2-[1-Carboxy-2-(4-fluoro-phenyl)-ethylamino]-6-chloro-quinoline-3-carboxylic acid In close analogy to the procedure described in Example 1, 2,6-dichloroquinoline-3-carboxylic acid is reacted with 4-fluoro-DL-phenylalanine to provide the title compound in 80% yield as yellow needles.

Mp 165-169° C. (decomp.); $^1$H-NMR (200 MHz, DMSO-$d_6$), δ (ppm) 3.08-3.30 (m, 2H); 4.91-5.01 (m, 1H); 7.07 (t, 8.8 Hz, 2H); 7.20-7.27 (m, 2H); 7.49-7.64 (m, 2H); 7.97 (d, 2.8 Hz, 1H); 8.54 (d, 6.8 Hz, 1H); 8.74 (s, 1H).

Example 40

2-[1-Carboxy-2-(2-fluoro-phenyl)-ethylamino]-6-chloro-quinoline-3-carboxylic acid ammonium salt In close analogy to the procedure described in Example 1, 2,6-dichloroquinoline-3-carboxylic acid is reacted with 2-fluoro-DL-phenylalanine to provide the title compound in 58% yield as yellow needles (recrystallization from MeOH/NH$_4$OH).

Mp 144-148° C. (decomp.); $^1$H-NMR (200 MHz, DMSO-$d_6$), δ (ppm) 3.01-3.11 (m, 1H); 3.22-3.32 (m, 1H); 4.84-4.93 (m, 1H); 7.02-7.47 (m, 6H); 7.78 (s, 1H); 8.46 (s, 1H); 10.20 (br s, 1H). Anal. Found ($C_{19}H_{14}ClFN_2O_4×NH_3$) (%): C, 56.15; H, 4.21; N, 9.79.

Example 41

2-[(S)-1-Carboxy-2-(4-hydroxy-3-nitro-phenyl)-ethylamino]-6-chloro-quinoline-3-carboxylic acid In close analogy to the procedure described in Example 1, 2,6-dichloroquinoline-3-carboxylic acid is reacted with 3-nitro-L-tyrosine to provide the title compound in 10% yield as yellow needles.

Mp 168-175° C. (decomp.); $^1$H-NMR (200 MHz, DMSO-$d_6$), δ (ppm) 3.07-3.30 (m, 2H); 4.94-5.03 (m, 1H); 7.01 (d, 9.0 Hz, 1H); 7.35-7.64 (m, 3H); 7.73 (s, 1H); 7.99 (s, 1H); 8.48 (d, 7.0 Hz, 1H); 8.76 (s, 1H); 10.80 (s, 1H).

Example 42

2-((S)-1-Carboxy-2-phenyl-ethylamino)-6,8-dichloro-quinoline-3-carboxylic acid In close analogy to the procedure described in Example 1, 2,6,8-trichloroquinoline-3-carboxylic acid is reacted with L-phenylalanine to provide the title compound in 39% yield as yellow needles (recrystallization from EtOH).

Mp 218-223° C.; $^1$H-NMR (200 MHz, DMSO-$d_6$), δ (ppm) 3.02-3.40 (m, 2H); 4.89 (m, 1H); 7.13-7.26 (m, 5H); 7.66 (d, 3.2 Hz, 1H); 7.79 (d, 2.2 Hz, 1H); 8.44 (s, 1H); 10.81 (br s, 1H).

Example 43

6-Chloro-2-[1-(naphthalen-2-ylcarbamoyl)-ethylamino]-quinoline-3-carboxylic acid A mixture of 2,6-dichloroquinoline-3-carboxylic acid (194 mg, 0.8 mmol), DL-alanine-β-naphthylamide (251 mg, 1 mmol) and triethylamine (900 mg, 8.9 mmol) in dioxane (1 mL) is stirred for 24 h at 135° C. in closed reaction vial. After evaporation of solvents in vacuo, the residue is acidified by addition of 2N HCl, and the precipitated solid is collected on filter, washed with water and recrystallized from MeOH-water to give the title compound (200 mg, 60%) as yellow needles.

Mp 230-243° C.; $^1$H-NMR (200 MHz, DMSO-$d_6$), δ (ppm) 1.51 (t, 6.8 Hz, 3H); 4.92 (br s, 1H); 7.36-7.64 (m, 5H); 7.76-7.90 (m, 4H); 8.32 (s, 1H); 8.66 (s, 1H); 9.45 (br s, 1H); 10.46 (s, 1H).

Example 44

2-((R)-1-Carboxy-2-phenyl-ethylamino)-quinoline-3-carboxylic acid

In close analogy to the procedure described in Example 1, 2-chloroquinoline-3-carboxylic acid is reacted with D-phenylalanine to provide the title compound in moderate yield. Physical characteristics are as follows:

Mp 140-141.5° C.; $^1$H-NMR (200 MHz, DMSO-$d_6$); δ (ppm) 3.05-3.20 (m, 2H), 4.95-5.04 (m, 1H); 7.15-7.32 (m, 5H); 7.50-7.70 (m, 2H); 7.85 (d, 8 Hz, 1H); 8.44 (d, 7.6 Hz, 1H); 8.75 (s, 1H); LC MS m/z 337 (MH+).

Example 45

2-[(R)-1-Carboxy-2-(1H-indol-3-yl)-ethylamino]-quinoline-3-carboxylic acid

In close analogy to the procedure described in Example 1, 2-chloroquinoline-3-carboxylic acid is reacted with D-tryptophan to provide the title compound in moderate yield as yellow needles (recrystallization from isopropanol).

Mp 162-163° C.; $^1$H-NMR (200 MHz, DMSO-$d_6$), δ (ppm) 3.25-3.50 (m, 2H); 5.00-5.10 (m, 1H); 6.90-7.10 (m, 2H); 7.15-7.35 (m, 3H); 7.50-7.70 (m, 3H); 7.85 (d, 8.8 Hz, 1H); 8.53 (br d, 1H); 8.75 (s, 1H); 10.90 (s, 1H).

Example 46

2-[1-(1-Carbamoyl-2-phenyl-ethylcarbamoyl)-2-phenyl-ethylamino]-6-chloro-quinoline-3-carboxylic acid In close analogy to the procedure described in Example 1, 2,6-dichloroquinoline-3-carboxylic acid is reacted with 2-amino-3-phenyl-propionamide to give the title compound in moderate yield.

Mp 130-140° C. (decomp.). $^1$H-NMR (200 MHz, DMSO-$d_6$), δ (ppm) 2.72-3.20 (m, 4H); 4.44 (d, 14.0 Hz, 1H); 4.92 (d, 19.8 Hz, 1H); 6.81 (s, 1H); 7.09-7.25 (m, 10H); 7.38 (s) and 7.48 (s) (total 1H); 7.60 (s, 1H); 7.97 (s, 1H); 8.33 (s, 1H); 8.45 (d, 9.6 Hz, 1H); 8.72 (s, 1H); 13.59 (br s, 1H). LCMS m/z 517 (M+1).

Example 47

6-Bromo-2-((R)-1-carboxy-2-phenyl-ethylamino)-quinoline-3-carboxylic acid

In close analogy to the procedure described in Example 32, 6-bromo-2-chloroquinoline-3-carboxylic acid ethyl ester is reacted with D-phenylalanine to provide the title compound in good yield.

Mp 140-141° C. $^1$H-NMR (200 MHz, DMSO-$d_6$), δ (ppm) 3.08-3.30 (m, 2H); 4.92-5.02 (m, 1H); 7.22-7.32 (m, 5H);

7.46 (d, 8.8 Hz, 1H); 7.72 (d, 6.6 Hz, 1H); 8.14 (s, 1H); 8.50 (d, 6.4 Hz, 1H); 8.76 (s, 1H). LCMS m/z 415 (M+1).

Example 48

2-{(S)-2-[3-Amino-4-(3-carboxy-6-chloro-quinolin-2-yloxy)-phenyl]-1-carboxy-ethylamino}-6-chloro-quinoline-3-carboxylic acid In close analogy to the procedure described in Example 1, 2,6-dichloroquinoline-3-carboxylic acid is reacted with 3-amino-4-hydroxy-L-phenylalanine and crude product is separated by flash chromatography on $SiO_2$ to provide the title compound in good yield.

Mp >250° C. LCMS m/z 607 (M+1).

Example 49

2-[(S)-2-(3-Amino-4-hydroxy-phenyl)-1-carboxy-ethylamino]-6-chloro-quinoline-3-carboxylic acid Chromatographical separation of the crude product from Example 48 is continued to provide the title compound in moderate yield.

Mp >250° C. $^1$H-NMR (200 MHz, DMSO-$d_6$), δ (ppm) 2.82-2.99 (m, 2H); 4.62-4.76 (m, 1H); 6.30 (d, 7.8 Hz, 1H); 6.48-6.52 (m, 2H); 7.38-7.48 (m, 3H); 7.80 (s, 1H); 8.47 (s, 1H); 8.78 (br d, 1H). LCMS m/z 402 (M+1).

Example 50

2-[(S)-1-Carboxy-4-(6-chloro-3-carboxy-quinolin-2-ylamino)-butylamino]-6-chloro-quinoline-3-carboxylic acid In close analogy to the procedure described in Example 1, 2,6-dichloroquinoline-3-carboxylic acid is reacted with L-2,5-diaminopentanoic acid to provide the title compound in good yield.

Mp >166° C. (decomp.). LCMS m/z 541 (M−1).

Example 51

2-[(S)-1-Carboxy-2-(3-chloro-4-hydroxy-phenyl)-ethylamino]-6-chloro-quinoline-3-carboxylic acid In close analogy to the procedure described in Example 1, 2,6-dichloroquinoline-3-carboxylic acid is reacted with 3-chloro-4-hydroxy-L-phenylalanine to provide the title compound in good yield.

Mp 150-175° C. (decomp.). $^1$H-NMR (200 MHz, DMSO-$d_6$), δ (ppm) 2.86-3.12 (m, 2H); 4.70-4.83 (m, 1H); 6.87 (d, 8.0 Hz, 1H); 6.99 (d, 9.0 Hz, 1H); 7.18 (d, 1.6 Hz, 1H); 7.41 (s, 2H); 7.78 (s, 1H); 8.44 (s, 1H); 10.32 (br s, 1H). LCMS m/z 421 (M+1).

Example 52

2-[1-Carboxy-2-(3-fluoro-4-hydroxy-phenyl)-ethylamino]-6-chloro-quinoline-3-carboxylic acid In close analogy to the procedure described in Example 1, 2,6-dichloroquinoline-3-carboxylic acid is reacted with 3-fluoro-4-hydroxy-DL-phenylalanine to provide the title compound in good yield.

Mp >160° C. (decomp.). $^1$H-NMR (200 MHz, DMSO-$d_6$), δ (ppm) 2.48-3.13 (m, 2H); 4.71-4.84 (m, 1H); 6.78-7.01 (m, 3H); 7.36-7.46 (m, 2H); 7.78 (s, 1H); 8.46 (s, 1H); 10.26 (br s, 1H). LCMS m/z 405 (M+1).

Example 53

2-[1-Carboxy-2-(4-carboxy-phenyl)-ethylamino]-6-chloro-quinoline-3-carboxylic acid In close analogy to the procedure described in Example 1, 2,6-dichloroquinoline-3-carboxylic acid is reacted with 4-carboxy-DL-phenylalanine and crude product is separated by flash chromatography on $SiO_2$ to provide the title compound in good yield.

Mp >180° C. (decomp.). $^1$H-NMR (200 MHz, DMSO-$d_6$), δ (ppm) 3.05-3.31 (m, 2H); 4.76-4.88 (m, 1H); 7.30-7.49 (m, 4H); 7.70-7.85 (m, 3H); 8.41 (s, 1H); 10.31 (br d, 1H). LCMS m/z 415 (M+1).

Example 54

2-[1-[1-Carboxy-2-(4-carboxy-phenyl)-ethylcarbamoyl]-2-(4-carboxy-phenyl)-ethylamino]-6-chloro-quinoline-3-carboxylic acid Chromatographical separation of the crude product from Example 53 is continued to provide the title compound in good yield.

Mp >180° C. (decomp.). $^1$H-NMR (200 MHz, DMSO-$d_6$), δ (ppm) 2.83-3.28 (m, 4H); 4.32 (br s, 1H); 4.58-4.68 (m, 1H); 7.12 (d, 7.6 Hz, 1H); 7.20-7.35 (m, 3H); 7.47 (d, 7.2 Hz, 2H); 7.66-7.78 (m, 5H); 8.03 (d, 4.0 Hz, 1H); 8.18 (br d), 8.32 (br d), 8.46 (br d) and 8.79 (br d) (total 2H). LCMS m/z 605 (M+1).

Example 55

2-((S)-1-Carboxy-2-pyridin-4-yl-ethylamino)-6-chloro-quinoline-3-carboxylic acid In close analogy to the procedure described in Example 1, 2,6-dichloroquinoline-3-carboxylic acid is reacted with (L)-2-amino-3-pyridin-4-yl-propionic acid to provide the title compound in good yield.

Mp 155-158° C. (decomp.). LCMS m/z 372 (M+1).

Example 56

6,8-Dibromo-2-(1-carboxy-2-phenyl-ethylamino)-quinoline-3-carboxylic acid

In close analogy to the procedure described in Example 32, 6,8-dibromo-2-chloro-quinoline-3-carboxylic acid ethyl ester is reacted with DL-phenylalanine to provide the title compound in good yield.

Mp 115-117° C. $^1$H-NMR (200 MHz, DMSO-$d_6$), δ (ppm) 3.10-3.30 (m, 2H); 5.00-5.12 (m, 1H); 7.15-7.40 (m, 5H); 8.16 (s, 1H); 8.19 (s, 1H); 8.69 (br d, 1H); 8.78 (s, 1H). LCMS m/z 495 (M+1).

Example 57

2-[1-Carboxy-2-(3,5-dimethyl-pyrazol-1-yl)-ethylamino]-6-chloro-quinoline-3-carboxylic acid In close analogy to the procedure described in Example 1, 2,6-dichloroquinoline-3-carboxylic acid is reacted with 2-amino-3-(3,5-dimethyl-pyrazol-1-yl)-propionic acid to provide the title compound in good yield.

Mp >200° C. (decomp.). $^1$H-NMR (200 MHz, DMSO-d$_6$), δ (ppm) 2.00 (s, 3H); 2.11 (s, 3H); 4.31-4.47 (m, 2H); 4.92 (br s, 1H); 5.62 (s, 1H); 7.30-7.50 (m, 2H); 7.74 (s, 1H); 8.37 (s, 1H); 9.80-10.60 (br s, 1H). LCMS m/z 389 (M+1).

Example 58

2-[2-(4-Amino-phenyl)-1-carboxy-ethylamino]-6-chloro-quinoline-3-carboxylic acid In close analogy to the procedure described in Example 1, 2,6-dichloroquinoline-3-carboxylic acid is reacted with 4-amino-DL-phenylalanine and crude product is separated by flash chromatography on SiO$_2$ to provide the title compound in good yield.

Mp >250° C. (decomp.). LCMS m/z 386 (M+1).

Example 59

2-{1-Carboxy-2-[4-(3-carboxy-6-chloro-quinolin-2-ylamino)-phenyl]-ethylamino}-6-chloro-quinoline-3-carboxylic acid Chromatographical separation of the crude product from Example 58 is continued to provide the title compound in moderate yield.

Mp >250° C. (decomp.). $^1$H-NMR (200 MHz, DMSO-d$_6$), δ (ppm) 3.00-3.30 (m, 2H); 4.81-4.94 (m, 1H); 7.18 (d, 7.4 Hz, 2H); 7.47-7.62 (m, 4H); 7.80-7.90 (m, 4H); 8.56 (s, 1H); 8.62 (s, 1H); 9.81 (br s, 1H); 13.14 (br s, 1H). LCMS m/z 591 (M+1).

Example 60

2-[1-[1-Carboxy-2-(3-carboxy-phenyl)-ethylcarbamoyl]-2-(3-carboxy-phenyl)-ethylamino]-6-chloro-quinoline-3-carboxylic acid In close analogy to the procedure described in Example 1, 2,6-dichloroquinoline-3-carboxylic acid is reacted with 3-carboxy-DL-phenylalanine to provide the title compound in good yield.

Mp >190° C. (decomp.). $^1$H-NMR (200 MHz, DMSO-d$_6$), δ (ppm) 3.00-3.30 (m, 4H); 4.52 (br s, 1H); 4.85 (br s, 1H); 7.22-7.52 (m, 6H); 7.67-7.92 (m, 6H); 8.15 (br d), 8.25 (br d) and 8.99 (br d) (total 2H). LCMS m/z 606 (M+1).

Example 61

2-[1-Carboxy-2-(3-methoxy-phenyl)-ethylamino]-6-chloro-quinoline-3-carboxylic acid In close analogy to the procedure described in Example 32, 2,6-dichloroquinoline-3-carboxylic acid is reacted with 3-methoxy-DL-phenylalanine in DMSO to provide the title compound in good yield.

Mp 165-170° C. (decomp.). $^1$H-NMR (200 MHz, DMSO-d$_6$), δ (ppm) 3.00-3.30 (m, 2H); 3.69 (s, 3H); 4.91-5.01 (m, 1H); 6.74-6.80 (m, 3H); 7.17 (t, 7.8 Hz, 1H); 7.52-7.64 (m, 2H); 7.97 (d, 3.0 Hz, 1H); 8.50 (d, 6.6 Hz, 1H); 8.74 (s, 1H). LCMS m/z 401 (M+1).

Example 62

2-[1-Carboxy-2-(4-phenylethynyl-phenyl)-ethylamino]-6-chloro-quinoline-3-carboxylic acid In close analogy to the procedure described in Example 1, 2,6-dichloroquinoline-3-carboxylic acid is reacted with 2-amino-3-(4-phenylethynyl-phenyl)-propionic acid to provide the title compound in good yield.

Mp 164-173° C. $^1$H-NMR (200 MHz, DMSO-d$_6$), δ (ppm) 3.11-3.35 (m, 2H); 4.91-5.04 (m, 1H); 7.27 (d, 8.0 Hz, 2H); 7.41-7.60 (m, 9H); 7.94 (s, 1H); 8.68 (s, 1H); 9.05 (br d, 1H). LCMS m/z 471 (M+1).

Example 63

2-[1-Carboxy-2-(3-hydroxy-phenyl)-ethylamino]-6-chloro-quinoline-3-carboxylic acid In close analogy to the procedure described in Example 32, 2,6-dichloroquinoline-3-carboxylic acid is reacted with 3-hydroxy-DL-phenylalanine and crude product is separated by flash chromatography on SiO$_2$ to provide the title compound in low yield.

$^1$H-NMR (200 MHz, DMSO-d$_6$), δ (ppm) 3.04-3.16 (m, 2H); 4.90-4.95 (m, 1H); 6.57-6.66 (m, 3H); 7.05 (t, 8 Hz, 1H); 7.52 (d, 9 Hz, 1H); 7.62 (d, 9 Hz, 1H); 7.99 (s, 1H); 8.59 (d, 6.2 Hz, 1H); 8.75 (s, 1H); 9.28 (br s, 1H). LCMS m/z 387 (M+1).

Example 64

2-[1-Carboxy-2-(3-hydroxy-phenyl)-ethylamino]-6,8-dichloro-quinoline-3-carboxylic acid In close analogy to the procedure described in Example 1, 2,6,8-trichloroquinoline-3-carboxylic acid is reacted with 3-hydroxy-DL-phenylalanine to provide the title compound in moderate yield. LCMS m/z 421 (M+1).

Example 65

2-[1-Carboxy-2-(2-methyl-benzooxazol-5-yl)-ethylamino]-6-chloro-quinoline-3-carboxylic acid In close analogy to the procedure described in Example 32, 2,6-dichloroquinoline-3-carboxylic acid is reacted with 2-amino-3-(2-methyl-benzooxazol-5-yl)-propionic acid to provide the title compound in good yield.

LCMS m/z 426 (M+1).

Example 66

2-[1-Carboxy-2-(phenylcarbamoyl-ethylamino)]-6-chloro-quinoline-3-carboxylic acid In close analogy to the procedure described in Example 32, 2,6-dichloroquinoline-3-carboxylic acid is reacted with 2-amino-N-phenyl-succinamic acid to provide the title compound in moderate yield.

$^1$H-NMR (400 MHz, DMSO-d$_6$), δ (ppm) 2.94-2.99 (m, 2H); 5.11 (br s, 1H); 7.01 (t, 7.6 Hz, 1H); 7.25-7.29 (m, 2H); 7.45-7.57 (m, 5H); 7.87 (s, 1H); 8.57 (s, 1H); 10.10 (s, 1H). LCMS m/z 414 (M+1).

Example 67

2-[1-Carboxy-2-(1H-indol-3-yl)-ethylamino]-6,8-dichloro-quinoline-3-carboxylic acid In close analogy to the procedure described in Example 1, 2,6,8-trichloroquinoline-3-carboxylic acid is reacted with DL-tryptophan to provide the title compound in good yield.
$^1$H-NMR (400 MHz, DMSO-d$_6$), δ (ppm) 3.30-3.36 (m, 1H); 3.46-3.51 (m, 1H); 5.05-5.10 (m, 1H); 6.90-6.94 (m, 1H); 7.02-7.06 (m, 1H); 7.16 (s, 1H); 7.31 (d, 7.6 Hz, 1H); 7.49 (d, 7.6 Hz, 1H); 7.88 (s, 1H); 7.99 (s, 1H); 8.77 (s, 1H); 8.86 (d, 5.6 Hz, 1H); 10.89 (s, 1H). LCMS m/z 444 (M+1).

Example 68

2-[1-Carboxy-2-(2-chloro-5-methoxy-phenyl)-ethylamino]-6-chloro-quinoline-3-carboxylic acid In close analogy to the procedure described in Example 1, 2,6-dichloroquinoline-3-carboxylic acid is reacted with 2-chloro-5-methoxy-DL-phenylalanine to provide the title compound in good yield.
Mp 180-185° C. $^1$H-NMR (200 MHz, DMSO-d$_6$), δ (ppm) 3.10-3.40 (m, 2H); 3.67 (s, 3H); 4.95-5.10 (m, 1H); 6.72-6.78 (m, 1H); 6.96 (d, 3.0 Hz, 1H); 7.25 (d, 8.8 Hz, 1H); 7.42-7.59 (m, 2H); 7.92 (d, 2.8 Hz, 1H); 8.67 (s, 1H); 8.88 (br s, 1H). LCMS m/z 435 (M+1).

Example 69

6-Chloro-2-[2-hydroxy-1-(3-methoxy-phenylcarbamoyl)-ethylamino]-quinoline-3-carboxylic acid In close analogy to the procedure described in Example 43, 2,6-dichloroquinoline-3-carboxylic acid is reacted with 2-amino-3-hydroxy-N-(3-methoxy-phenyl)-propionamide to provide the title compound in good yield. LCMS m/z 416 (M+1).

Example 70

6-Chloro-2-(phenylcarbamoyl-methyl-amino)-quinoline-3-carboxylic acid

In close analogy to the procedure described in Example 43, 2,6-dichloroquinoline-3-carboxylic acid is reacted with 2-amino-N-phenyl-acetamide to provide the title compound in good yield. LCMS m/z 356 (M+1).
$^1$H-NMR (400 MHz, DMSO-d$_6$), δ (ppm) 4.38 (d, 4.4 Hz, 2H); 7.05 (t, 7.4 Hz, 1H); 7.31 (t, 8.0 Hz, 2H); 7.51 (d, 9.2 Hz, 1H); 7.60-7.62 (m, 3H); 8.00 (d, 2.0 Hz, 1H); 8.69 (br s, 1H); 8.78 (s, 1H); 10.20 (s, 1H).

Example 71

6,8-Dichloro-2-(phenylcarbamoyl-methyl-amino)-quinoline-3-carboxylic acid

In close analogy to the procedure described in Example 43, 2,6,8-trichloroquinoline-3-carboxylic acid is reacted with 2-amino-N-phenyl-acetamide to provide the title compound in good yield. LCMS m/z 390 (M+1).

Example 72

2-[1-Carboxy-2-(2-methoxy-phenyl)-ethylamino]-6-chloro-quinoline-3-carboxylic acid In close analogy to the procedure described in Example 1, 2,6-dichloroquinoline-3-carboxylic acid is reacted with 2-methoxy-DL-phenylalanine to provide the title compound in good yield.
Mp >180° C. (decomp.). $^1$H-NMR (200 MHz, DMSO-d$_6$), δ (ppm) 2.86-3.20 (m, 2H); 3.72 (s, 3H); 4.69-4.82 (m, 1H); 6.72-6.88 (m, 2H); 7.07-7.16 (m, 2H); 7.31-7.42 (m, 2H); 7.74 (s, 1H); 8.43 (s, 1H); 9.93 (br s, 1H). LCMS m/z 401 (M+1).

Example 73

2-(2-Carbamoyl-1-carboxy-ethylamino)-6-chloro-quinoline-3-carboxylic acid

In close analogy to the procedure described in Example 32, 2,6-dichloroquinoline-3-carboxylic acid is reacted with 2-amino-succinamic acid to provide the title compound in moderate yield.
$^1$H-NMR (400 MHz, DMSO-d$_6$), δ (ppm) 2.58-2.66 (m, 2H); 4.83-4.87 (m, 1H); 6.82 (s, 1H); 7.41 (s, 2H); 7.66 (s, 1H); 7.77 (s, 1H); 8.42 (s, 1H); 10.31 (br s, 1H). LCMS m/z 338 (M+1).

Example 74

2-[1-Carboxy-2-(1-phenyl-ethylcarbamoyl)-ethylamino]-6-chloro-quinoline-3-carboxylic acid In close analogy to the procedure described in Example 32, 2,6-dichloroquinoline-3-carboxylic acid is reacted with 2-amino-N-(1-phenyl-ethyl)-succinamic acid to provide the title compound in good yield.
LCMS m/z 442 (M+1).

Example 75

2-(2-Carboxy-1-phenylcarbamoyl-ethylamino)-6-chloro-quinoline-3-carboxylic acid

In close analogy to the procedure described in Example 32, 2,6-dichloroquinoline-3-carboxylic acid is reacted with 3-amino-N-phenyl-succinamic acid to provide the title compound in good yield. LCMS m/z 414 (M+1).

Example 76

6-Chloro-2-(2-hydroxy-1-phenylcarbamoyl-ethylamino)-quinoline-3-carboxylic acid

In close analogy to the procedure described in Example 43, 2,6-dichloroquinoline-3-carboxylic acid is reacted with 2-amino-3-hydroxy-N-phenyl-propionamide to provide the title compound in good yield. LCMS m/z 386 (M+1).

Example 77

2-(3-Carbamoyl-1-carboxy-propylamino)-6-chloro-quinoline-3-carboxylic acid

In close analogy to the procedure described in Example 32, 2,6-dichloroquinoline-3-carboxylic acid is reacted with 2-amino-4-carbamoyl-butyric acid to provide the title compound in moderate yield. LCMS m/z 352 (M+1).

Example 78

2-{1-Carboxy-2-[1-(3-methyl-4-nitro-benzyl)-1H-imidazol-4-yl]-ethylamino}-6-chloro-quinoline-3-carboxylic acid In close analogy to the procedure described in Example 32, 2,6-dichloroquinoline-3-carboxylic acid is reacted with 2-amino-3-[1-(3-methyl-4-nitro-benzyl)-1H-imidazol-4-yl]-propionic acid to provide the title compound in good yield. LCMS m/z 510 (M+1).

Example 79

2-(3-Carboxy-6-chloro-quinolin-2-ylamino)-3-phenyl-succinic acid

In close analogy to the procedure described in Example 32, 2,6-dichloroquinoline-3-carboxylic acid is reacted with 2-amino-3-phenyl-succinic acid [*J. Med. Chem.* 1973, 16, 1277-1280] to provide the title compound in moderate yield.
Mp 165-170° C. (decomp.). $^1$H-NMR (200 MHz, DMSO-$d_6$), δ (ppm) 4.20 (d, 2.8 Hz, 1H); 5.05-5.20 (m, 1H); 7.05-7.36 (m, 5H); 7.40-7.60 (m, 2H); 7.80 (s) and 7.84 (s) (total 1H); 8.46 (s) and 8.55 (s) (total 1H); 8.68 (br s) and 10.22 (br s) (total 1H). LCMS m/z 415 (M+1).

Example 80

2-{4-[2-(3-Carboxy-6-chloro-quinolin-2-yl)amino-2-carboxy-ethyl]phenyl]-1-carboxy-ethylamino}-6-chloro-quinoline-3-carboxylic acid In close analogy to the procedure described in Example 32, 2,6-dichloroquinoline-3-carboxylic acid is reacted with 2-amino-3-[4-(2-amino-2-carboxy-ethyl)-phenyl]-propionic acid to provide the title compound in good yield.
Mp >170° C. (decomp.). $^1$H-NMR (200 MHz, DMSO-$d_6$), δ (ppm) 3.02-3.25 (m, 4H); 4.84-4.98 (m, 2H); 7.14 (s, 4H); 7.47-7.62 (m, 4H); 7.95 (s, 2H); 8.50-8.60 (m, 2H); 8.72 (s, 2H). LCMS m/z 663 (M+1).

Example 81

2-{2-[3-(3-carboxy-6-chloro-quinolin-2-yloxy)-phenyl]-1-carboxy-ethylamino}-6-chloro-quinoline-3-carboxylic acid Chromatographical separation of the crude product from Example 63 is continued to provide the title compound in good yield.
Mp 186-197° C. (decomp.). $^1$H-NMR (200 MHz, DMSO-$d_6$), δ (ppm) 3.00-3.20 (m, 2H); 4.91-5.03 (m, 1H); 7.02-7.57 (m, 8H); 7.75 (s, 1H); 8.11 (s, 1H); 8.38-8.43 (m, 1H); 8.54-8.63 (m, 1H); 9.68 (br d, 1H). LCMS m/z 592 (M+1).

Example 82

2-{2-[3-[2-(3-Carboxy-6-chloro-quinolin-2-yl)amino-2-carboxy-ethyl]-phenyl]-1-carboxy-ethylamino}-6-chloro-quinoline-3-carboxylic acid In close analogy to the procedure described in Example 1, 2,6-dichloroquinoline-3-carboxylic acid is reacted with 2-amino-3-[3-(2-amino-2-carboxy-ethyl)-phenyl]-propionic acid to provide the title compound in good yield.
Mp >185° C. (decomp.). $^1$H-NMR (200 MHz, DMSO-$d_6$), δ (ppm) 3.01-3.18 (m, 4H); 4.85-4.98 (m, 2H); 7.06-7.17 (m, 4H); 7.43-7.58 (m, 4H); 7.91 (s, 2H); 8.46 (d, 6.6 Hz, 2H); 8.65 (s, 2H). LCMS m/z 663 (M+1).

Example 83

2-(1-Carboxy-2-thiophen-2-yl-ethylamino)-6-chloro-quinoline-3-carboxylic acid

In close analogy to the procedure described in Example 1, 2,6-dichloroquinoline-3-carboxylic acid is reacted with 2-amino-3-thiophen-2-yl-propionic acid to provide the title compound in good yield.
Mp >250° C. (decomp.). $^1$H-NMR (200 MHz, DMSO-$d_6$), δ (ppm) 3.40-3.71 (m, 2H); 4.99-5.05 (m, 1H); 6.85-6.94 (m, 2H); 7.15 (d, 5.2 Hz, 1H); 7.50-7.64 (m, 2H); 7.76 (d, 2.0 Hz, 1H); 8.67 (s, 1H). LCMS m/z 377 (M+1).

Example 84

2-(1-Carbamoyl-2-phenyl-ethylamino)-6-chloro-quinoline-3-carboxylic acid

In close analogy to the procedure described in Example 32, 2,6-dichloroquinoline-3-carboxylic acid is reacted with 2-amino-3-phenyl-propionamide to provide the title compound in good yield. LCMS m/z 370 (M+1). $^1$H-NMR (400 MHz, DMSO-$d_6$), δ (ppm) 3.02-3.07 (m, 1H); 3.17-3.22 (m, 1H); 4.90-4.95 (m, 1H); 7.09-7.24 (m, 6H); 7.49-7.62 (m, 3H); 7.96 (d, 2.4 Hz, 1H); 8.52 (d, 6.4 Hz, 1H); 8.72 (s, 1H).

Example 85

6-Chloro-2-(1-methylcarbamoyl-2-phenyl-ethylamino)-quinoline-3-carboxylic acid

In close analogy to the procedure described in Example 32, 2,6-dichloroquinoline-3-carboxylic acid is reacted with 2-amino-N-methyl-3-phenyl-propionamide to provide the title compound in good yield. LCMS m/z 384 (M+1).

Example 86

6,8-Dichloro-2-(1-methylcarbamoyl-2-phenyl-ethylamino)-quinoline-3-carboxylic acid In close analogy to the procedure described in Example 32, 2,6,8-trichloroquinoline-3-carboxylic acid is reacted with 2-amino-N-methyl-3-phenyl-propionamide to provide the title compound in moderate yield.
LCMS m/z 418 (M+1).

Example 87

2-(2-Benzoylamino-1-carboxy-ethylamino)-6-chloro-quinoline-3-carboxylic acid

In close analogy to the procedure described in Example 32, 2,6-dichloroquinoline-3-carboxylic acid is reacted with 2-amino-3-benzoylamino-propionic acid to provide the title compound in good yield.
LCMS m/z 414 (M+1).

Example 88

6,8-Dichloro-2-(2-hydroxy-1-phenylcarbamoyl-ethylamino)-quinoline-3-carboxylic acid In close analogy to the procedure described in Example 32, 2,6,8-trichloroquinoline-3-carboxylic acid is reacted with 3-amino-N-phenyl-succinamic acid to provide the title compound in good yield. LCMS m/z 420 (M+1).

Example 89

2-(1-Carboxy-2-phenylacetylamino-ethylamino)-6-chloro-quinoline-3-carboxylic acid In close analogy to the procedure described in Example 32, 2,6-dichloroquinoline-3-carboxylic acid is reacted with 2-amino-3-phenylacetylamino-propionic acid to provide the title compound in low yield.
LCMS m/z 428 (M+1).

Example 90

2-[1-[1-Carboxy-2-(2-methoxy-phenyl)-ethylcarbamoyl]-2-(2-methoxy-phenyl)-ethylamino]-6-chloro-quinoline-3-carboxylic acid Chromatographical separation of the crude product from Example 72 is continued to provide the title compound in moderate yield.
Mp 181-196° C. (decomp.) $^1$H-NMR (200 MHz, DMSO-$d_6$), $\delta$ (ppm) 2.84-3.08 (m, 4H); 3.57 (s, 3H); 3.76 (s, 3H); 4.60-4.70 (m, 2H); 6.69-6.82 (m, 3H); 6.92 (d, 7.6 Hz, 1H); 7.05-7.19 (m, 4H); 7.38 (d, 8.6 Hz, 1H); 7.47-7.53 (m, 1H); 7.70 (d, 2.6 Hz, 1H); 8.18-8.24 (m, 2H); 8.83 (d, 7.6 Hz, 1H). LCMS m/z 578 (M+1).

Example 91

2-[1-[1-Carboxy-2-(2-chloro-5-methoxy-phenyl)-ethylcarbamoyl]-2-(2-chloro-5-methoxy-phenyl)-ethylamino]-6-chloro-quinoline-3-carboxylic acid Chromatographical separation of the crude product from Example 68 is continued to provide the title compound in moderate yield.
Mp 220-227° C. $^1$H-NMR (200 MHz, DMSO-$d_6$), $\delta$ (ppm) 3.03-3.40 (m, 4H); 3.63 (s, 3H); 3.66 (s, 3H); 4.65-4.80 (m, 1H); 4.88-5.00 (m, 1H); 6.70-6.83 (m, 2H); 6.90 (d, 3.0 Hz, 1H); 7.02 (d, 3.0 Hz, 1H); 7.20 (d, 8.8 Hz, 1H); 7.31 (d, 8.8 Hz, 1H); 7.42-7.60 (m, 2H); 7.71 (d, 2.0 Hz, 1H); 8.31-8.37 (m, 2H); 9.10 (d, 7.6 Hz, 1H). LCMS m/z 646 (M+1).

Example 92

2-[(1-Carboxy-2-thiophen-2-yl-ethylcarbamoyl)-2-thiophen-2-yl-ethylamino]-6-chloro-quinoline-3-carboxylic acid Chromatographical separation of the crude product from Example 83 is continued to provide the title compound in moderate yield.
Mp 210-215° C. $^1$H-NMR (200 MHz, DMSO-$d_6$), $\delta$ (ppm) 3.20-3.55 (m, 4H); 4.55-4.70 (m, 1H); 4.90-5.00 (m, 1H); 6.82-6.95 (m, 4H); 7.27-7.35 (m, 2H); 7.51-7.59 (m, 2H); 7.62 (d, 2.0 Hz, 1H); 8.42-8.44 (m, 2H); 9.16 (d, 7.6 Hz, 1H). LCMS m/z 530 (M+1).

Example 93

2-[1-Carboxy-2-(3-carboxy-phenyl)-ethylamino]-6-chloro-quinoline-3-carboxylic acid Chromatographical separation of the crude product from Example 60 is continued to provide the title compound in low yield.
Mp >250° C. (decomp.) $^1$H-NMR (200 MHz, DMSO-$d_6$), $\delta$ (ppm) 3.20-3.50 (m, 2H); 5.16 (t, 5.8 Hz, 1H); 7.30-7.68 (m, 5H); 7.75-7.85 (m, 2H); 7.94 (br s, 1H); 8.70 (s, 1H). LCMS m/z 415 (M+1).

Example 94

2-[1-[1-Carboxy-2-(4-phenylethynyl-phenyl)-ethylcarbamoyl]-2-(4-phenylethynyl-phenyl)-ethylamino]-6-chloro-quinoline-3-carboxylic acid Chromatographical separation of the crude product from Example 62 is continued to provide the title compound in moderate yield.
Mp 210-218° C. $^1$H-NMR (200 MHz, DMSO-$d_6$), $\delta$ (ppm) 3.00-3.30 (m, 4H); 4.62-4.74 (m, 1H); 4.88-4.98 (m, 1H); 7.19 (d, 7.8 Hz, 2H); 7.35-7.61 (m, 18H); 7.82 (d, 1.8 Hz, 1H); 8.24 (d, 7.0 Hz, 1H); 8.35 (s, 1H); 9.09 (d, 9.0 Hz, 1H). LCMS m/z 718 (M+1).

Example 95

2-(1-Carboxy-2-phenyl-ethylamino)-6-chloro-8-methylquinoline-3-carboxylic acid

In close analogy to the procedure described in Example 1, 2,6-dichloro-8-methyl-quinoline-3-carboxylic acid ethyl ester is reacted with DL-phenylalanine to provide the title compound in moderate yield as yellow powder.
Mp >145° C. (decomp.) $^1$H-NMR (200 MHz, DMSO-$d_6$), $\delta$ (ppm) 3.06-3.17 (m, 1H); 3.24-3.34 (m, 1H); 4.77-4.90 (m, 1H); 7.35-7.60 (m, 5H); 7.48 (br s, 1H); 7.77 (br s, 1H); 8.64 (s, 1H); 8.86 (br s, 1H). LCMS m/z 383 (M−1).

Example 96

2-{1-Carboxy-2-[4-(quinolin-2-yloxy)-phenyl]-ethylamino}-6-chloro-quinoline-3-carboxylic acid A mixture of 2-[1-carboxy-2-(4-hydroxy-phenyl)-ethylamino]-6-chloro-quinoline-3-carboxylic acid (114 mg, 0.294 mmol) (prepared according to the procedure described in Example 34), sodium hydride (60% oil dispersion; 65 mg, 1.44 mmol) and 2-chloroquinoline (118 mg, 0.72 mmol) in dry DMF (1 mL) is stirred for 40 h at 110° C. in closed reaction vial. After cooling, the reaction mixture is poured in water and acidified by aqueous HCl. Precipitate is filtered, washed with water, then with hexane. The residue is treated with methanol and filtered. Filtrate is concentrated under reduced pressure, water is added and the precipitate is recrystallized from a mixture of acetone-water, 4:1, to provide the title compound in low yield.
Mp 136° C. $^1$H-NMR (200 MHz, DMSO-$d_6$), $\delta$ (ppm) 3.19-3.37 (m, 2H); 4.94-5.07 (m, 1H); 7.12-7.65 (m, 10H);

7.89-7.99 (m, 2H); 8.36 (d, 9.8 Hz, 1H); 8.62 (br d, 1H); 8.76 (s, 1H). LCMS m/z 514 (M+1).

Example 97

2-[1-Carboxy-2-(1H-indol-3-yl)-ethylamino]-6-chloro-8-methylquinoline-3-carboxylic acid In close analogy to the procedure described in Example 32, 2,6-dichloro-8-methyl-quinoline-3-carboxylic acid ethyl ester is reacted with DL-tryptophan to provide 2-[1-carboxy-2-(1H-indol-3-yl)-ethylamino]-6-chloro-8-methyl-quinoline-3-carboxylic acid ethyl ester. The ester (107 mg, 0.24 mmol) is dissolved in THF (2 mL), then 0.7M aqueous NaOH (1 mL) is added and the mixture is stirred at rt for 23 h. The mixture is concentrated under reduced pressure treated with water and filtered. The filtrate is acidified by addition of 3N HCl till pH 2-3, and stirred for 40 min. Precipitate is filtered off and washed with cold water to provide after drying the title compound (55 mg, 61%) as pale green powder.
Mp >160° C. (decomp.) $^1$H-NMR (200 MHz, DMSO-$d_6$), δ (ppm) 3.23-3.50 (m, 2H); 4.86-4.95 (m, 1H); 6.90-7.08 (m, 2H); 7.19 (s, 1H); 7.32 (d, 7.8 Hz, 1H); 7.47-7.51 (m, 2H); 7.81 (s, 1H); 8.57 (br d, 1H); 8.69 (s, 1H); 10.92 (s, 1H). LCMS m/z 422 (M−1).

Example 98

2-[1-Carboxy-2-(3-fluoro-phenyl)-ethylamino]-6-chloro-quinoline-3-carboxylic acid In close analogy to the procedure described in Example 32, 2,6-dichloro-quinoline-3-carboxylic acid is reacted with 3-fluoro-DL-phenylalanine in DMSO to provide the title compound in high yield.
Mp 177-181° C. $^1$H-NMR (200 MHz, DMSO-$d_6$), δ (ppm) 3.11-3.27 (m, 2H); 4.95-5.04 (m, 1H); 6.98-7.07 (m, 3H); 7.24-7.35 (m, 1H); 7.49-7.64 (m, 2H); 7.99 (d, 1.8 Hz, 1H); 8.49 (d, 6.8 Hz, 1H); 8.76 (s, 1H). LCMS m/z 389 (M+1).

Example 99

2-(1-Carboxy-2-pyridin-3-yl-ethylamino)-6-chloro-quinoline-3-carboxylic acid

In close analogy to the procedure described in Example 32, 2,6-dichloro-quinoline-3-carboxylic acid is reacted with 2-amino-3-pyridin-3-yl-propionic acid in DMSO to provide the title compound in good yield.
Mp >170° C. (decomp.) $^1$H-NMR (200 MHz, DMSO-$d_6$), δ (ppm) 3.14-3.39 (m, 2H); 5.00-5.09 (m, 1H); 7.33-7.40 (m, 1H); 7.42-7.75 (m, 3H); 7.99 (d, 2.0 Hz, 1H); 8.42-8.55 (m, 3H); 8.76 (s, 1H). LCMS m/z 372 (M+1).

Example 100

2-{(S)-1-Carboxy-2-[4-(3-carboxy-pyridin-2-yloxy)-phenyl]-ethylamino}-6-chloro-quinoline-3-carboxylic acid In close analogy to the procedure described in Example 96, 2-[1-carboxy-2-(4-hydroxy-phenyl)-ethylamino]-6-chloro-quinoline-3-carboxylic acid is reacted with 2-chloronicotinic acid to provide the title compound in a form of diammonia salt after chromatography on silica (aq. ammonia containing eluent).
Mp >166° C. (decomp.) $^1$H-NMR (200 MHz, DMSO-$d_6$), δ (ppm) 3.05-3.26 (m, 2H); 4.79-4.92 (m, 1H); 6.90-7.00 (m, 2H); 7.12-7.30 (m, 3H); 7.46 (s, 2H); 7.83 (s, 1H); 8.13-8.21 (m, 2H); 8.53 (s, 1H); 9.95 (br d, 1H). LCMS m/z 508 (M+1).

Example 101

2-{(S)-2-[4-(5-Bromo-pyridin-2-yloxy)-phenyl]-1-carboxy-ethylamino}-6-chloro-quinoline-3-carboxylic acid In close analogy to the procedure described in Example 32; 2,6-dichloro-quinoline-3-carboxylic acid is reacted with (S)-2-amino-3-[4-(5-bromo-pyridin-2-yloxy)-phenyl]-propionic acid in DMSO to provide the title compound in good yield.
Mp 145-150° C.; LCMS m/z 543 (M+1).

Example 102

6-Bromo-2-[1-carboxy-2-(4-hydroxy-phenyl)-ethylamino]-quinoline-3-carboxylic acid In close analogy to the procedure described in Example 1, 6-bromo-2-chloroquinoline-3-carboxylic acid is reacted with DL-tyrosine in DMSO to provide the title compound in good yield.
$^1$H-NMR (200 MHz, DMSO-$d_6$), δ (ppm) 3.00-3.15 (m, 2H); 4.83-4.90 (m, 1H); 6.65 (d, 8 Hz, 2H); 7.00 (d, 8 Hz, 2H); 7.74 (d, 8 Hz, 1H); 7.71 (d, 8 Hz, 1H); 8.12 (s, 1H); 8.55 (br s, 1H); 8.74 (s, 1H); 9.24 (s, 1H).

Example 103

6-Bromo-2-{1-carboxy-2-[4-(3-carboxy-quinolin-2-yloxy)-phenyl]-ethylamino}-quinoline-3-carboxylic acid In close analogy to the procedure described in Example 96, 6-bromo-2-[1-carboxy-2-(4-hydroxy-phenyl)-ethylamino]-quinoline-3-carboxylic acid is reacted with 2-chloro-quinoline-3-carboxylic acid to provide the title compound in good yield.
$^1$H-NMR (200 MHz, DMSO-$d_6$), δ (ppm) 3.10-3.30 (m, 2H); 4.80-4.85 (m, 1H); 7.01 (d, 8.0 Hz, 2H); 7.25-7.55 (m, 7H); 7.85-7.95 (m, 2H); 8.32 (s, 1H); 8.42 (s, 1H); 10.42 (d, 5.2 Hz, 1H).

Example 104

2-{1-Carboxy-2-[4-(quinolin-4-ylamino)-phenyl]-ethylamino}-6-chloro-quinoline-3-carboxylic acid a)
2-Amino-3-[4-(quinolin-4-ylamino)-phenyl]propionic acid dihydrochloride dihydrate A mixture of 2-amino-3-(4-aminophenyl)-propionic acid hydrate (0.27 g, 1.5 mmol), 4-chloro-quinoline (0.245 g, 1.5 mmol) and conc. HCl (0.43 g) in dioxane (3 mL) is stirred at 120° C. temperature for 30 min in a tightly closed Pierce glass reaction vial. After cooling the liquid phase is separated and the solid residue is washed with acetonitrile (3×3 mL) and diethyl ether (5 mL) to give the title compound (0.405 g, 65%) as yellow solid.
Mp >250° C. (decomp.) $^1$H NMR (200 MHz, DMSO-$d_6$); δ (ppm) 3.15-3.26 (m, 2H); 4.15-4.25 (m, 1H); 6.80 (d, 6.8 Hz, 1H); 7.30-7.50 (m, 4H); 7.78 (t, 8 Hz, 1H); 8.02 (t, 8 Hz, 1H); 8.15 (d, 8.8 Hz, 1H); 8.50-8.70 (m, 4H); 8.95 (d, 7.6 Hz, 1H); 11.21 (d, 8.8 Hz, 1H). LC/MS (307.8, M+).

b) 2-{1-Carboxy-2-[4-(quinolin-4-ylamino)-phenyl]-ethylamino}-6-chloro-quinoline-3-carboxylic acid A mixture of 2,6-dichloro-quinoline-3-carboxylic acid (0.17 g, 0.7 mmol), 2-amino-3-[4-(quinolin-4-ylamino)-phenyl]propionic acid dihydrochloride dihydrate (0.291 g, 0.7 mmol) and $K_2CO_3$ (0.507 g, 3.7 mmol) in DMSO (1.5 mL) is stirred at 110° C. temperature for 24 h in a Pierce reaction vial. After cooling the reaction mixture is diluted with water (10 mL) and acidified with 2N aqueous HCl till pH ~3. The precipitated solid is collected on filter and washed with water to give the title compound (0.3 g, 84%) as yellow solid.

Mp >200° C. (decomp.). $^1$H-NMR (400 MHz, DMSO-$d_6$), δ (ppm) 3.16-3.22 (m, 1H); 3.31-3.36 (m, 1H); 5.01-5.06 (m, 1H); 6.70 (d, 5.6 Hz, 1H); 7.30 (d, 8.4 Hz, 2H); 7.37 (d, 7.6 Hz, 2H); 7.51-7.66 (m, 3H); 7.83-7.96 (m, 3H); 8.43 (d, 6.4 Hz, 1H); 8.51 (d, 8.8 Hz, 1H); 8.72 (s, 1H); 8.97 (br s, 1H); 9.90 (br s, 1H). LC/MS (512.8, M+).

Example 105

2-{1-Carboxy-2-[4-(3-carboxy-pyridin-2-ylamino)-phenyl]-ethylamino}-6-chloro-quinoline-3-carboxylic acid In close analogy to the procedure described in Example 104b, 2,6-dichloroquinoline-3-carboxylic acid is reacted with 2-{[4-(2-amino-2-carboxyethyl)phenyl]amino}pyridine-3-carboxylic acid (prepared by reaction of 2-amino-3-(4-aminophenyl)-propionic acid with 2-chloronicotinic acid as in Example 104a) to provide the title compound in good yield.

$^1$H-NMR (400 MHz, DMSO-$d_6$), δ (ppm) 3.04-3.10 (m, 1H); 3.18-3.25 (m, 1H); 4.89-4.93 (m, 1H); 6.76-6.79 (m, 1H); 7.18 (d, 8.8 Hz, 2H); 7.49-7.57 (m, 2H); 7.62 (d, 8.4 Hz, 2H); 7.93 (s, 1H); 8.20 (d, 7.6 Hz, 1H); 8.28 (d, 6.8 Hz, 1H); 8.67 (s, 1H); 9.12 (br s, 1H); 11.38 (br s, 1H).

Example 106

2-{1-Carboxy-2-[4-(7-chloro-quinolin-4-ylamino)-phenyl]-ethylamino}-6-chloro-quinoline-3-carboxylic acid In close analogy to the procedure described in Example 104b, 2,6-dichloroquinoline-3-carboxylic acid is reacted with 2-amino-3-[4-(7-chloro-quinolin-4-ylamino)-phenyl]-propionic acid (prepared by reaction of 2-amino-3-(4-aminophenyl)-propionic acid with 4,7-dichloro-quinoline as in Example 104a) to provide the title compound in good yield.

$^1$H-NMR (400 MHz, DMSO-$d_6$), δ (ppm) 3.13-3.18 (m, 1H); 3.29-3.33 (m, 1H); 5.00-5.05 (m, 1H); 6.73 (d, 5.6 Hz, 1H); 7.25 (d, 8.4 Hz, 2H); 7.31 (d, 8.0 Hz, 2H); 7.51-7.60 (m, 3H); 7.90 (s, 1H); 7.96 (s, 1H); 8.39-8.43 (m, 2H); 8.73 (s, 1H); 8.89 (br s, 1H); 9.26 (br s, 1H).

Example 107

2-{1-Carboxy-2-[3-(3-carboxy-6-bromo-quinolin-2-yloxy)-phenyl]-ethylamino}-6-bromo-quinoline-3-carboxylic acid In close analogy to the procedure described in Example 96, 6-bromo-2-[1-carboxy-2-(4-hydroxy-phenyl)-ethylamino]-quinoline-3-carboxylic acid is reacted with 6-bromo-2-chloro-quinoline-3-carboxylic acid ethyl ester to provide the title compound in good yield.

$^1$H-NMR (200 MHz, DMSO-$d_6$), δ (ppm) 3.10-3.30 (m, 2H); 4.83-4.88 (m, 1H); 7.05 (d, 8.2 Hz, 2H); 7.29-7.68 (m, 6H); 7.92 (s, 1H); 8.20 (s, 1H); 8.31 (s, 1H); 8.44 (s, 1H); 10.52 (br s, 1H).

Example 108

2-{1-Carboxy-2-[4-(quinolin-2-ylamino)-phenyl]-ethylamino}-6-chloro-quinoline-3-carboxylic acid In close analogy to the procedure described in Example 104b, 2,6-dichloroquinoline-3-carboxylic acid is reacted with 2-amino-3-[4-(quinolin-2-ylamino)-phenyl]-propionic acid (prepared by reaction of 2-amino-3-(4-aminophenyl)-propionic acid with 2-chloro-quinoline as in Example 104a) to provide the title compound in good yield.

$^1$H-NMR (400 MHz, DMSO-$d_6$), δ (ppm) 3.03-3.08 (m, 1H); 3.17-3.22 (m, 1H); 4.86-4.90 (m, 1H); 7.02 (d, 8.0 Hz, 1H); 7.20-7.28 (m, 3H); 7.46-7.56 (m, 3H); 7.66-7.70 (m, 2H); 7.87-7.89 (m, 3H); 8.01 (d, 9.6 Hz, 1H); 8.58 (s, 1H); 9.35 (s, 1H); 9.71 (br s, 1H).

Example 109

2-{(S)-1-Carboxy-2-[4-(quinolin-4-yloxy)-phenyl]-ethylamino}-6-chloro-quinoline-3-carboxylic acid a) (S)-3-[4-(quinolin-4-yloxy)-phenyl]-2-tert-butoxycarbonylamino-propionic acid N-Boc-L-Tyrosine (0.844 g, 3 mmol) and KOBu-t (0.727 g, 6.5 mmol) are dissolved in dry DMSO (2.9 mL) under argon atmosphere in a tightly closed glass reaction tube and stirred for 15 min, then 4-chloroquinoline (0.491 g, 3 mmol) is added. The mixture is stirred for 6 days at 30° C. When only traces of 5-bromo-2-chloropyridine are detected (LC-MS control), the reaction mixture is poured into water (40 mL) and the aqueous phase is washed with diethyl ether (2×20 mL). The pH of aqueous phase is adjusted to ~4 by adding 20% aqueous citric acid. The product precipitated is collected on filter and washed with water (50 mL) to give the title compound (0.833 g, 68%) as a grey solid.

LC-MS: 437.4 [M+H].

b) (S)-2-Amino-3-[4-(quinolin-4-yloxy)-phenyl]-propionic acid

Trifluoroacetic acid (5.5 g) is added dropwise to a stirred suspension of (S)-3-[4-(quinolin-4-yloxy)-phenyl]-2-tert-butoxycarbonylamino-propionic acid (0.76 g, 1.88 mmol) in THF (2 mL) while cooling with an ice bath. The mixture is stirred at rt for 3 days, then it is concentrated under reduced pressure. The residue is treated with ethyl ether to give the title compound (0.692 g, 87%) as a trifluoroacetic acid salt.

LC-MS: 309 [M+H]. $^1$H NMR (400 MHz, DMSO-$d_6$); δ (ppm) 3.12-3.26 (m, 2H); 4.26 (m, 1H); 6.80 (d, 5.6 Hz, 1H); 7.35 (d, 8.4 Hz, 2H); 7.46 (d, 8.4 Hz, 2H); 7.83 (t, 8 Hz, 1H); 8.02 (t, 8 Hz, 1H); 8.6 (d, 8.4. Hz, 1H); 8.37 (br s, 3H); 8.44 (d, 8.8 Hz, 1H); 8.91 (d, 5.6 Hz, 1H).

c) 2-{(S)-2-[4-(Quinolin-4-yloxy)-phenyl]-1-carboxy-ethylamino}-6-chloro-quinoline-3-carboxylic acid A mixture of trifluoroacetic acid salt of (S)-2-amino-3-[4-(quinolin-4-yloxy)-phenyl]-propionic acid (0.296 g, 0.7 mmol), 2,6-dichloroquinoline-3-carboxylic acid (0.16 g, 0.66 mmol) and K$_2$CO$_3$ (0.46 g, 3.3 mmol) in dry DMSO (1 mL) is stirred for 13 h in a closed Pierce reaction vial at 100° C. temperature. After cooling the reaction mixture is diluted with water (25 mL), acidified with 2N aqueous HCl till pH 3, and the precipitated solid is collected on filter. The crude product is washed with water and recrystallized from DMF/EtOH (0.5 mL/0.5 mL) mixture to give the title compound as a yellow solid (0.14 g, 41%).

$^1$H-NMR (400 MHz, DMSO-d$_6$), δ (ppm) 3.15-3.21 (m, 1H); 3.31-3.36 (m, 1H); 5.03-5.08 (m, 1H); 6.40 (d, 5.2 Hz, 1H); 7.17 (d, 8.4 Hz, 2H); 7.39 (d, 8.0 Hz, 2H); 7.51-7.65 (m, 3H); 7.81 (t, 7.0 Hz, 1H); 7.95 (d, 2.4 Hz, 1H); 7.96 (d, 8.8 Hz, 1H); 8.28 (d, 7.6 Hz, 1H); 8.61 (d, 4.8 Hz, 1H); 8.69 (s, 1H); 9.18 (br s, 1H).

Example 110

2-{1-Carboxy-2-[4-(3-carboxy-quinolin-2-yloxy)-phenyl]-ethylamino}-6-chloro-quinoline-3-carboxylic acid In close analogy to the procedure described in Example 32, 2,6-dichloroquinoline-3-carboxylic acid is reacted with 2-[4-(2-amino-2-carboxy-ethyl)-phenoxy]-quinoline-3-carboxylic acid ethyl ester in DMSO to provide, after hydrolysis with aqueous NaOH, the title compound in good yield.

$^1$H-NMR (200 MHz, DMSO-d$_6$), δ (ppm) 3.10-3.30 (m, 2H); 4.80-4.85 (m, 1H); 7.02 (d, 8.3 Hz, 2H); 7.29 (d, 8.3 Hz, 2H); 7.42-7.46 (m, 3H); 7.54-7.56 (m, 2H); 7.77 (s, 1H); 7.91 (d, 8.2 Hz, 1H); 8.30 (s, 1H); 8.42 (s, 1H); 10.55 (br s, 1H).

Example 111

6-Bromo-2-{2-[4-(5-bromo-pyridin-2-yloxy)-phenyl]-1-carboxy-ethylamino}-quinoline-3-carboxylic acid In close analogy to the procedure described in Example 109c, 6-bromo-2-chloroquinoline-3-carboxylic acid is reacted with 2-amino-3-[4-(5-bromo-pyridin-2-yloxy)-phenyl]-propionic acid (prepared by analogy to Example 109a,b) to provide the title compound in moderate yield.

$^1$H-NMR (200 MHz, DMSO-d$_6$), δ (ppm) 3.10-3.30 (m, 2H); 4.81 (br s, 1H); 6.94-7.04 (m, 3H); 7.30-7.36 (m, 3H); 7.51 (d, 8.8 Hz, 1H); 7.90 (s, 1H); 8.01 (d, 8.6 Hz, 1H); 8.25 (s, 1H); 8.40 (s, 1H); 10.75 (br s, 1H).

Example 112

6-Bromo-2-{1-carboxy-2-[4-(quinolin-2-yloxy)-phenyl]-ethylamino}-quinoline-3-carboxylic acid In close analogy to the procedure described in Example 109c, 2,6-dichloroquinoline-3-carboxylic acid is reacted with 2-amino-3-[4-(quinolin-2-yloxy)-phenyl]-propionic acid (prepared by analogy to Example 109a,b) to provide the title compound in good yield.

$^1$H-NMR (200 MHz, DMSO-d$_6$), δ (ppm) 3.10-3.30 (m, 2H); 4.87 (br s, 1H); 7.11-7.21 (m, 4H); 7.35-7.63 (m, 6H); 7.90-7.94 (m, 2H); 8.36 (d, 8.8 Hz, 1H); 8.45 (s, 1H); 10.60 (br s, 1H).

Example 113

2-[2-(4-Bromo-phenyl)-1-carboxy-ethylamino]-6-chloro-quinoline-3-carboxylic acid In close analogy to the procedure described in Example 1, 2,6-dichloroquinoline-3-carboxylic acid is reacted with 2-amino-3-(4-bromo-phenyl)-propionic acid in DMSO to provide the title compound in good yield.

$^1$H-NMR (400 MHz, DMSO-d$_6$), δ (ppm) 3.12-3.18 (m, 1H); 3.26-3.35 (m, 1H); 4.98-5.03 (m, 1H); 7.18 (d, 8.0 Hz, 2H); 7.46 (d, 8.0 Hz, 2H); 7.54 (d, 8.8 Hz, 1H); 7.62 (d, 8.8 Hz, 1H); 7.99 (s, 1H); 8.49 (d, 7.2 Hz, 1H); 8.77 (s, 1H).

Example 114

(S)-2-(3-Carboxy-6-chloro-quinolin-2-ylamino)-succinic acid ammonia hydrate

In close analogy to the procedure described in Example 1, 2,6-dichloroquinoline-3-carboxylic acid is reacted with L-aspartic acid in DMSO to provide the title compound in good yield.

$^1$H-NMR (400 MHz, DMSO-d$_6$), δ (ppm) 2.44-2.67 (m, 2H); 4.64-4.68 (m, 1H); 7.39-7.44 (m, 2H); 7.77 (s, 1H); 8.43 (s, 1H); 10.10 (d, 5.6 Hz, 1H).

Example 115

2-[1-Carboxy-2-(3-fluoro-phenyl)-ethylamino]-6,8-dichloro-quinoline-3-carboxylic acid In close analogy to the procedure described in Example 1, 2,6,8-trichloroquinoline-3-carboxylic acid is reacted with 2-amino-3-(3-fluoro-phenyl)-propionic acid in DMSO to provide the title compound in good yield.

$^1$H-NMR (400 MHz, DMSO-d$_6$), δ (ppm) 3.20-3.25 (m, 1H); 3.34-3.39 (m, 1H); 5.03-5.08 (m, 1H); 7.00-7.08 (m, 3H); 7.27-7.33 (m, 1H); 7.87 (s, 1H); 7.99 (s, 1H); 8.76 (s, 1H); 9.03 (br s, 1H).

Example 116

2-(3-Carboxy-6,8-dichloro-quinolin-2-ylamino)-3-phenyl-succinic acid

In close analogy to the procedure described in Example 1, 2,6,8-trichloroquinoline-3-carboxylic acid is reacted with 2-amino-3-phenyl-succinic acid [*J. Med. Chem.* 1973, 16, 1277-1280.] in DMSO to provide the title compound in good yield.

$^1$H-NMR (400 MHz, DMSO-d$_6$), δ (ppm) 4.48 and 4.53 (d, 4.4 Hz and d, 8.4 Hz, total 1H); 5.49-5.53 (m, 1H); 7.10-7.21 (m, 3H); 7.28-7.34 (m, 2H); 7.83 and 7.90 (d, 2.4 Hz and d, 2.0 Hz, total 1H); 7.95 and 7.97 (d, 2.4 Hz and d, 2.0 Hz, total 1H); 8.70 and 8.75 (both s, total 1H); 8.71 and 9.15 (both br s, total 1H).

Example 117

2-(2-Benzyloxy-1-phenylcarbamoyl-ethylamino)-6-chloro-quinoline-3-carboxylic acid In close analogy to the procedure described in Example 1, 2,6-dichloroquinoline-3-carboxylic acid is reacted with 2-amino-3-benzyloxy-N-phenyl-propionamide (prepared by reaction of N-Boc-O-benzyl-L-serine with aniline in the presence of N-hydroxy-benzotriazole and EDC, followed by deprotection with TFA) in DMSO to provide the title compound in good yield.

Mp 150-151° C. $^1$H-NMR (200 MHz, DMSO-d$_6$), δ (ppm) 3.70-3.95 (m, 2H); 4.58 (s, 2H); 5.09-5.14 (m, 1H); 7.04 (t, 7.6 Hz, 1H); 7.20-7.40 (m, 8H); 7.42-7.54 (m, 2H); 7.63 (d, 8.0 Hz, 2H); 7.89 (s, 1H); 8.61 (s, 1H); 10.24 (s, 1H). LCMS m/z 476 (M$^+$).

Example 118

2-[(S)-1-Carboxy-2-(4-hydroxy-phenyl)-ethylamino]-6,8-dichloro-quinoline-3-carboxylic acid In close analogy to the procedure described in Example 1, 2,6,8-trichloroquinoline-3-carboxylic acid is reacted with L-tyrosine in H$_2$O to provide the title compound in good yield.

$^1$H-NMR (400 MHz, DMSO-d$_6$), δ (ppm) 3.04-3.09 (m, 1H); 3.20-3.25 (m, 1H); 4.92-4.97 (m, 1H); 6.65 (d, 8.4 Hz, 2H); 7.01 (d, 8.4 Hz, 2H); 7.90 (s, 1H); 8.01 (s, 1H); 8.63 (d, 6.4 Hz, 1H); 8.80 (s, 1H); 9.22 (br s, 1H).

Example 119

2-(3-Carboxy-6-chloro-quinolin-2-ylamino)-3-(3-fluoro-phenyl)-succinic acid

In close analogy to the procedure described in Example 1, 2,6-dichloroquinoline-3-carboxylic acid is reacted with 2-amino-3-(3-fluoro-phenyl)-succinic acid [prepared by analogy to J. Med. Chem. 1973, 16, 1277-1280.; using alkylation of diethyl acetamidomalonate by methyl bromo-(3-fluoro-phenyl)-acetate] in DMSO to provide the title compound in good yield.

$^1$H-NMR (400 MHz, DMSO-d$_6$), δ (ppm) 4.40-4.50 (m, 1H); 5.51-5.55 (m, 1H); 6.95-7.02 (m, 1H); 7.16-7.26 (m, 3H); 7.40 and 7.65 (both d, 9.2 Hz, total 1H); 7.55-7.58 (m, 1H); 7.94-7.98 (m, 1H); 8.45 and 8.96 (both d, 8.8 Hz, total 1H); 8.70 and 8.73 (both s, total 1H).

Example 120

2-((S)-1-Carboxy-2-phenyl-ethylamino)-6,8-dimethyl-quinoline-3-carboxylic acid

In close analogy to the procedure described in Example 1, 2-chloro-6,8-dimethyl-quinoline-3-carboxylic acid is reacted with L-phenylalanine in DMSO to provide the title compound in good yield. LCMS m/z 364 (M$^+$).

Example 121

2-(2-Benzylcarbamoyl-1-carboxy-ethylamino)-6-chloro-quinoline-3-carboxylic acid

In close analogy to the procedure described in Example 1, 2,6-dichloroquinoline-3-carboxylic acid is reacted with 2-amino-N-benzyl-succinamic acid [J. Pharm. Sci. 1980, 69 (5), 553-555.] in DMF to provide the title compound in good yield.

$^1$H-NMR (200 MHz, DMSO-d$_6$), δ (ppm) 2.80-2.90 (m, 2H); 4.26 (d, 3.6 Hz, 2H); 5.08-5.15 (m, 1H); 7.15-7.30 (m, 5H); 7.49-7.64 (m, 2H); 8.01 (s, 1H); 8.51 (br s, 1H); 8.73-8.79 (m, 2H).

Example 122

2-{(S)-1-Carboxy-2-[4-(3-carboxy-6,8-dichloro-quinolin-2-yloxy)-phenyl]-ethylamino}-6,8-dichloro-quinoline-3-carboxylic acid In close analogy to the procedure described in Example 1, 2,6,8-trichloroquinoline-3-carboxylic acid is reacted with N-Boc-L-tyrosine in H$_2$O to provide the title compound in good yield.

$^1$H-NMR (400 MHz, DMSO-d$_6$), δ (ppm) 3.24-3.29 (m, 1H); 3.41-3.46 (m, 1H); 5.04-5.09 (m, 1H); 6.65 (d, 8.8 Hz, 2H); 7.01 (d, 8.4 Hz, 2H); 7.90 (s, 1H); 7.99 (s, 1H); 8.01 (s, 1H); 8.20 (s, 1H); 8.71 (d, 7.2 Hz, 1H); 8.81 (s, 1H); 8.90 (s, 1H).

Example 123

2-[(S)-1-Carboxy-2-(1-methyl-1H-indol-3-yl)-ethylamino]-6,8-dichloro-quinoline-3-carboxylic acid In close analogy to the procedure described in Example 1, 2,6,8-trichloroquinoline-3-carboxylic acid is reacted with N-methyl-L-tryptophan in DMSO to provide the title compound in good yield.

$^1$H-NMR (400 MHz, DMSO-d$_6$), δ (ppm) 3.31-3.36 (m, 1H); 3.45-3.50 (m, 1H); 3.72 (s, 3H); 5.00-5.05 (m, 1H); 6.94-6.98 (m, 1H); 7.09-7.13 (m, 1H); 7.16 (s, 1H); 7.36 (d, 8.0 Hz, 1H); 7.50 (d, 8.0 Hz, 1H); 7.89 (d, 2.0 Hz, 1H); 8.00 (s, 1H); 8.77 (s, 1H); 8.90 (d, 5.2 Hz, 1H).

Example 124

2-{(S)-1-Carboxy-2-[4-(6-chloro-quinolin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(6-chloro-quinolin-2-yloxy)-phenyl]-propionic acid (prepared by analogy to Example 109a,b) in DMSO to provide the title compound in good yield.

$^1$H-NMR (400 MHz, DMSO-d$_6$), δ (ppm) 3.16-3.22 (m, 2H); 5.00-5.05 (m, 1H); 7.05-7.15 (m, 2H); 7.27-7.35 (m, 2H); 7.53-7.62 (m, 4H); 7.98 (d, 2.0 Hz, 2H); 8.08 (s, 1H); 8.37 (d, 9.2 Hz, 1H); 8.74 (s, 1H); 8.75-8.95 (br s, 1H).

Example 125

2-{(S)-1-Carboxy-2-[4-(8-chloro-quinolin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(8-chloro-quinolin-2-yloxy)-phenyl]-propionic acid (prepared by analogy to Example 109a,b) in DMSO to provide the title compound in good yield.

$^1$H-NMR (400 MHz, DMSO-d$_6$), δ (ppm) 3.17-3.22 (m, 1H); 3.32-3.37 (m, 1H); 5.00-5.04 (m, 1H); 7.10-7.60 (m, 5H); 7.70-8.00 (m, 4H); 8.44 (d, 8.8 Hz, 1H); 8.68 (br s, 1H); 8.76 (s, 1H).

Example 126

2-{(S)-1-Carboxy-2-[4-(3-chloro-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3-chloro-pyridin-2-yloxy)-phenyl]-propionic acid (prepared by analogy to Example 109a,b) in DMSO to provide the title compound in good yield.

$^1$H-NMR (400 MHz, DMSO-d$_6$), δ (ppm) 3.14-3.20 (m, 1H); 3.28-3.32 (m, 1H); 4.97-5.01 (m, 1H); 7.06 (d, 8.4 Hz, 2H); 7.13-7.17 (m, 1H); 7.29 (d, 8.4 Hz, 2H); 7.53-7.62 (m, 2H); 7.98-8.06 (m, 3H); 8.70 (d, 6.4 Hz, 1H); 8.76 (s, 1H).

Example 127

2-{(S)-1-Carboxy-2-[4-(5-trifluoromethyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-trifluoromethyl-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 3.13-3.18 (m, 1H); 3.28-3.33 (m, 1H); 4.96-5.01 (m, 1H); 6.95-7.15 (m, 3H); 7.32 (d, 8.8 Hz, 2H); 7.50-7.60 (m, 2H); 7.96 (s, 1H); 8.18 (d, 9.2 Hz, 1H); 8.54 (s, 1H); 8.72 (s, 1H); 8.99 (br s, 1H).

Example 128

2-{(S)-1-Carboxy-2-[4-(5-chloro-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-chloro-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 3.13-3.18 (m, 1H); 3.27-3.31 (m, 1H); 4.97-5.01 (m, 1H); 7.00-7.10 (m, 3H); 7.28 (d, 8.4 Hz, 2H); 7.52-7.62 (m, 2H); 7.90-7.99 (m, 2H); 8.18 (s, 1H); 8.62 (d, 6.4 Hz, 1H); 8.76 (s, 1H).

Example 129

2-{(S)-1-Carboxy-2-[4-(3-trifluoromethyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3-trifluoromethyl-pyridin-2-yloxy)-phenyl]-propionic acid (prepared by analogy to Example 109a,b) in DMSO to provide the title compound in good yield.
$^1$H-NMR (200 MHz, DMSO-$d_6$), δ (ppm) 3.10-3.20 (m, 2H); 4.90-5.00 (m, 1H); 7.07 (d, 8.0 Hz, 2H); 7.25-7.40 (m, 3H); 7.50-7.65 (m, 2H); 7.96 (s, 1H); 8.24 (d, 6.6 Hz, 1H); 8.36 (d, 4.2 Hz, 1H); 8.72 (s, 1H); 8.85-9.05 (br s, 1H).

Example 130

2-{(S)-1-Carboxy-2-[4-(5-phenyl-[1,6]naphthyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-phenyl-[1,6]naphthyridin-2-yloxy)-phenyl]-propionic acid (prepared by analogy to Example 109a,b, arylating N-Boc-L-tyrosine with 2-chloro-5-phenyl-[1,6]naphthyridine which obtained by a common POCl$_3$ procedure from 5-phenyl-1H-[1,6]naphthyridin-2-one [*J. Heterocycl. Chem.* 1990, 27 (7), 2085-2091]) in DMSO to provide the title compound in good yield.
$^1$H-NMR (200 MHz, DMSO-$d_6$), δ (ppm) 3.10-3.20 (m, 2H); 4.90-5.00 (m, 1H); 7.17-7.80 (m, 15H); 8.36 (d, 8.8 Hz, 1H); 8.46 (s, 1H); 8.65 (d, 6.4 Hz, 1H).

Example 131

2-{1-Carboxy-2-[4-(5-iodo-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-iodo-pyridin-2-yloxy)-phenyl]-propionic acid (prepared by analogy to Example 109a,b) in DMSO to provide the title compound in good yield.
$^1$H-NMR (200 MHz, DMSO-$d_6$), δ (ppm) 3.05-3.35 (m, 2H); 4.92-5.00 (m, 1H); 6.84 (d, 8.2 Hz, 1H); 7.03 (d, 8.0 Hz, 2H); 7.28 (d, 7.8 Hz, 2H); 7.48-7.61 (m, 2H); 7.96 (s, 1H); 8.10 (d, 6.6 Hz, 1H); 8.33 (s, 1H); 8.72 (s, 1H); 8.91 (d, 5.2 Hz, 1H).

Example 132

6-Chloro-2-[(S)-1-(2-methoxy-ethoxycarbonyl)-2-phenyl-ethylamino]-quinoline-3-carboxylic acid In close analogy to the procedure described in Example 43, 2,6-dichloro-quinoline-3-carboxylic acid is reacted with (S)-2-amino-3-phenyl-propionic acid 2-methoxy-ethyl ester to provide after chromatographical separation the title compound in moderate yield.
LCMS m/z 429 (M+1).

Example 133

2-{(S)-1-Carboxy-2-[4-(5-methyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-methyl-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 2.23 (s, 3H); 3.12-3.17 (m, 1H); 3.25-3.30 (m, 1H); 4.96-5.01 (m, 1H); 6.85 (d, 8.4 Hz, 1H); 6.98 (d, 8.4 Hz, 2H); 7.26 (d, 8.8 Hz, 2H); 7.54 (d, 8.8 Hz, 1H); 7.61-7.65 (m, 2H); 7.96 (s, 1H); 8.00 (s, 1H); 8.66 (br s, 1H); 8.76 (s, 1H).

Example 134

2-{(S)-1-Carboxy-2-[4-(4-methyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(4-methyl-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 2.30 (s, 3H); 3.13-3.18 (m, 1H); 3.26-3.31 (m, 1H); 4.95-5.00 (m, 1H);

6.79 (s, 1H); 6.93-7.01 (m, 3H); 7.26 (d, 8.4 Hz, 2H); 7.53-7.63 (m, 2H); 7.95-8.00 (m, 2H); 8.58 (br s, 1H); 8.77 (s, 1H).

Example 135

2-{(S)-1-Carboxy-2-[4-(3-methyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3-methyl-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 2.26 (s, 3H); 3.11-3.16 (m, 1H); 3.25-3.30 (m, 1H); 4.94-4.99 (m, 1H); 6.97-7.02 (m, 3H); 7.24 (d, 8.4 Hz, 2H); 7.52 (d, 8.8 Hz, 1H); 7.58-7.68 (m, 2H); 7.90-7.96 (m, 2H); 8.70 (br s, 1H); 8.74 (s, 1H).

Example 136

2-(3-Carboxy-6-chloro-quinolin-2-ylamino)-3-(3,5-difluoro-phenyl)-succinic acid

In close analogy to the procedure described in Example 1, 2,6-dichloroquinoline-3-carboxylic acid is reacted with 2-amino-3-(3,5-difluoro-phenyl)-succinic acid [prepared by analogy to *J. Med. Chem.* 1973, 16, 1277-1280.; using alkylation of diethyl acetamidomalonate by methyl bromo-(3,5-difluoro-phenyl)-acetate] in DMSO to provide the title compound in good yield.
Mp 230-250° C. (decomp.). LCMS m/z 451 (M+1).

Example 137

6-Chloro-2-[1-(2-dimethylamino-ethoxycarbonyl)-2-pyridin-2-yl-ethylamino]-quinoline-3-carboxylic acid In close analogy to the procedure described in Example 43, 2,6-dichloro-quinoline-3-carboxylic acid is reacted with 2-amino-3-pyridin-2-yl-propionic acid 2-dimethylamino-ethyl ester to provide after chromatographical separation the title compound in moderate yield.
LCMS m/z 443 (M+1).

Example 138

6-Chloro-2-(1-ethoxycarbonyl-2-pyridin-2-yl-ethylamino)-quinoline-3-carboxylic acid In close analogy to the procedure described in Example 43, 2,6-dichloro-quinoline-3-carboxylic acid is reacted with 2-amino-3-pyridin-2-yl-propionic acid ethyl ester to provide after chromatographical separation the title compound in moderate yield.
LCMS m/z 400 (M+1).

Example 139

2-{(S)-2-[4-(3-Bromo-pyridin-2-yloxy)-phenyl]-1-carboxy-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3-bromo-pyridin-2-yloxy)-phenyl]-propionic acid (prepared by analogy to Example 109a,b) in DMSO to provide the title compound in good yield.
$^1$H-NMR (200 MHz, DMSO-$d_6$), δ (ppm) 3.10-3.19 (m, 1H); 3.25-3.30 (m, 1H); 4.92-4.97 (m, 1H); 7.02-7.12 (m, 3H); 7.29 (d, 8.2 Hz, 2H); 7.49-7.62 (m, 2H); 7.96 (s, 1H); 8.07-8.18 (m, 2H); 8.71 (s, 1H); 8.90-9.10 (br s, 1H).

Example 140

2-{(S)-1-Carboxy-2-[4-(3,5-dichloro-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3,5-dichloro-pyridin-2-yloxy)-phenyl]-propionic acid (prepared by analogy to Example 109a,b) in DMSO to provide the title compound in good yield.
$^1$H-NMR (200 MHz, DMSO-$d_6$), δ (ppm) 3.10-3.30 (m, 2H); 4.92-4.99 (m, 1H); 7.08 (d, 9.0 Hz, 2H); 7.30 (d, 8.2 Hz, 2H); 7.49-7.62 (m, 2H); 7.97 (d, 2.4 Hz, 1H); 8.14 (d, 2.4 Hz, 1H); 8.32 (d, 2.2 Hz, 1H); 8.72 (s, 1H); 8.90-9.10 (br s, 1H).

Example 141

2-{(S)-2-[4-(5-Amino-pyridin-2-yloxy)-phenyl]-1-carboxy-ethylamino}-6-chloro-quinoline-3-carboxylic acid In close analogy to the procedure described in Example 109c, 2,6-dichloroquinoline-3-carboxylic acid is reacted with (S)-2-amino-3-[4-(5-amino-pyridin-2-yloxy)-phenyl]-propionic acid (prepared by analogy to Example 109a,b) in DMSO to provide the title compound in good yield.
$^1$H-NMR (400 MHz, DMSO-$d_6$), δ (ppm) 3.08-3.13 (m, 1H); 3.21-3.25 (m, 1H); 4.93-4.97 (m, 1H); 6.70 (d, 8.8 Hz, 1H); 6.84 (d, 8.4 Hz, 2H); 7.04-7.06 (m, 1H); 7.18 (d, 8.8 Hz, 2H); 7.52-7.63 (m, 3H); 7.99 (s, 1H); 8.51 (d, 6.8 Hz, 1H); 8.76 (s, 1H).

Example 142

2-{(S)-1-Carboxy-2-[4-(7-chloro-quinolin-4-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(7-chloro-quinolin-4-yloxy)-phenyl]-propionic acid (prepared by analogy to Example 109a,b) in DMSO to provide the title compound in good, yield.
$^1$H-NMR (200 MHz, DMSO-$d_6$), δ (ppm) 3.15-3.30 (m, 2H); 5.03-5.12 (m, 1H); 6.39 (d, 5.0 Hz, 1H); 7.19 (d, 9.0 Hz, 2H); 7.39 (d, 8.6 Hz, 2H); 7.49-7.69 (m, 3H); 7.99 (d, 2.0 Hz, 1H); 8.07 (d, 2.0 Hz, 1H); 8.31 (d, 9.0 Hz, 1H); 8.64 (d, 5.0 Hz, 1H); 8.65-8.75 (br s, 1H); 8.76 (s, 1H).

Example 143

2-{(S)-1-Carboxy-2-[4-(5-chloro-3-fluoro-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with(S)-2-amino-3-[4-(5-chloro-3-fluoro-pyridin-2-yloxy)- phenyl]-propionic acid (prepared by analogy to Example 109a,b) in DMSO to provide the title compound in good yield.

¹H-NMR (200 MHz, DMSO-d₆), δ (ppm) 3.10-3.30 (m, 2H); 4.93-5.01 (m, 1H); 7.10 (d, 8.0 Hz, 2H); 7.29 (d, 8.6 Hz, 2H); 7.51-7.63 (m, 2H); 8.01 (d, 8.8 Hz, 2H); 8.19-8.22 (m, 1H); 8.70-8.80 (br s, 1H); 8.76 (s, 1H).

Example 144

2-{(S)-2-[4-(3-Bromo-pyridin-4-yloxy)-phenyl]-1-carboxy-ethylamino}-6-chloro-quinoline-3-carboxylic acid In close analogy to the procedure described in Example 109c, 2,6-dichloroquinoline-3-carboxylic acid is reacted with (S)-2-amino-3-[4-(3-bromo-pyridin-4-yloxy)-phenyl]-propionic acid (prepared by analogy to Example 109a,b) in DMSO to provide the title compound in good yield.

¹H-NMR (400 MHz, DMSO-d₆), δ (ppm) 3.15-3.20 (m, 2H); 5.04-5.08 (m, 1H); 6.49 (d, 5.2 Hz, 1H); 7.08 (d, 8.4 Hz, 2H); 7.34 (d, 8.4 Hz, 2H); 7.50-7.63 (m, 2H); 8.00 (s, 1H); 8.29 (d, 6.0 Hz, 1H); 8.53 (d, 6.8 Hz, 1H); 8.70 (s, 1H); 8.76 (s, 1H).

Example 145

2-{(S)-2-[4-(7-Bromo-isoquinolin-1-yloxy)-phenyl]-1-carboxy-ethylamino}-6-chloro-quinoline-3-carboxylic acid In close analogy to the procedure described in Example 109c, 2,6-dichloroquinoline-3-carboxylic acid is reacted with (S)-2-amino-3-[4-(7-bromo-isoquinolin-1-yloxy)-phenyl]-propionic acid (prepared by analogy to Example 109a,b) in DMSO to provide the title compound in good yield.

¹H-NMR (200 MHz, DMSO-d₆), δ (ppm) 3.10-3.30 (m, 2H); 4.75-4.85 (br s, 1H); 7.16 (d, 8.8 Hz, 2H); 7.34-7.41 (m, 4H); 7.52 (d, 6.0 Hz, 1H); 7.76 (s, 1H); 7.95-8.00 (m, 3H); 8.41 (s, 1H); 8.48 (s, 1H); 10.70-10.90 (br s, 1H).

Example 146

2-{(S)-1-Carboxy-2-[4-(2-chloro-pyridin-4-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(2-chloro-pyridin-4-yloxy)-phenyl]-propionic acid (prepared by analogy to Example 109a,b) in DMSO to provide the title compound in good yield.

¹H-NMR (400 MHz, DMSO-d₆), δ (ppm) 3.16-3.21 (m, 2H); 5.02-5.08 (m, 1H); 6.77 (d, 6.0 Hz, 1H); 6.91 (s, 1H); 7.11 (d, 8.0 Hz, 2H); 7.35 (d, 8.4 Hz, 2H); 7.52 (d, 8.8 Hz, 1H); 7.61 (d, 8.8 Hz, 1H); 7.99 (s, 1H); 8.23 (d, 6.0 Hz, 1H); 8.60 (br s, 1H); 8.75 (s, 1H).

Example 147

2-{(S)-2-[4-(6-Bromo-[1,8]naphthyridin-2-yloxy)-phenyl]-1-carboxy-ethylamino}-6-chloro-quinoline-3-carboxylic acid In close analogy to the procedure described in Example 109c, 2,6-dichloroquinoline-3-carboxylic acid is reacted with (S)-2-amino-3-[4-(6-bromo-[1,8]naphthyridin-2-yloxy)-phenyl]-propionic acid (prepared by analogy to Example 109a,b) in DMSO to provide the title compound in good yield.

¹H-NMR (200 MHz, DMSO-d₆), δ (ppm) 3.05-3.30 (m, 2H); 4.80-4.90 (m, 1H); 7.17 (d, 8.2 Hz, 2H); 7.36-7.44 (m, 5H); 7.76 (s, 1H); 8.41-8.45 (m, 2H); 8.74 (d, 2.0 Hz, 1H); 8.91 (d, 2.0 Hz, 1H); 10.70-10.90 (br s, 1H).

Example 148

2-{(S)-1-Carboxy-2-[4-(6-methyl-pyridin-2-yloxy)-phenyl]-ethylamino}-6-chloro-quinoline-3-carboxylic acid In close analogy to the procedure described in Example 109c, 2,6-dichloroquinoline-3-carboxylic acid is reacted with (S)-2-amino-3-[4-(6-methyl-pyridin-2-yloxy)-phenyl]-propionic acid (prepared by analogy to Example 109a,b) in DMSO to provide the title compound in good yield.

¹H-NMR (400 MHz, DMSO-d₆), δ (ppm) 2.31 (s, 3H); 3.13-3.18 (m, 1H); 3.27-3.32 (m, 1H); 4.98-5.02 (m, 1H); 6.65 (d, 8.0 Hz, 1H); 6.97-7.02 (m, 3H); 7.27 (d, 8.0 Hz, 2H); 7.53-7.70 (m, 3H); 7.99 (s, 1H); 8.68 (br s, 1H); 8.76 (s, 1H).

Example 149

2-(1-Carboxy-2-pyridin-2-yl-ethylamino)-6-chloro-quinoline-3-carboxylic acid

In close analogy to the procedure described in Example 1, 2,6-dichloroquinoline-3-carboxylic acid is reacted with 2-amino-3-pyridin-2-yl-propionic acid in DMSO to provide the title compound in good yield.

¹H-NMR (400 MHz, DMSO-d₆), δ (ppm) 3.33-3.38 (m, 2H); 5.14 (br s, 1H); 7.22-7.31 (m, 2H); 7.51-7.70 (m, 3H); 7.97 (s, 1H); 8.49 (s, 1H); 8.73 (s, 2H).

Example 150

6-Chloro-2-((S)-2-phenyl-1-propylcarbamoyl-ethylamino)-quinoline-3-carboxylic acid In close analogy to the procedure described in Example 1, 2,6-dichloroquinoline-3-carboxylic acid is reacted with (S)-2-amino-3-phenyl-N-propyl-propionamide [*Chem. Lett.* 2003, 32 (4), 372-373.] in DMSO to provide the title compound in good yield.

¹H-NMR (400 MHz, DMSO-d₆), δ (ppm) 0.72 (t, 6.8 Hz, 3H); 1.29-1.34 (m, 2H); 2.90-3.10 (m, 4H); 4.84 (br s, 1H); 7.16-7.26 (m, 5H); 7.45-7.60 (m, 2H); 7.85-8.00 (m, 2H); 8.59 (s, 1H); 9.40-9.60 (br s, 1H).

Example 151

6-Chloro-2-((S)-2-phenyl-1-phenylcarbamoyl-ethylamino)-quinoline-3-carboxylic acid In close analogy to the procedure described in Example 1, 2,6-dichloroquinoline-3-carboxylic acid is reacted with (S)-2-amino-3,N-diphenyl-propionamide in DMSO to provide the title compound in moderate yield.

¹H-NMR (400 MHz, DMSO-d₆), δ (ppm) 3.10-3.25 (m, 2H); 5.08-5.10 (m, 1H); 7.03 (t, 7.2 Hz, 1H); 7.19 (d, 6.8 Hz, 1H); 7.25-7.29 (m, 6H); 7.50 (d, 9 Hz, 1H); 7.55-7.60 (m, 3H); 7.96 (s, 1H); 8.71 (s, 1H); 10.21 (s, 1H).

Example 152

2-((S)-1-Carboxy-2-hydroxy-ethylamino)-6-chloro-quinoline-3-carboxylic acid

In close analogy to the procedure described in Example 1, 2,6-dichloroquinoline-3-carboxylic acid is reacted with L-serine in DMSO to provide the title compound in good yield.

$^1$H-NMR (200 MHz, DMSO-$d_6$), δ (ppm) 3.80-3.90 (m, 2H); 4.77-4.81 (m, 1H); 7.47 (d, 9 Hz, 1H); 7.58 (d, 9 Hz, 1H); 7.96 (s, 1H); 8.73 (s, 1H); 9.04 (br s, 1H).

Example 153

6-Chloro-2-[(S)-1-(2-hydroxy-ethylcarbamoyl)-2-phenyl-ethylamino]-quinoline-3-carboxylic acid In close analogy to the procedure described in Example 1, 2,6-dichloroquinoline-3-carboxylic acid is reacted with (S)-2-amino-N-(2-hydroxy-ethyl)-3-phenyl-propionamide [*JACS* 1969, 91, 2684-2691.] in DMSO to provide the title compound in good yield.

$^1$H-NMR (400 MHz, DMSO-$d_6$), δ (ppm) 3.01 (dd, 13.2 and 7.6 Hz, 1H); 3.05-3.15 (m, 5H); 4.60 (t 4.6 Hz, 1H); 4.87-4.90 (m, 1H); 7.15-7.18 (m, 1H); 7.23-7.26 (m, 4H); 7.49 (d, 9 Hz, 1H); 7.55 (dd, 9 and 2 Hz, 1H); 7.91 (d, 2 Hz, 1H); 8.64 (s, 1H).

Example 154

6-Chloro-2-[(S)-2-phenyl-1-(1H-tetrazol-5-ylcarbamoyl)-ethylamino]-quinoline-3-carboxylic acid In close analogy to the procedure described in Example 1, 2,6-dichloroquinoline-3-carboxylic acid is reacted with (S)-2-amino-3-phenyl-N-(1H-tetrazol-5-yl)-propionamide (prepared by reaction of N-Boc-L-phenylalanine with isobutyl chloroformate followed by 5-amino-1H-tetrazole) in DMSO to provide the title compound in moderate yield.

$^1$H-NMR (400 MHz, DMSO-$d_6$), δ (ppm) 3.10-3.20 (m, 2H); 5.08-5.12 (m, 1H); 7.20 (t, 7 Hz, 1H); (7.22-7.34 (m, 4H); 7.39 (d, 8.8 Hz, 1H); 7.57 (dd, 8.8 and 2 Hz, 1H); 7.96 (d, 2 Hz, 1H); 8.71 (s, 1H); 8.80 (br s, 1H), 12.35 (br s, 1H).

Example 155

2-[(S)-1-Carboxy-2-(1H-indol-3-yl)-ethylamino]-6,8-dichloro-quinoline-3-carboxylic acid In close analogy to the procedure described in Example 1, 2,6,8-trichloroquinoline-3-carboxylic acid is reacted with L-tryptophan in DMSO to provide the title compound in good yield.

$^1$H-NMR (400 MHz, DMSO-$d_6$), δ (ppm) 3.30-3.36 (m, 1H); 3.46-3.51 (m, 1H); 5.05-5.10 (m, 1H); 6.90-6.94 (m, 1H); 7.02-7.06 (m, 1H); 7.16 (s, 1H); 7.31 (d, 7.6 Hz, 1H); 7.49 (d, 7.6 Hz, 1H); 7.88 (s, 1H); 7.99 (s, 1H); 8.77 (s, 1H); 8.86 (d, 5.6 Hz, 1H); 10.89 (s, 1H). LCMS m/z 444 (M+1).

Example 156

2-((S)-1-Carboxy-2-thiophen-2-yl-ethylamino)-6-chloro-quinoline-3-carboxylic acid In close analogy to the procedure described in Example 1, 2,6-dichloroquinoline-3-carboxylic acid is reacted with (S)-2-amino-3-thiophen-2-yl-propionic acid to provide the title compound in good yield.

Mp >250° C. (decomp.). $^1$H-NMR (200 MHz, DMSO-$d_6$), δ (ppm) 3.40-3.71 (m, 2H); 4.99-5.05 (m, 1H); 6.85-6.94 (m, 2H); 7.15 (d, 5.2 Hz, 1H); 7.50-7.64 (m, 2H); 7.76 (d, 2.0 Hz, 1H); 8.67 (s, 1H). LCMS m/z 377 (M+1).

TABLE 1

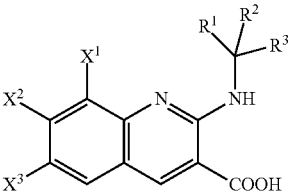

| Example No. | $X^1$ | $X^2$ | $X^3$ | $R^1$ | $R^2$ | $R^3$ |
|---|---|---|---|---|---|---|
| 2 | H | H | Cl | COOH | 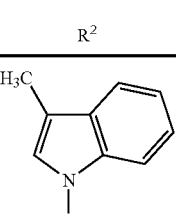 | H |
| 3 | H | H | Cl | COOH | $CH_2CH_2CH_3$ | H |
| 4 | H | H | Cl | COOH | H | H |
| 5 | H | H | Cl | COOH | Ph | H |
| 18 | H | H | Cl | COOH | 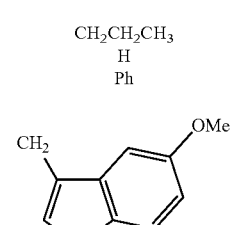 | H |

TABLE 1-continued
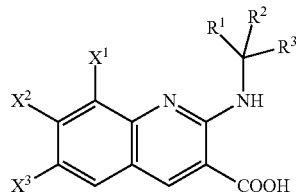
| Example No. | X¹ | X² | X³ | R¹ | R² | R³ |
|---|---|---|---|---|---|---|
| 21 | H | H | Cl | COOH | CH₂-(5-methyl-1H-indol-3-yl) | H |
| 24 | H | H | Cl | COOH | 2,3-dihydro-1H-inden-1-yl* | |
| 25 | H | H | Cl | COOH | CH₂-(5-fluoro-1H-indol-3-yl) | H |
| 26 | H | H | Cl | COOH | CH₃ | H |
| 28 | H | H | Cl | COOH | (CH₂)₂Ph | H |
| 29 | H | H | Cl | COOH | CH₂-(1H-imidazol-4-yl) | H |
| 33 | H | H | Cl | COOH | CH₂-(6-fluoro-1H-indol-3-yl) | H |
| 38 | H | H | Cl | COOH | 6-chloro-2-(methylamino)quinoline-3-carboxylic acid moiety | H |
| 39 | H | H | Cl | COOH | CH₂-(4-fluorophenyl) | H |

TABLE 1-continued
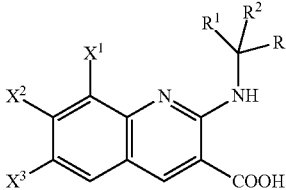
| Example No. | X¹ | X² | X³ | R¹ | R² | R³ |
|---|---|---|---|---|---|---|
| 40 | H | H | Cl | COOH | 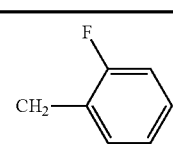 | H |
| 43 | H | H | Cl | C(O)NH-2-naphthyl | CH$_3$ | H |
| 46 | H | H | Cl | 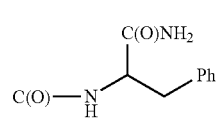 | CH$_2$Ph | H |
| 52 | H | H | Cl | COOH | 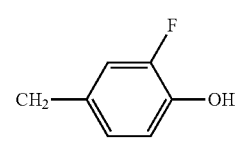 | H |
| 53 | H | H | Cl | COOH | 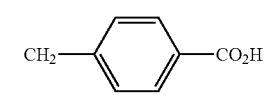 | H |
| 54 | H | H | Cl | 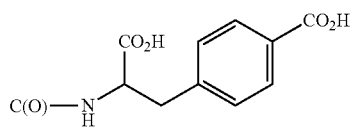 | 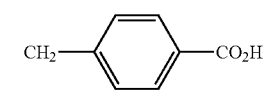 | H |
| 56 | Br | H | Br | COOH | CH$_2$Ph | H |
| 57 | H | H | Cl | COOH | 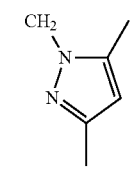 | H |
| 58 | H | H | Cl | COOH | 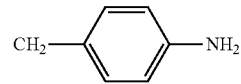 | H |
| 59 | H | H | Cl | COOH | 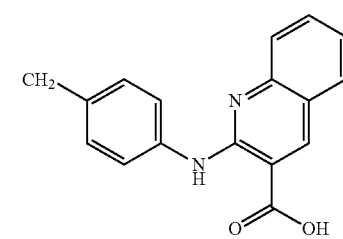 | H |
| 60 | H | H | Cl | 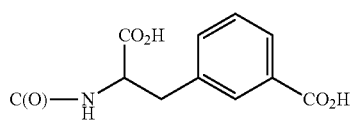 | 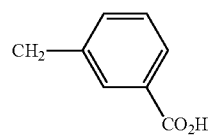 | H |

TABLE 1-continued

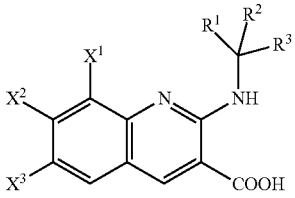

| Example No. | X¹ | X² | X³ | R¹ | R² | R³ |
|---|---|---|---|---|---|---|
| 61 | H | H | Cl | COOH | 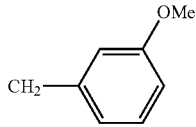 3-methoxybenzyl (CH₂-C₆H₄-OMe) | H |
| 62 | H | H | Cl | COOH | 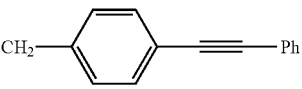 4-(phenylethynyl)benzyl | H |
| 63 | H | H | Cl | COOH | 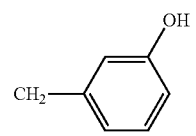 3-hydroxybenzyl | H |
| 64 | Cl | H | Cl | COOH | 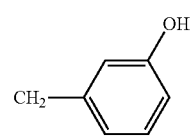 3-hydroxybenzyl | H |
| 65 | H | H | Cl | COOH | 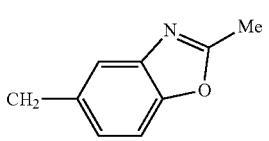 (2-methylbenzoxazol-5-yl)methyl | H |
| 66 | H | H | Cl | COOH | CH₂C(O)NHPh | H |
| 67 | Cl | H | Cl | COOH | 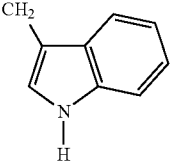 (1H-indol-3-yl)methyl | H |
| 68 | H | H | Cl | COOH | 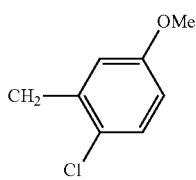 (2-chloro-5-methoxyphenyl)methyl | H |
| 69 | H | H | Cl | 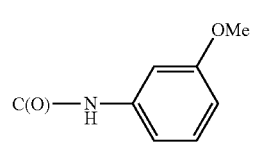 C(O)NH-(3-methoxyphenyl) | CH₂OH | H |
| 70 | H | H | Cl | C(O)NHPh | H | H |
| 71 | Cl | H | Cl | C(O)NHPh | H | H |

TABLE 1-continued

| Example No. | X¹ | X² | X³ | R¹ | R² | R³ |
|---|---|---|---|---|---|---|
| 72 | H | H | Cl | COOH | CH₂-(2-MeO-phenyl) | H |
| 73 | H | H | Cl | COOH | CH₂C(O)NH₂ | H |
| 74 | H | H | Cl | COOH | CH₂C(O)NHCH(CH₃)Ph | H |
| 75 | H | H | Cl | C(O)NHPh | CH₂CO₂H | H |
| 76 | H | H | Cl | C(O)NHPh | CH₂OH | H |
| 77 | H | H | Cl | COOH | (CH₂)₂C(O)NH₂ | H |
| 78 | H | H | Cl | COOH | CH₂-[1-(3-methyl-4-nitrobenzyl)imidazol-4-yl] | H |
| 79 | H | H | Cl | COOH | CH(CO₂H)Ph | H |
| 80 | H | H | Cl | COOH | CH₂-(4-methylphenyl) linked to 2-(NH)-6-chloroquinoline-3-CO₂H via CH(CO₂H) | H |
| 81 | H | H | Cl | COOH | CH₂-(3-phenyl) linked via O to 6-chloroquinoline-3-CO₂H | H |
| 82 | H | H | Cl | COOH | CH₂-(3-methylphenyl) linked to 2-(NH)-6-chloroquinoline-3-CO₂H via CH(CO₂H) | H |
| 83 | H | H | Cl | COOH | CH₂-2-thienyl | H |
| 84 | H | H | Cl | C(O)NH₂ | CH₂Ph | H |
| 85 | H | H | Cl | C(O)NHMe | CH₂Ph | H |
| 86 | Cl | H | Cl | C(O)NHMe | CH₂Ph | H |
| 87 | H | H | Cl | COOH | CH₂NHC(O)Ph | H |
| 88 | Cl | H | Cl | C(O)NHPh | CH₂OH | H |
| 89 | H | H | Cl | COOH | CH₂NHC(O)CH₂Ph | H |

TABLE 1-continued

| Example No. | X¹ | X² | X³ | R¹ | R² | R³ |
|---|---|---|---|---|---|---|
| 90 | H | H | Cl | 2-MeO-C₆H₄-CH(NHC(O)—)-CO₂H | CH₂-(2-MeO-C₆H₄) | H |
| 91 | H | H | Cl | 2-Cl-5-MeO-C₆H₃-CH(NHC(O)—)-CO₂H | CH₂-(2-Cl-5-MeO-C₆H₃) | H |
| 92 | H | H | Cl | 2-thienyl-CH(NHC(O)—)-CO₂H | CH₂-2-thienyl | H |
| 93 | H | H | Cl | COOH | CH₂-(3-COOH-C₆H₄) | H |
| 94 | H | H | Cl | 4-(PhC≡C)-C₆H₄-CH(NHC(O)—)-CO₂H | CH₂-(4-(PhC≡C)-C₆H₄) | H |
| 95 | Me | H | Cl | COOH | CH₂Ph | H |
| 96 | H | H | Cl | COOH | CH₂-(4-(quinolin-2-yloxy)-C₆H₄) | H |
| 97 | Me | H | Cl | COOH | CH₂-(1H-indol-3-yl) | H |

TABLE 1-continued
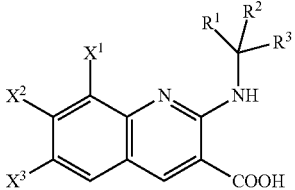
| Example No. | X¹ | X² | X³ | R¹ | R² | R³ |
|---|---|---|---|---|---|---|
| 98 | H | H | Cl | COOH | 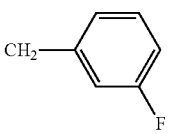 | H |
| 99 | H | H | Cl | COOH | 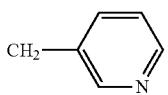 | H |
| 100 | H | H | Cl | COOH | 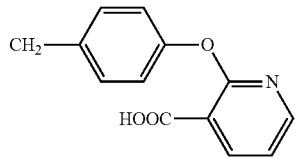 | H |
| 102 | H | H | Br | COOH |  | H |
| 103 | H | H | Br | COOH | 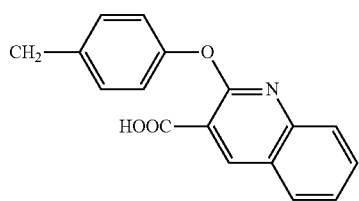 | H |
| 104 | H | H | Cl | COOH | 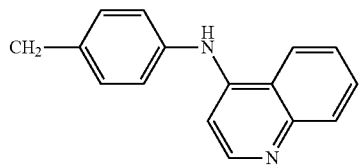 | H |
| 105 | H | H | Cl | COOH | 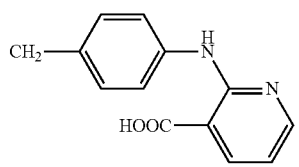 | H |
| 106 | H | H | Cl | COOH | 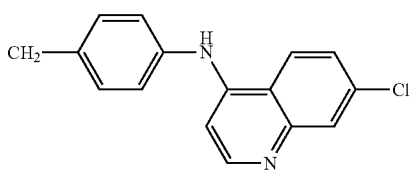 | H |

TABLE 1-continued

| Example No. | X¹ | X² | X³ | R¹ | R² | R³ |
|---|---|---|---|---|---|---|
| 107 | H | H | Br | COOH | CH₂-(4-phenoxy)-6-bromoquinoline-3-carboxylic acid | H |
| 108 | H | H | Cl | COOH | CH₂-(4-phenyl)-NH-quinolin-2-yl | H |
| 110 | H | H | Cl | COOH | CH₂-(4-phenoxy)-quinoline-3-carboxylic acid | H |
| 111 | H | H | Br | COOH | CH₂-(4-phenoxy)-5-bromopyridin-2-yl | H |
| 112 | H | H | Br | COOH | CH₂-(4-phenoxy)-quinolin-2-yl | H |
| 113 | H | H | Cl | COOH | CH₂-(4-bromophenyl) | H |
| 115 | Cl | H | Cl | COOH | CH₂-(3-fluorophenyl) | H |
| 116 | Cl | H | Cl | COOH | CH(CO₂H)Ph | H |
| 117 | H | H | Cl | C(O)NHPh | CH₂OCH₂Ph | H |

TABLE 1-continued

[Structure: quinoline with X¹ at 8-position, X² at 7, X³ at 6, COOH at 3, and NH-CR¹R²R³ at 2]

| Example No. | X¹ | X² | X³ | R¹ | R² | R³ |
|---|---|---|---|---|---|---|
| 119 | H | H | Cl | COOH | CH(CO₂H)-(3-fluorophenyl) | H |
| 121 | H | H | Cl | COOH | CH₂C(O)NHCH₂Ph | H |
| 136 | H | H | Cl | COOH | CH(CO₂H)-(3,5-difluorophenyl) | H |
| 137 | H | H | Cl | C(O)O(CH₂)₂NMe₂ | CH₂-2-pyridyl | H |
| 149 | H | H | Cl | COOH | CH₂-2-pyridyl | H |

TABLE 2

[Structure: same quinoline scaffold with stereochemistry indicated at the CR¹R²R³ carbon]

| Example No. | X¹ | X² | X³ | R¹ | R² | R³ |
|---|---|---|---|---|---|---|
| 1 | H | H | Cl | COOH | CH₂Ph | H |
| 8 | H | H | Cl | COOH | CH₂-(4-{[6-chloro-3-carboxyquinolin-2-yl]oxy}phenyl) | H |
| 9 | H | H | Cl | COOH | CH₂-(4-nitrophenyl) | H |
| 11 | H | H | Cl | CH₂OH | Ph | H |
| 13 | H | H | Cl | CH₂OH | CH₂Ph | H |

TABLE 2-continued

[Structure: quinoline with X¹ at 8-position, X² at 7-position, X³ at 6-position, 3-COOH, 2-NH-C(R¹)(R²)(R³)]

| Example No. | X¹ | X² | X³ | R¹ | R² | R³ |
|---|---|---|---|---|---|---|
| 14 | H | H | Cl | CH₂OH | CH₂-(1H-indol-3-yl) | H |
| 15 | H | H | Cl | COOH | CH₂-(1H-indol-3-yl) | H |
| 16 | H | H | Cl | COOH | (CH₂)₄NHC(O)OCH₂Ph | H |
| 17 | H | H | Cl | COOH | CH₂-(4-methoxyphenyl) | H |
| 22 | H | H | Cl | COOH | CH₂-(4-OCH₂Ph-phenyl) | H |
| 23 | H | H | Cl | COOH | CH₂-(4-chlorophenyl) | H |
| 27 | H | H | Cl | COOH | (CH₂)₄NH₂ | H |
| 32 | H | Cl | Cl | COOH | CH₂Ph | H |
| 34 | H | H | Cl | COOH | CH₂-(4-hydroxyphenyl) | H |
| 35 | H | H | Cl | COOH | CH₂-cyclohexyl | H |
| 37 | H | H | Cl | COOH | CH₂-(3,4-dihydroxyphenyl) | H |
| 41 | H | H | Cl | COOH | CH₂-(3-nitro-4-hydroxyphenyl) | H |
| 42 | Cl | H | Cl | COOH | CH₂Ph | H |

TABLE 2-continued

General structure: 2-(substituted amino)quinoline-3-carboxylic acid with X¹, X², X³ substituents on the quinoline ring (at positions 8, 7, 6) and R¹, R², R³ on the carbon attached to NH.

| Example No. | X¹ | X² | X³ | R¹ | R² | R³ |
|---|---|---|---|---|---|---|
| 48 | H | H | Cl | COOH | CH₂-(4-methyl-2-aminophenyl)-O-(6-chloro-3-carboxyquinolin-2-yl) | H |
| 49 | H | H | Cl | COOH | CH₂-(3-amino-4-hydroxyphenyl) | H |
| 50 | H | H | Cl | COOH | (CH₂)₃-NH-(6-chloro-3-carboxyquinolin-2-yl) | H |
| 51 | H | H | Cl | COOH | CH₂-(3-chloro-4-hydroxyphenyl) | H |
| 55 | H | H | Cl | COOH | CH₂-4-pyridyl | H |
| 101 | H | H | Cl | COOH | CH₂-(4-((5-bromopyridin-2-yl)oxy)phenyl) | H |
| 109 | H | H | Cl | COOH | CH₂-(4-(quinolin-4-yloxy)phenyl) | H |
| 114 | H | H | Cl | COOH | CH₂COOH | H |
| 118 | Cl | H | Cl | COOH | CH₂-(4-hydroxyphenyl) | H |
| 120 | Me | H | Me | COOH | CH₂Ph | H |

TABLE 2-continued

[Structure: quinoline with X¹ at 8-position, X² at 7-position, X³ at 6-position, 2-NH-C(R¹)(R²)(R³), and 3-COOH]

| Example No. | X¹ | X² | X³ | R¹ | R² | R³ |
|---|---|---|---|---|---|---|
| 122 | Cl | H | Cl | COOH | CH₂-(4-phenoxy)-(6,8-dichloro-3-carboxyquinolin-2-yl) | H |
| 123 | Cl | H | Cl | COOH | CH₂-(1-methylindol-3-yl) | H |
| 124 | H | H | Cl | COOH | CH₂-(4-phenoxy)-(6-chloroquinolin-2-yl) | H |
| 125 | H | H | Cl | COOH | CH₂-(4-phenoxy)-(8-chloroquinolin-2-yl) | H |
| 126 | H | H | Cl | COOH | CH₂-(4-phenoxy)-(3-chloropyridin-2-yl) | H |
| 127 | H | H | Cl | COOH | CH₂-(4-phenoxy)-(5-trifluoromethylpyridin-2-yl) | H |

TABLE 2-continued

| Example No. | X¹ | X² | X³ | R¹ | R² | R³ |
|---|---|---|---|---|---|---|
| 128 | H | H | Cl | COOH | CH₂-C₆H₄-O-(5-chloropyridin-2-yl) | H |
| 129 | H | H | Cl | COOH | CH₂-C₆H₄-O-(3-trifluoromethylpyridin-2-yl) | H |
| 130 | H | H | Cl | COOH | CH₂-C₆H₄-O-(5-phenyl-1,6-naphthyridin-2-yl) | H |
| 131 | H | H | Cl | COOH | CH₂-C₆H₄-O-(5-iodopyridin-2-yl) | H |
| 132 | H | H | Cl | C(O)O(CH₂)₂OMe | CH₂Ph | H |
| 133 | H | H | Cl | COOH | CH₂-C₆H₄-O-(5-methylpyridin-2-yl) | H |
| 134 | H | H | Cl | COOH | CH₂-C₆H₄-O-(4-methylpyridin-2-yl) | H |

TABLE 2-continued

| Example No. | X¹ | X² | X³ | R¹ | R² | R³ |
|---|---|---|---|---|---|---|
| 135 | H | H | Cl | COOH | CH₂-(4-(3-methylpyridin-2-yloxy)phenyl) | H |
| 138 | H | H | Cl | C(O)OEt | CH₂-2-pyridyl | H |
| 139 | H | H | Cl | COOH | CH₂-(4-(3-bromopyridin-2-yloxy)phenyl) | H |
| 140 | H | H | Cl | COOH | CH₂-(4-(3,5-dichloropyridin-2-yloxy)phenyl) | H |
| 141 | H | H | Cl | COOH | CH₂-(4-(5-aminopyridin-2-yloxy)phenyl) | H |
| 142 | H | H | Cl | COOH | CH₂-(4-(7-chloroquinolin-4-yloxy)phenyl) | H |
| 143 | H | H | Cl | COOH | CH₂-(4-(5-chloro-3-fluoropyridin-2-yloxy)phenyl) | H |
| 144 | H | H | Cl | COOH | CH₂-(4-(3-bromopyridin-4-yloxy)phenyl) | H |

TABLE 2-continued
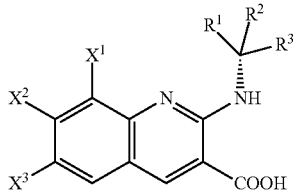
| Example No. | X¹ | X² | X³ | R¹ | R² | R³ |
|---|---|---|---|---|---|---|
| 145 | H | H | Cl | COOH | 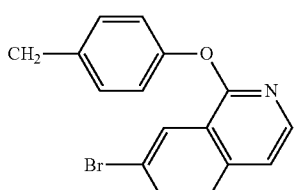 | H |
| 146 | H | H | Cl | COOH | 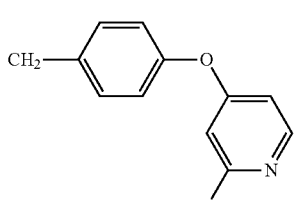 | H |
| 147 | H | H | Cl | COOH | 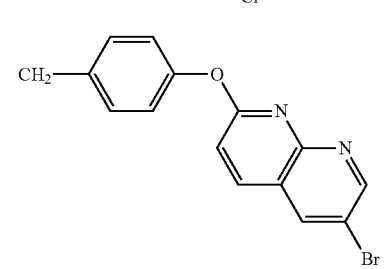 | H |
| 148 | H | H | Cl | COOH | 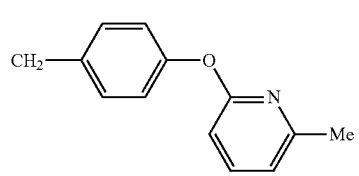 | H |
| 150 | H | H | Cl | C(O)NH(CH$_2$)$_2$Me | CH$_2$Ph | H |
| 151 | H | H | Cl | C(O)NHPh | CH$_2$Ph | H |
| 152 | H | H | Cl | COOH | CH$_2$OH | H |
| 153 | H | H | Cl | C(O)NH(CH$_2$)$_2$OH | CH$_2$Ph | H |
| 154 | H | H | Cl | 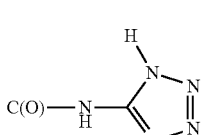 | CH$_2$Ph | H |
| 155 | Cl | H | Cl | COOH | 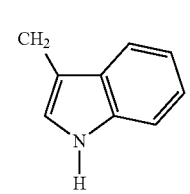 | H |
| 156 | H | H | Cl | COOH | CH$_2$-2-thienyl | H |

TABLE 3

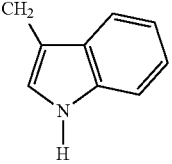

| Example No. | X¹ | X² | X³ | R¹ | R² | R³ |
|---|---|---|---|---|---|---|
| 6 | H | H | Cl | COOH | CH₂Ph | H |
| 7 | H | H | Cl | CH₂OH | Ph | H |
| 10 | H | H | Cl | CH₂OH | CH₂Ph | H |
| 12 | H | H | Cl | COOH | CH₂-(indol-3-yl) | H |
| 19 | H | H | Cl | COOH | CH₂OCH₂Ph | H |
| 20 | H | H | Cl | COOH | CH₂-(1-methylindol-3-yl) | H |
| 30 | H | H | Cl | COOH | CH(Me)Ph | H |
| 31 | H | H | Cl | COOH | CH(Me)Ph (other enantiomer) | H |
| 36 | H | Cl | Cl | COOH | CH₂-(indol-3-yl) | H |
| 44 | H | H | H | COOH | CH₂Ph | H |
| 45 | H | H | H | COOH | CH₂-(indol-3-yl) | H |
| 47 | H | H | Br | COOH | CH₂Ph | H |

Examples of Representative Pharmaceutical Compositions

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration, which contain the active ingredient, may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

FORMULATION EXAMPLES

The following examples are again given by way of illustration only and are not to be construed as limiting.

Example 1

Tablet Formulation

A suitable formulation for a tablet containing 10 milligrams of active ingredient is as follows:

|  | mg |
|---|---|
| Active Ingredient | 10 |
| Lactose | 61 |
| Microcrystalline Cellulose | 25 |
| Talcum | 2 |
| Magnesium stearate | 1 |
| Colloidal silicon dioxide | 1 |

Example 2

Tablet Formulation

Another suitable formulation for a tablet containing 100 mg is as follows:

|  | mg |
|---|---|
| Active Ingredient | 100 |
| Polyvinylpyrrolidone, crosslinked | 10 |
| Potato starch | 20 |
| Polyvinylpyrrolidone | 19 |
| Magnesium stearate | 1 |
| Microcrystalline Cellulose | 50 |
| Film coated and colored. | |
| The film coating material consists of: | |
| Hypromellose | 10 |
| Microcryst. Cellulose | 5 |
| Talcum | 5 |
| Polyethylene glycol | 2 |
| Color pigments | 5 |

Example 3

Capsule Formulation

A suitable formulation for a capsule containing 50 milligrams of active ingredient is as follows:

|  | mg |
| --- | --- |
| Active Ingredient | 50 |
| Corn starch | 26 |
| Dibasic calcium phosphate | 50 |
| Talcum | 2 |
| Colloidal silicon dioxide | 2 | filled in a gelatin capsule.

Example 4

Solution for Injection

A suitable formulation for an injectable solution is as follows:

| Active Ingredient | mg | 10 |
| --- | --- | --- |
| Sodium chloride | mg | q.s. |
| Water for Injection | mL | add 1.0 |

Example 5

Liquid Oral Formulation

A suitable formulation for 1 liter of an oral solution containing 2 milligrams of active ingredient in one milliliter of the mixture is as follows:

|  | mg |
| --- | --- |
| Active Ingredient | 2 |
| Saccharose | 250 |
| Glucose | 300 |
| Sorbitol | 150 |
| Orange flavor | 10 |
| Colorant | q.s. |
| Purified water | add 1000 mL |

Example 6

Liquid oral formulation

Another suitable formulation for 1 liter of a liquid mixture containing 20 milligrams of active ingredient in one milliliter of the mixture is as follows:

|  | G |
| --- | --- |
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water | add 1000 mL |

Example 7

Liquid Oral Formulation

Another suitable formulation for 1 liter of a liquid mixture containing 2 milligrams of active ingredient in one milliliter of the mixture is as follows:

|  | G |
| --- | --- |
| Active Ingredient | 2 |
| Saccharose | 400 |
| Bitter orange peel tincture | 20 |
| Sweet orange peel tincture | 15 |
| Purified water | add 1000 mL |

Example 8

Aerosol Formulation 180 g aerosol solution contain:

|  | G |
| --- | --- |
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

Example 9

TDS Formulation 100 g solution contain:

|  | G |
| --- | --- |
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

Example 10

Nanoparticle Formulation 10 g of polybutylcyanoacrylate nanoparticles contain:

|  | G |
| --- | --- |
| Active Ingredient | 1.00 |
| Poloxamer | 0.10 |
| Butylcyanoacrylate | 8.75 |
| Mannitol | 0.10 |
| Sodium chloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

Pharmacology

The active principles of the present invention, and pharmaceutical compositions thereof and method of treating therewith, are characterized by unique and advantageous properties, rendering the "subject matter as a whole", as claimed herein, unobvious. The compounds and pharmaceutical compositions thereof exhibit, in standard accepted reliable test procedures, the following valuable properties and characteristics:

Methods

Binding Assays for the Characterization of Glycine B Antagonist Properties

[$^3$]MDL-105,519 Displacement Studies

For the evaluation of the binding affinity of the test compounds on the glycine binding pocket of the NMDA receptor, [$^3$H]-MDL-105,519 (GE Healthcare, Freiburg, Germany) displacement studies are performed using a 96-well plate robotic platform. MDL-105,519 (Baron et al., J Pharmacol Exp Ther 1996, 279(1), 62-68; Baron et al., European Journal of Pharmacology, 1997, 323(2-3), 181-192; Hoffner & Wanner, Neuroscience Letters, 1997, 226(2), 79-82) is a selective, high affinity antagonist at the NMDA receptor glycine site.

Preparation of Cortical Membranes:

Tissue preparation is performed according to Foster & Wong (Br J Pharmacol, 1987, 91, 403-409) with some modifications. Anaesthetised male Sprague-Dawley rats (200-250 g, Janvier, Le Genest-Isle, France) are decapitated and their brains removed rapidly. The cortex is dissected out and processed as described by Parsons, et al. (J Pharmacol Exp Ther, 1997, 283(3), 1264-1275). For isolation of the cell membranes, the cortices are homogenized in 20 volumes of ice-cold 0.32 M sucrose (Sigma-Aldrich, Taufkirchen, Germany) using a glass-Teflon homogenizer. The homogenate is centrifuged at 1000×g for 10 minutes, the pellet is discarded and the supernatant centrifuged at 20,000×g for 20 minutes. The resulting pellet is re-suspended in 20 volumes of distilled water and centrifuged for 20 minutes at 8000×g. The supernatant and the buffy coat are then centrifuged three times (48,000×g for 20 minutes) in the presence of 50 mM Tris-HCl, pH 8.0 (assay buffer). All centrifugation steps are carried out at 4° C. After resuspension in 5 volumes of 50 mM Tris-HCl, pH 7.5, the membrane suspension is frozen rapidly at −80° C. On the day of assay, the membranes are thawed and washed four times by resuspension in 50 mM Tris-HCl, pH 7.5, and centrifugation at 48,000×g for 20 minutes. The final pellet is suspended in assay buffer. The amount of protein in the final membrane preparation is determined according to the method of Lowry, et al. (J. Biological Chemistry, 1951, 193, 256-275) with some modifications (Hartree, Analytical Biochemistry, 1972, 48, 422-427). The final protein concentration used for our studies is 400 µg/ml.

Displacement Studies

A robotic system designed for binding assays (Tecan Deutschland GmbH, Crailsheim, Germany) is loaded with the membrane solution, solutions for bound control (buffer/DMSO 20%), unlabeled glycine (1 mM) for evaluation of non-specific binding, all compounds to be tested (at 20-fold concentrations), radioligand and respective 96-well plates.

Before performing displacement studies, saturation experiments are performed to determine the equilibrium dissociation constant ($K_d$) of [$^3$H]-MDL-105,519, which is a parameter for the affinity of the radioligand to the binding site. The protein/receptor concentration is held constant whereas the amount of specific bound radioligand is determined using increasing concentrations of ligand.

On the basis of the saturation experiments, a final [$^3$H]-MDL-105,519 concentration of 2 nM is selected. Firstly, the assay plates are loaded with membrane solution and are shaken at 4° C. The mother plates are then prepared by pipetting the compounds (n=4) into assay buffer/20% DMSO to obtain the desired final concentrations. After transferring radioligand into the assay plates, the compounds are added (including the bound and the non-specific binding control). The final DMSO concentration is 1%. The assay plates are incubated and shaken at 4° C. for 1 h, before the mixture is exhausted as rapidly as possible via a vacuum manifold using the Multiscreen HTS glass fibre (type B) filter plates (Millipore, Schwalbach, Germany) under a constant vacuum of 450 mbar. The membranes are washed four times with cold assay buffer (100 µL). 50 µL of Ultima Gold scintillation cocktail (PerkinElmer, Rodgau-Jügesheim, Germany) is added to the wet filter plates and incubated at room temperature overnight before counting the disintegration per minutes using a liquid scintillation counter (MicroBeta, PerkinElmer, Rodgau-Jügesheim, Germany).

Analysis of Data

For the evaluation of the binding affinity of the test compound to the glycine B binding site and its potency to displace [$^3$H]-MDL-105,519, the measured radioactivity of the radioligand alone is set as 100% bound control and the non-specific binding of the radioligand (which could not displaced by glycine, 1 mM) represented the 0% control. The residual radioactivity after displacement of the test compound is then corrected with respect to the set controls.

Functional Screening for the Characterization of Glycine B Antagonist Properties Antagonistic potencies of the test compounds are functionally evaluated using electrophysiological whole cell patch-clamp recordings and/or fluorometric intracellular $Ca^{2+}$-imaging (FLIPR) screens.

Whole Cell Patch-Clamp Recordings

Preparation and Cultivation of Rat Hippocampal Neurons

Cell preparation is performed as described by Parsons, et al. (Neuropharmacology, 1998, 37(6), 719-727). The female Sprague-Dawley rat is anaesthetised by placing in a saturated $CO_2$-euthanasia chamber under further quiet $CO_2$-influx. Under these conditions the rat loses consciousness after a few seconds and is then sacrificed by cervical dislocation. After opening the abdominal cavity, embryos (E20) are removed and stored in ice cold $Ca^{2+}$- and $Mg^{2+}$-free Hank's Buffered Salt Solution (pH 7.3), containing 4 g/l glucose (HBSS-CMF). Hippocampi are then isolated from the brains of at least 8 embryos after decapitation, transferred into ice cold HBSS-CMF and washed 3 to 4 times.

Hippocampi are pre-incubated for 8 min with a 0.66% trypsin (Sigma-Aldrich) and 0.1% (20 U/ml) DNAase solution (Sigma-Aldrich) in $Ca^{2+}$-free Phosphate Buffered Saline (PBS-CF) and washed 3 times with HBSS-CMF. Cells are then mechanically dissociated by trituration in a PBS-CF solution containing 0.05% (10 U/ml) DNAase and 0.3% of the trypsin inhibitor ovomucoid (all from Sigma-Aldrich). The cells are then centrifuged at 180×g for 10 minutes, and the cell pellet re-suspended in basal Minimum essential medium (MEM, Invitrogen, Karlsruhe, Germany), again carefully triturated to ensure maximal dissociation and finally plated in the flexiPERM inserts (Thermo Fisher Scientific, Langenselbold, Germany) at a density of $15\times10^3$ cells/$cm^2$ (0.5 ml/insert) onto poly-DL-ornithine (Sigma) and mouse laminin (Invitrogen) pre-coated plastic petri dishes. After 1 hour the cells become attached to the bottom of the dish and the inserts may be removed. The cells are then nourished with 2 ml MEM supplemented with 5% foetal calf serum (FCS) and 5% horse serum and incubated at 37° C. with 95% air and 5% $CO_2$ at 95% humidity. After 4 days in vitro (DIV) further glial mitosis is inhibited by adding 10 µl of AraC (5 µM endconcentration). The medium is completely exchanged after an additional 2 DIV and again, but only partly (50%), after 8 DIV. The cells are used for electrophysiological recordings after 11-15 DIV.

Evaluation of Peripheral Antagonistic Potencies

For the peripheral glycine B site antagonistic potency evaluation, compounds are functionally tested using dorsal root ganglia (DRG) neurons, modified from Li et al. (Pain, 2004, 109, 443-452).

Whole Cell Patch Clamp Recordings

Cells are visualised using an inverted microscope and selected for patching based upon their position and morphology. Voltage clamp recordings are made in the whole cell configuration of the patch clamp technique at a holding potential of −70 mV with the aid of an EPC-10 amplifier in combination with pipette manipulator. Patch clamp pipettes are pulled from borosilicate glass using a horizontal puller (P-97 Puller, Sutter Instruments, USA) and, when filled with intracellular solution, have resistances of 1-4 MΩ.

Solutions are delivered via a home-made gravity driven very fast perfusion system (<10 ms) including valves to switch flow on and off in combination with a stepper motor-driven double-barreled theta glass application pipette in order to expose cells to either agonist-free or agonist-containing solutions in presence or absence of antagonist.

The intracellular solution used consists of: 120 mM CsCl, 10 mM EGTA, 1 mM $MgCl_2$, 200 µM $CaCl_2$, 10 mM glucose and 22 mM tetraethyl ammonium chloride (TEA-CL). The corresponding extracellular bath solution contains: 140 mM NaCl, 3 mM KCl, 10 mM glucose, 10 mM HEPES, 1.5 mM $CaCl_2$ and 4.5 mM sucrose (all from Sigma-Aldrich) pH 7.3, and is supplemented with 0.3 µM tetrodotoxin (TTX, Tocris, Bristol, U.K.) to block voltage-activated sodium channels and 0.25 µM bicuculline (Sigma-Aldrich) to block $GABA_A$ receptors.

For the determination of concentration-dependency of blockade, 5 control traces are recorded with application of NMDA (200 µM) and D-Serine (1 µM) for 5 seconds in order to reduce the effect of rundown, then the highest concentration of the test-substance is applied for 1 minute before applying the agonists for 5 seconds in the presence of antagonist. Three recordings are made in the presence of the antagonist and 3 recovery traces are recorded after it's removal. The procedure is repeated for three to four further concentrations of antagonist with declining concentrations e.g. 10, 3, 1, 0.3, and 0.1 µM. For the final recovery, agonists are again applied five times after wash-out of the test substance.

Analysis of Data

Data are analysed using TIDA 5.0 (Heka, Lambrecht, Germany). With the help of Microsoft. Excel, data are pooled and finally GraFit software (Erithacus Software Ltd., Surrey, U.K.) is used to fit the data e.g. with the four parameter logistic equation for determining $IC_{50}$ values. For all data points, the value given is the mean±S.E.M. (standard error of the mean) of results from at least 4 individual cells per concentration.

Calcium FLIPR Studies

Preparation and Cultivation of Rat Cortical Neurons

Primary neurons are prepared from cortices of embryonal rats at day 17 of pregnancy as described by Dichter (Brain Res., 1987, 149, 279). Sprague-Dawley rat embryos (E 17) are decapitated and neocortices are dissected, trypsinized and carefully triturated. The cell suspension is plated on poly-D-lysine pre-coated 96-well Plates (Greiner, Frickenhausen, Germany) at a cell density of 55.000 cells/well. The neurons are cultivated in Neurobasal media containing B27-Supplement and 0.5 µM L-Glutamine (Invitrogen) and MEM supplemented with 5% heat inactivated fetal calf serum (Sigma)+5% heat inactivated horse serum (Invitrogen) in the ratio 1:1 at 37° C. in a humidified atmosphere of 5% $CO_2$/95% air. Medium is exchanged completely at day 4 and to 50% on day 7. At the time of experiments neurons are 11-12 days in vitro.

Calcium FLIPR Studies

The increase of intracellular calcium after stimulation with 30 µM NMDA and 1 µM D-Serine is measured using the fluorometric imaging plate reader (FLIPR) and the Calcium-4-Kit (both Molecular Devices, Ismaning, Germany). Prior to addition of agonist or antagonist the medium is aspirated and cells are loaded for 1 h at room temperature with 150 µL of loading buffer, consisting of Ca-4 sensitive dye reconstituted in extracellular bath solution, pH 7.3. Subsequently, plates are transferred to FLIPR to detect increases in intracellular calcium after the addition of agonist, measured as relative fluorescence units (RFU). Antagonists are pre-incubated with the cells for 10 min at room temperature before the addition of the agonist and co-agonist.

Data Analysis

The fluorescence signal increase after addition of agonist reflects the increase of intracellular calcium. Inconsistencies in the amount of cells per well are normalised by using the spatial uniformity correction of the FLIPR software (Screenworks, Molecular Devices). The mean of replicated temporal data (n=5) is calculated and used for graphical representation. For the evaluation of the antagonistic potency, the calcium changes in response to different concentrations of antagonist are determined using an area under the curve (AUC) calculation. All responses (RFU-values) are determined as percentage of control (=maximum response at 30 µM NMDA and 1 µM D-Serine). $IC_{50}$ values are calculated according the four parameter logistic equation using GraFit (Erithacus Software).

Results for respresentative compounds of the invention are shown in Tables 5 and 6.

TABLE 5

MDL Displacement Studies

| Compound | Chemical Name | NMDA-MDL 105519-r-CTX - IC50 [µM] |
|---|---|---|
| Example 1 | 2-((S)-1-Carboxy-2-phenyl-ethylamino)-6-chloro-quinoline-3-carboxylic acid | 0.41 |
| Example 8 | 2-{(S)-1-Carboxy-2-[4-(3-carboxy-6-chloroquinolin-2-yloxy)-phenyl]-ethylamino}-6-chloro-quinoline-3-carboxylic acid | 0.45 |
| Example 22 | 2-[(S)-2-(4-Benzyloxy-phenyl)-1-carboxy-ethylamino]-6-chloro-quinoline-3-carboxylic acid | 2.70 |
| Example 25 | 2-[1-Carboxy-2-(5-fluoro-1H-indol-3-yl)-ethylamino]-6-chloro-quinoline-3-carboxylic acid | 2.12 |
| Example 31 | erythro-2-(1-Carboxy-2-phenyl-propylamino)-6-chloro-quinoline-3-carboxylic acid | 3.37 |
| Example 32 | 2-((S)-1-Carboxy-2-phenyl-ethylamino)-6,7-dichloro-quinoline-3-carboxylic acid | 5.80 |
| Example 35 | 2-((S)-1-Carboxy-2-cyclohexyl-ethylamino)-6-chloro-quinoline-3-carboxylic acid | 3.30 |
| Example 41 | 2-[(S)-1-Carboxy-2-(4-hydroxy-3-nitro-phenyl)-ethylamino]-6-chloro-quinoline-3-carboxylic acid | 1.87 |
| Example 55 | 2-((S)-1-Carboxy-2-pyridin-4-yl-ethylamino)-6-chloro-quinoline-3-carboxylic acid | 4.39 |
| Example 56 | 6,8-Dibromo-2-(1-carboxy-2-phenyl-ethylamino)-quinoline-3-carboxylic acid | 1.73 |
| Example 95 | 2-(1-Carboxy-2-phenyl-ethylamino)-6-chloro-8-methylquinoline-3-carboxylic acid | 2.29 |
| Example 97 | 2-[1-Carboxy-2-(1H-indol-3-yl)-ethylamino]-6-chloro-8-methylquinoline-3-carboxylic acid | 2.49 |
| Example 104 | 2-{1-Carboxy-2-[4-(quinolin-4-ylamino)-phenyl]-ethylamino}-6-chloro-quinoline-3-carboxylic acid | 0.70 |
| Example 142 | 2-{(S)-1-Carboxy-2-[4-(7-chloro-quinolin-4-yloxy)-phenyl]-ethylamino}-6-chloro-quinoline-3-carboxylic acid | 1.44 |
| Example 144 | 2-{(S)-2-[4-(3-Bromo-pyridin-4-yloxy)-phenyl]-1-carboxy-ethylamino}-6-chloro-quinoline-3-carboxylic acid | 0.84 |
| Example 147 | 2-{(S)-2-[4-(6-Bromo-[1,8]naphthyridin-2-yloxy)-phenyl]-1-carboxy-ethylamino}-6-chloro-quinoline-3-carboxylic acid | 0.29 |
| Example 155 | 2-[(S)-1-Carboxy-2-(1H-indol-3-yl)-ethylamino]-6,8-dichloro-quinoline-3-carboxylic acid | 1.03 |
| Example 156 | 2-((S)-1-Carboxy-2-thiophen-2-yl-ethylamino)-6-chloro-quinoline-3-carboxylic acid | 1.91 |

TABLE 6

Patch Clamp Studies

| Compound | Chemical Name | NMDA-PC-r-HIC-NAM - IC50 [µM] |
|---|---|---|
| Example 6 | 2-((R)-1-Carboxy-2-phenyl-ethylamino)-6-chloro-quinoline-3-carboxylic acid | 0.534 |
| Example 15 | 2-[(S)-1-Carboxy-2-(1-methyl-1H-indol-3-yl)-ethylamino]-6-chloro-quinoline-3-carboxylic acid | 1.357 |
| Example 23 | 2-[(S)-1-Carboxy-2-(4-chloro-phenyl)-ethylamino]-6-chloro-quinoline-3-carboxylic acid | 0.898 |
| Example 25 | 2-[1-Carboxy-2-(5-fluoro-1H-indol-3-yl)-ethylamino]-6-chloro-quinoline-3-carboxylic acid | 0.930 |
| Example 34 | 2-[(S)-1-Carboxy-2-(4-hydroxy-phenyl)-ethylamino]-6-chloro-quinoline-3-carboxylic acid | 1.675 |
| Example 36 | 2-[(R)-1-Carboxy-2-(1H-indol-3-yl)-ethylamino]-6,7-dichloro-quinoline-3-carboxylic acid | 1.153 |
| Example 40 | 2-[1-Carboxy-2-(2-fluoro-phenyl)-ethylamino]-6-chloro-quinoline-3-carboxylic acid | 0.754 |
| Example 41 | 2-[(S)-1-Carboxy-2-(4-hydroxy-3-nitro-phenyl)-ethylamino]-6-chloro-quinoline-3-carboxylic acid | 1.032 |
| Example 47 | 6-Bromo-2-((R)-1-carboxy-2-phenyl-ethylamino)-quinoline-3-carboxylic acid | 0.468 |
| Example 48 | 2-{(S)-2-[3-Amino-4-(3-carboxy-6-chloro-quinolin-2-yloxy)-phenyl]-1-carboxy-ethylamino}-6-chloro-quinoline-3-carboxylic acid | 0.68 |
| Example 56 | 6,8-Dibromo-2-(1-carboxy-2-phenyl-ethylamino)-quinoline-3-carboxylic acid | 1.24 |
| Example 59 | 2-{1-Carboxy-2-[4-(3-carboxy-6-chloro-quinolin-2-ylamino)-phenyl]-ethylamino}-6-chloro-quinoline-3-carboxylic acid | 0.64 |
| Example 79 | 2-(3-Carboxy-6-chloro-quinolin-2-ylamino)-3-phenyl-succinic acid | 0.25 |
| Example 101 | 2-{(S)-2-[4-(5-Bromo-pyridin-2-yloxy)-phenyl]-1-carboxy-ethylamino}-6-chloro-quinoline-3-carboxylic acid | 0.42 |
| Example 107 | 2-{1-Carboxy-2-[3-(3-carboxy-6-bromo-quinolin-2-yloxy)-phenyl]-ethylamino}-6-bromo-quinoline-3-carboxylic acid | 0.28 |
| Example 108 | 2-{1-Carboxy-2-[4-(quinolin-2-ylamino)-phenyl]-ethylamino}-6-chloro-quinoline-3-carboxylic acid | 0.56 |
| Example 110 | 2-{1-Carboxy-2-[4-(3-carboxy-quinolin-2-yloxy)-phenyl]-ethylamino}-6-chloro-quinoline-3-carboxylic acid | 0.38 |
| Example 114 | (S)-2-(3-Carboxy-6-chloro-quinolin-2-ylamino)-succinic acid ammonia hydrate | 0.72 |
| Example 115 | 2-[1-Carboxy-2-(3-fluoro-phenyl)-ethylamino]-6,8-dichloro-quinoline-3-carboxylic acid | 0.51 |
| Example 130 | 2-{(S)-1-Carboxy-2-[4-(5-phenyl-[1,6]naphthyridin-2-yloxy)-phenyl]-ethylamino}-6-chloro-quinoline-3-carboxylic acid | 0.19 |
| Example 131 | 2-{1-Carboxy-2-[4-(5-iodo-pyridin-2-yloxy)-phenyl]-ethylamino}-6-chloro-quinoline-3-carboxylic acid | 0.17 |
| Example 149 | 2-(1-Carboxy-2-pyridin-2-yl-ethylamino)-6-chloro-quinoline-3-carboxylic acid | 0.17 |

CONCLUSIONS

In conclusion, from the foregoing, it is apparent that the present invention provides novel, valuable, and unpredictable applications and uses of the compounds of the present invention, which compounds comprise the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

The instant quinoline derivatives represent a novel class of glycine B antagonists. In view of their potency, they will be useful therapeutics in a wide range of disorders, including CNS disorders, which involve excessive glutamate induced excitation.

These compounds accordingly find application in the treatment of the following disorders of a living animal body, especially a human: pain, including acute pain, chronic pain, allodynia, hyperalgesia, visceral pain, phantom pain, postoperative pain, neuropathic pain, peripheral neuropathy including, for example peripheral neuropathy induced by nociception, inflammation, ischemia, viral infection (HZV), traumatic and other mechanical nerve injury, cancer, diabetes mellitus, HIV infection, fibromyalgia, trigeminus neuralgia, inflammatory bowel diseases (IBD), irritative bowel syndrome (IBS), arthritis including rheumatoid arthritis, osteoarthritis (degenerative joint disease), multiple sclerosis (MS) and gout (metabolic arthritis).

These compounds also find application in the treatment of the following disorders of a living animal body, especially a human: acute insults, including cerebral ischemia, cerebral infarct, brain oedema, anoxia, inner ear insult, inner ear insult in tinnitus, head or brain or spinal cord trauma, head or brain or spinal cord injuries, trauma, sound- or drug-induced inner ear insult, ischaemia resulting from cardiac arrest or stroke or bypass operations or transplants, acute pain, hypoxia, perinatal hypoxia, and ischaemia;

chronic insults, such as neurodegenerative disorders, including Morbus Huntington, Alzheimer's disease Creutzfeld-Jakob's syndrome/disease, bovine spongiform encephalopathy (BSE) prion related infections, diseases involving mitochondrial dysfunction, diseases involving β-amyloid and/or tauopathy, Down's syndrome, motor neuron diseases, amyotrophic lateral sclerosis (ALS), olivoponto-cerebellar atrophy, Parkinson's disease, Neuronal Ceroid Lipofuscinosis, AIDS dementia complex, AIDS-related dementia, dementia related to HIV infections, HIV-1 encephalopathy, AIDS encephalopathy, Korsakoff syndrome, vascular dementia, and corticobasal degeneration;

neurological disorders, including tinnitus, hearing loss, sound- or drug-induced tinnitus, haloperidol-induced dyskinesias, dopaminomimetic-induced dyskinesias, chorea, Huntington's chorea, athetosis, dystonia, stereotypy, ballism, tardive dyskinesias, tic disorder, spasmodic torticollis, blepharospasm, focal and generalized dystonia, nystagmus, Parkinson's dementia, mild cognitive impairment, cognitive deficits in various forms of mild cognitive impairment, cognitive deficits in various forms of dementia, dementia pugilistica, vascular and frontal lobe dementia, cognitive impairment, learning impairment, L-dopa-induced dykinesias, L-dopa-induced dykinesias in Parkinson's disease therapy, dyskinesias, dyskinesia in Huntington's disease, drug induced dyskinesias, neuroleptic-induced dyskinesias, neurodegenerative cerebellar ataxias, centrally induced neuropathic pain, convulsions, epileptic convulsions, epilepsy, temporal lobe epilepsy, myoclonic epilepsy, tremor, dementia in Alzheimer's disease, dementia in Korsakoff syndrome, dementia, hereditary cerebellar ataxias, sleep disorders, movement disorders, essential tremor, muscle spasms, and spasticity;

psychological/psychiatric disorders, including generalized anxiety disorder, obsessive-compulsive disorder, panic disorder, posttraumatic stress disorder, social phobia, phobic disorders, substance-induced anxiety disorder, delusional disorder, schizoaffective disorder, schizophreniform disorder, substance-induced psychotic disorder, delirium, post-operative cognitive deficit (POCD), cognitive impairment, learning impairment, anxiety disorders, panic disorders, anxiety and panic disorders, social anxiety disorder (SAD), attention deficit hyperactivity disorder (ADHD), attention deficit syndrome (ADS), dementia, posttraumatic stress disorder (PTSD), schizophrenia, positive or cognitive or negative symptoms of schizophrenia, major depressive disorder, major depression, depression, bipolar manic-depressive disorder, sleep disorders, agoraphobia, bulimia nervosa, eating disorders, obesity, obesity-related disorders, obesity abuse, food addiction, binge eating disorders, and hyperactivity in children;

drug/alcohol abuse, including craving (e.g., for drugs of abuse), abuse, addiction, nicotine addiction, nicotine abuse, alcohol addiction, alcohol abuse, opiate addiction, opiate abuse, cocaine addiction, cocaine abuse, amphetamine addiction, and amphetamine abuse;

skin diseases, including atopic dermatitis, itching, skin lesions induced by severe itching or atopic dermatitis, systemic sclerosis, pruritic conditions, and pruritis;

diseases of the gastro-intestinal tract and metabolic diseases, including diarrhoea, hepatic encephalopathy, hypoglycaemia, gastroesophageal reflux disease (GERD), gastrointestinal dysfunction, lower esophageal sphincter (LES) disease, functional gastrointestinal disorders, dyspepsia, vomiting, urinary incontinence, and regurgitation;

diseases of the immune system, including Sjogren's syndrome, systemic lupus erythematosus, and multiple sclerosis (MS);

eye diseases, including eye injuries, eye diseases, eye disorders, glaucoma, retinopathy, and macular degeneration;

diseases of the respiratory tract, including respiratory tract infection, chronic laryngitis, asthma, reflux-related asthma, and lung disease;

migraine; autism; restless leg syndrome (RLS); Tourette syndrome; micturition disorders; neuromuscular disorder in the lower urinary tract; and drug tolerance to opioids.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the treatment of a living animal for inhibition of progression or alleviation of selected ailments or conditions, particularly ailments or conditions susceptible to treatment with a glycine B is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

The invention claimed is:

1. A compound selected from those of Formula I:

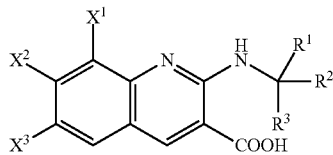

wherein
$X^1$ represents hydrogen, halogen, nitro, trifluoromethyl, $C_{1-6}$alkyl, $C_{1-6}$alkoxy, hydroxy-$C_{1-6}$alkyl, amino-$C_{1-6}$alkyl, or acylamino-$C_{1-6}$alkyl;
$X^2$ represents hydrogen, halogen, nitro, trifluoromethyl, $C_{1-6}$alkyl, $C_{1-6}$alkoxy, aryl-$C_{1-6}$alkoxy, or heteroaryl-$C_{1-6}$alkoxy;
$X^3$ represents $C_{1-6}$alkyl, halogen, nitro, or trifluoromethyl;
$R^1$ represents COOH, COOR$^4$, CONH$_2$, CONHR$^5$, CONR$^5$R$^6$, or CH$_2$OH,
$R^2$ represents hydrogen, CONH$_2$, CH$_2$OH, $C_{1-6}$alkyl, $C_{2-6}$alkenyl, $C_{2-6}$alkynyl, hydroxy-$C_{1-6}$alkyl, amino-$C_{1-6}$ alkyl, carboxy-$C_{1-6}$alkyl, $C_{1-6}$alkoxy-$C_{1-6}$alkyl, carbamoyl-$C_{1-6}$alkyl, aryl, heteroaryl, cyclo-$C_{3-12}$alkyl, cyclo-$C_{3-12}$alkyl-$C_{1-6}$alkyl, cyclo-$C_{3-12}$alkoxy-$C_{1-6}$alkyl, aryloxy-$C_{1-6}$alkyl, heteroaryloxy-$C_{1-6}$alkyl, arylsulfanyl-$C_{1-6}$alkyl, heteroarylsulfanyl-$C_{1-6}$alkyl, aryl-$C_{1-6}$alkyl, heteroaryl-$C_{1-6}$alkyl, cyclo-$C_{3-12}$alkyl-$C_{1-6}$alkyl, aryl-$C_{1-6}$alkoxy, heteroaryl-$C_{1-6}$alkoxy, aryl-$C_{1-6}$alkoxy-$C_{1-6}$alkyl, aryl-$C_{1-6}$alkylsulfanyl-$C_{1-6}$alkyl, heteroaryl-$C_{1-6}$alkoxy-$C_{1-6}$alkyl, heteroaryl-$C_{1-6}$alkylsulfanyl-$C_{1-6}$alkyl, arylamino-$C_{1-6}$alkyl, heteroarylamino-$C_{1-6}$alkyl, cyclo-$C_{3-12}$alkyl-amino-$C_{1-6}$alkyl, carboxy-$C_{1-6}$alkylamino-$C_{1-6}$alkyl, acylamino-$C_{1-6}$alkyl, arylsulfonylamino-$C_{1-6}$alkyl, $C_{1-6}$alkylsulfonylamino-$C_{1-6}$alkyl, $C_{1-6}$alkylaminocarbonyl-$C_{1-6}$alkyl, cyclo-$C_{3-12}$ alkylaminocarbonyl-$C_{1-6}$alkyl, arylaminocarbonyl-$C_{1-6}$alkyl, heteroarylaminocarbonyl-$C_{1-6}$alkyl, aryl-$C_{1-6}$alkylaminocarbonyl-$C_{1-6}$alkyl, heteroaryl-$C_{1-6}$ alkylaminocarbonyl-$C_{1-6}$alkyl, hydroxy-$C_{1-6}$alkylaminocarbonyl-$C_{1-6}$alkyl, carboxy-$C_{1-6}$alkylaminocarbonyl-$C_{1-6}$alkyl, di-($C_{1-6}$alkyl)aminocarbonyl-$C_{1-6}$ alkyl, heteroaryloxy-aryl$C_{1-6}$alkyl, aryl$C_{1-6}$alkoxy-aryl$C_{1-6}$ alkyl, heteroarylamino-aryl-$C_{1-6}$alkyl, aryl$C_{1-6}$alkyl-heteroaryl-$C_{1-6}$alkyl, or heteroarylamino-$C_{1-6}$alkyl-aryl-$C_{1-6}$alkyl;
$R^3$ represents hydrogen, $C_{1-6}$alkyl, hydroxy-$C_{1-6}$alkyl, or carboxy-$C_{1-6}$alkyl,
or $R^2$ and $R^3$ together with the carbon atom to which they are attached represent a 3, 4, 5, 6 or 7-membered ring having from 0-3 heteroatoms selected from oxygen, nitrogen, and sulfur, which ring may optionally be partially unsaturated may optionally be fused to an aryl or heteroaryl ring;
$R^4$ represents $C_{1-6}$alkyl, hydroxy-$C_{1-6}$alkyl, $C_{1-6}$alkoxy-$C_{1-6}$alkyl, di-$C_{1-6}$alkylamino-$C_{1-6}$alkyl, aryl-$C_{1-6}$alkyl, or aryloxy-$C_{1-6}$alkyl;
$R^5$ and $R^6$, which may be the same or different, each independently represent $C_{1-6}$alkyl, cyclo-$C_{3-12}$alkyl, $C_{3-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl;
or $R^5$ and $R^6$ may together represent —(CH$_2$)$_m$— with m being 3, 4, 5 or 6,
or $R^5$ and $R^6$ together with the nitrogen atom they are attached may represent a 4, 5, 6 or 7-membered ring which may be saturated or unsaturated, and wherein the ring in addition to the nitrogen atom may contain an additional heteroatom selected from sulfur, oxygen and nitrogen and may be substituted by one or more substituents selected from COOH, CONH$_2$, CONHR$^5$, $C_{1-6}$alkyl, hydroxy-$C_{1-6}$alkyl, carboxy-$C_{1-6}$alkyl, carbamoyl-$C_{1-6}$alkyl, cyclo-$C_{3-12}$alkyl, $C_{2-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl, arylamino, heteroarylamino, aryl-$C_{1-6}$alkylamino, and heteroaryl-$C_{1-6}$alkylamino;
wherein
the term "aryl" means phenyl or naphthyl, or phenyl substituted by one or more substituents selected independently from halogen, amino, hydroxy, nitro, cyano, COOH, COOR$^4$, CONH$_2$, CONHR$^5$, CONR$^5$R$^6$, CH$_2$OH, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo-$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$ alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$ alkylamino, hydroxy-$C_{1-6}$alkylamino, carboxy-$C_{1-6}$ alkylamino, $C_{1-6}$alkylamino-$C_{1-6}$alkyl, di-($C_{1-6}$alkyl) amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$ alkoxy, di-($C_{1-6}$alkyl)amino-$C_{1-6}$alkoxy, carboxy-$C_{1-6}$ alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkyl-aminosulfonyl, di-($C_{1-6}$alkyl)aminosulfonyl, arylaminosulfonyl, heteroarylaminosulfonyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$ alkylaminocarbonyl-$C_{1-6}$alkyl, carboxy-$C_{1-6}$ alkylaminocarbonyl-$C_{1-6}$alkyl, di-($C_{1-6}$alkyl)aminocarbonyl-$C_{1-6}$ alkyl, aryl$C_{2-6}$alkynyl, and heteroaryl$C_{2-6}$alkynyl;
and
the term "heteroaryl" means an aromatic 5-6 membered ring comprising one to four heteroatoms selected from oxygen, sulfur and nitrogen, or a bicyclic group containing a 5-6 membered ring comprising one to four heteroatoms selected from oxygen, sulfur and nitrogen fused with a benzene ring or with a 5-6 membered ring comprising one to four heteroatoms selected from oxygen, sulfur and nitrogen, wherein the heteroaryl is optionally substituted by one or more substituents selected independently from halogen, amino, hydroxy, nitro, cyano, COOH, COOR$^4$, CONH$_2$, CONHR$^5$, CONR$^5$R$^6$, CH2OH, trifluoromethyl, $C_{1-6}$alkyl, $C_{2-6}$alkenyl, $C_{2-6}$alkynyl, heteroaryl, $C_{1-6}$alkoxy, difluoromethoxy, trifluoromethoxy, cyclo$C_{3-12}$alkoxy, aryloxy, heteroaryloxy, aryl-$C_{1-6}$alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$alkylamino, hydroxy-$C_{1-6}$alkylamino, carboxy-$C_{1-6}$alkylamino, $C_{1-6}$alkylamino-$C_{1-6}$alkyl, di-($C_{1-6}$alkyl)amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$alkoxy, di-($C_{1-6}$alkyl)amino-$C_{1-6}$alkoxy, carboxy-$C_{1-6}$alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkylaminosulfonyl, di-($C_{1-6}$alkyl)aminosulfonyl, arylaminosulfonyl, heteroarylaminosulfonyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$alkylaminocarbonyl-$C_{1-6}$alkyl, carboxy-$C_{1-6}$ alkylaminocarbonyl-$C_{1-6}$alkyl, and di-($C_{1-6}$alkyl)aminocarbonyl-$C_{1-6}$alkyl;

and optical isomers, and pharmaceutically-acceptable acid and base addition salts thereof.

2. The compound as claimed in claim 1, wherein $R^1$ represents COOH, $CONH_2$, $CONHR^5$, or $CH_2OH$.

3. The compound as claimed in claim 1, which is selected from those of Formula IA:

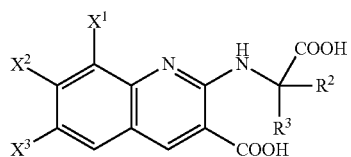

IA wherein $X^1$ represents hydrogen, halogen, nitro, trifluoromethyl, $C_{1-6}$alkyl, $C_{1-6}$alkoxy, hydroxy-$C_{1-6}$alkyl, $C_{1-6}$alkoxy-$C_{1-6}$alkyl, amino-$C_{1-6}$alkyl, or acylamino-$C_{1-6}$alkyl;

$X^2$ represents hydrogen, halogen, nitro, trifluoromethyl, $C_{1-6}$alkoxy, aryl-$C_{1-6}$alkoxy, or heteroaryl-$C_{1-6}$alkoxy;

$X^3$ represents $C_{1-6}$alkyl, halogen, nitro, or trifluoromethyl;

$R^2$ represents hydrogen, $CONH_2$, $CH_2OH$, $C_{1-6}$alkyl, $C_{2-6}$alkenyl, $C_{2-6}$alkynyl, hydroxy-$C_{1-6}$alkyl, carboxy-$C_{1-6}$alkyl, $C_{1-6}$alkoxy-$C_{1-6}$alkyl, carbamoyl-$C_{1-6}$alkyl, aryl, heteroaryl, cyclo-$C_{3-12}$alkyl, cyclo-$C_{3-12}$alkyl-$C_{1-6}$alkyl, cyclo-$C_{3-12}$alkoxy-$C_{1-6}$alkyl, aryloxy-$C_{1-6}$alkyl, heteroaryloxy-$C_{1-6}$alkyl, arylsulfanyl-$C_{1-6}$alkyl, heteroarylsulfanyl-$C_{1-6}$alkyl, aryl-$C_{1-6}$alkyl, heteroaryl-$C_{1-6}$alkyl, cyclo-$C_{3-12}$alkyl-$C_{1-6}$alkyl, aryl-$C_{1-6}$alkoxy, heteroaryl-$C_{1-6}$alkoxy, aryl-$C_{1-6}$alkoxy-$C_{1-6}$alkyl, aryl-$C_{1-6}$alkylsulfanyl-$C_{1-6}$alkyl, heteroaryl-$C_{1-6}$alkoxy-$C_{1-6}$ alkyl, heteroaryl-$C_{1-6}$alkylsulfanyl-$C_{1-6}$alkyl, arylamino-$C_{1-6}$alkyl, heteroarylamino-$C_{1-6}$alkyl, cyclo-$C_{3-12}$alkyl-amino-$C_{1-6}$alkyl, carboxy-$C_{1-6}$alkylamino-$C_{1-6}$alkyl, acylamino-$C_{1-6}$alkyl, arylsulfonylamino-$C_{1-6}$ alkyl, $C_{1-6}$alkylsulfonylamino-$C_{1-6}$alkyl, $C_{1-6}$alkylaminocarbonyl-$C_{1-6}$alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, aryl-$C_{1-6}$alkylaminocarbonyl-$C_{1-6}$alkyl, heteroaryl-$C_{1-6}$ alkylaminocarbonyl-$C_{1-6}$alkyl, hydroxy-$C_{1-6}$alkylaminocarbonyl-$C_{1-6}$alkyl, carboxy-$C_{1-6}$alkylaminocarbonyl-$C_{1-6}$alkyl, di-($C_{1-6}$alkyl)aminocarbonyl-$C_{1-6}$ alkyl, heteroaryloxy-aryl$C_{1-6}$alkyl, aryl$C_{1-6}$alkoxy-aryl$C_{1-6}$ alkyl, heteroarylamino-aryl-$C_{1-6}$alkyl, aryl$C_{1-6}$alkyl-heteroaryl-$C_{1-6}$alkyl, or heteroarylamino-$C_{1-6}$alkyl-aryl-$C_{1-6}$alkyl;

$R^3$ represents hydrogen, $C_{1-6}$alkyl, hydroxy-$C_{1-6}$alkyl, or carboxy-$C_{1-6}$alkyl, or $R^2$ and $R^3$ together with the carbon atom to which they are attached represent a 3, 4, 5, 6 or 7-membered ring having from 0-3 heteroatoms selected from oxygen, nitrogen, and sulfur, which ring may optionally be partially unsaturated may optionally be fused to an aryl or heteroaryl ring;

$R^4$ represents $C_{1-6}$alkyl, hydroxy-$C_{1-6}$alkyl, $C_{1-6}$alkoxy-$C_{1-6}$alkyl, di-$C_{1-6}$alkylamino-$C_{1-6}$alkyl, aryl-$C_{1-6}$alkyl, or aryloxy-$C_{1-6}$alkyl;

$R^5$ and $R^6$, which may be the same or different, each independently represent $C_{1-6}$alkyl, cyclo-$C_{3-12}$alkyl, $C_{3-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl;

or $R^5$ and $R^6$ may together represent —$(CH_2)_m$— with m being 3, 4, 5 or 6, or $R^5$ and $R^6$ together with the nitrogen atom they are attached may represent a 4, 5, 6 or 7-membered ring which may be saturated or unsaturated, and wherein the ring in addition to the nitrogen atom may contain an additional heteroatom selected from sulfur, oxygen and nitrogen and may be substituted by one or more substituents selected from COOH, $CONH_2$, $CONHR^5$, hydroxy-$C_{1-6}$alkyl, carboxy-$C_{1-6}$alkyl, carbamoyl-$C_{1-6}$ alkyl, cyclo-$C_{3-12}$alkyl, $C_{2-6}$alkenyl, cyclo-$C_{3-12}$alkyl-$C_{1-6}$alkyl, aryl, heteroaryl, aryl-$C_{1-6}$alkyl, or heteroaryl-$C_{1-6}$alkyl, arylamino, heteroarylamino, aryl-$C_{1-6}$ alkylamino, and heteroaryl-$C_{1-6}$alkylamino;

wherein the term "aryl" means phenyl or naphthyl, or phenyl substituted by one or more substituents selected independently from halogen, amino, hydroxy, nitro, cyano, COOH, $COOR^4$, $CONH_2$, $CONHR^5$, $CONR^5R^6$, $CH_2OH$, trifluoromethyl, $C_{2-6}$alkenyl, $C_{2-6}$alkynyl, heteroaryl, $C_{1-6}$alkoxy, difluoromethoxy, trifluoromethoxy, cyclo-$C_{3-12}$alkoxy, aryloxy, heteroaryloxy, aryl-$C_{1-6}$ alkoxy, heteroaryl-$C_{1-6}$alkoxy, hydroxy-$C_{1-6}$alkyl, carboxy-$C_{1-6}$alkyl, carbamoyl-$C_{1-6}$alkyl, carboxy-$C_{2-6}$alkenyl, carboxy-$C_{2-6}$alkynyl, $C_{1-6}$alkoxy-$C_{1-6}$alkyl, hydroxy-$C_{1-6}$alkoxy, $C_{1-6}$alkoxy-$C_{1-6}$alkoxy, carboxy-$C_{1-6}$alkoxy, carbo-$C_{1-6}$alkoxy, $C_{1-6}$alkylamino, cyclo-$C_{3-12}$alkylamino, arylamino, heteroarylamino, aryl-$C_{1-6}$alkylamino, heteroaryl-$C_{1-6}$alkylamino, hydroxy-$C_{1-6}$alkylamino, carboxy-$C_{1-6}$alkylamino, $C_{1-6}$alkylamino-$C_{1-6}$alkyl, di-($C_{1-6}$alkyl)amino, acylamino, di-($C_{1-6}$alkyl)amino-$C_{1-6}$alkyl, carboxy-$C_{1-6}$alkylamino-$C_{1-6}$alkyl, $C_{1-6}$alkylamino-$C_{1-6}$alkoxy, di-($C_{1-6}$alkyl)amino-$C_{1-6}$alkoxy, carboxy-$C_{1-6}$alkylamino-$C_{1-6}$alkoxy, $C_{1-6}$alkylsulfonylamino, arylsulfonylamino, $C_{1-6}$alkylsulfonylamino-$C_{1-6}$alkyl, $C_{1-6}$alkyl-aminosulfonyl, di-($C_{1-6}$alkyl)aminosulfonyl, arylaminosulfonyl, heteroarylaminosulfonyl, $C_{1-6}$alkylaminocarbonyl-$C_{1-6}$ alkyl, cyclo-$C_{3-12}$alkylaminocarbonyl-$C_{1-6}$alkyl, arylaminocarbonyl-$C_{1-6}$alkyl, heteroarylaminocarbonyl-$C_{1-6}$alkyl, hydroxy-$C_{1-6}$alkylaminocarbonyl-$C_{1-6}$ alkyl, carboxy-$C_{1-6}$alkylaminocarbonyl-$C_{1-6}$alkyl, di-($C_{1-6}$alkyl)aminocarbonyl-$C_{1-6}$alkyl, aryl$C_{2-6}$alkynyl, and heteroaryl$C_{2-6}$alkynyl;

and the term "heteroaryl" means an aromatic 5-6 membered ring comprising one to four heteroatoms selected from oxygen, sulfur and nitrogen, or a bicyclic group containing a 5-6 membered ring comprising one to four heteroatoms selected from oxygen, sulfur and nitrogen fused with a benzene ring or with a 5-6 membered ring comprising one to four heteroatoms selected from oxygen, sulfur and nitrogen, wherein the heteroaryl is optionally substituted by one or more substituents selected independently from halogen, amino, hydroxy, nitro, cyano, COOH, COOR$^4$, CONH$_2$, CONHR$^5$, CONR$^5$R$^6$, CH2OH, trifluoromethyl, C$_{1-6}$alkyl, C$_{2-6}$alkenyl, C$_{2-6}$alkynyl, heteroaryl, C$_{1-6}$alkoxy, difluoromethoxy, trifluoromethoxy, cycloC$_{3-12}$alkoxy, aryloxy, heteroaryloxy, aryl-C$_{1-6}$alkoxy, heteroaryl-C$_{1-6}$alkoxy, hydroxy-C$_{1-6}$alkyl, carboxy-C$_{1-6}$alkyl, carbamoyl-C$_{1-6}$alkyl, carboxy-C$_{2-6}$alkenyl, carboxy-C$_{2-6}$alkynyl, C$_{1-6}$alkoxy-C$_{1-6}$alkyl, hydroxy-C$_{1-6}$alkoxy, C$_{1-6}$alkoxy-C$_{1-6}$alkoxy, carboxy-C$_{1-6}$alkoxy, carbo-C$_{1-6}$alkoxy, C$_{1-6}$alkylamino, cyclo-C$_{3-12}$alkylamino, arylamino, heteroarylamino, aryl-C$_{1-6}$alkylamino, heteroaryl-C$_{1-6}$alkylamino, hydroxy-C$_{1-6}$alkylamino, carboxy-C$_{1-6}$alkylamino, C$_{1-6}$alkylamino-C$_{1-6}$alkyl, di-(C$_{1-6}$alkyl) amino, acylamino, di-(C$_{1-6}$alkyl)amino-C$_{1-6}$alkyl, carboxy-C$_{1-6}$alkylamino-C$_{1-6}$alkyl, C$_{1-6}$alkylamino-C$_{1-6}$ alkoxy, di-(C$_{1-6}$alkyl)amino-C$_{1-6}$alkoxy, carboxy-C$_{1-6}$ alkylamino-C$_{1-6}$alkoxy, C$_{1-6}$alkylsulfonylamino, arylsulfonylamino, C$_{1-6}$alkylsulfonylamino-C$_{1-6}$alkyl, C$_{1-6}$alkylaminosulfonyl, di-(C$_{1-6}$alkyl)aminosulfonyl, arylaminosulfonyl, heteroarylaminosulfonyl, C$_{1-6}$alkylaminocarbonyl-C$_{1-6}$alkyl, cyclo-C$_{3-12}$alkylaminocarbonyl-C$_{1-6}$alkyl, arylaminocarbonyl-C$_{1-6}$alkyl, heteroarylaminocarbonyl-C$_{1-6}$alkyl, hydroxy-C$_{1-6}$ alkylaminocarbonyl-C$_{1-6}$alkyl, carboxy-C$_{1-6}$ alkylaminocarbonyl-C$_{1-6}$alkyl, and di-(C$_{1-6}$alkyl)aminocarbonyl-C$_{1-6}$alkyl;
and optical isomers, and pharmaceutically-acceptable acid and base addition salts thereof.

4. The compound as claimed in claim 1, wherein
R$^2$ represents hydrogen, CH$_2$OH, C$_{1-6}$alkyl, hydroxy-C$_{1-6}$ alkyl, amino-C$_{1-6}$alkyl, carboxy-C$_{1-6}$alkyl, carbamoyl-C$_{1-6}$alkyl, aryl, aryl-C$_{1-6}$alkyl, heteroaryl-C$_{1-6}$alkyl, cyclo-C$_{3-12}$alkyl-C$_{1-6}$alkyl, aryl-C$_{1-6}$alkoxy-C$_{1-6}$alkyl, heteroarylamino-C$_{1-6}$alkyl, acylamino-C$_{1-6}$alkyl, arylaminocarbonyl-C$_{1-6}$alkyl, aryl-C$_{1-6}$alkylaminocarbonyl-C$_{1-6}$alkyl, heteroaryloxy-arylC$_{1-6}$alkyl, arylC$_{1-6}$ alkoxy-aryl-C$_{1-6}$alkyl, heteroarylamino-aryl-C$_{1-6}$ alkyl, aryl-C$_{1-6}$alkyl-heteroaryl-C$_{1-6}$alkyl, or heteroarylamino-C$_{1-6}$alkyl-aryl-C$_{1-6}$alkyl; and
R$^3$ represents hydrogen or R$^2$ and R$^3$ together with the carbon atom to which they are attached form a 3, 4, 5, 6, or 7-membered ring which is optionally fused to an aryl ring.

5. The compound as claimed in claim 4, wherein
R$^2$ represents aryl-C$_{1-6}$alkyl, heteroaryl-C$_{1-6}$alkyl, cyclo-C$_{3-12}$alkyl-C$_{1-6}$alkyl, heteroarylamino-C$_{1-6}$alkyl, heteroaryloxy-arylC$_{1-6}$alkyl, aryl-C$_{1-6}$alkoxy-C$_{1-6}$alkyl, or arylC$_{1-6}$alkoxy-aryl-C$_{1-6}$alkyl; and
R$^3$ represents hydrogen.

6. The compound as claimed in claim 1, wherein
X$^1$ and X$^2$ each independently represent hydrogen, halogen, CF$_3$, or C$_{1-6}$alkyl, and X$^3$ represents halogen, CF$_3$, or C$_{1-6}$alkyl.

7. The compound as claimed in claim 6, wherein
X$^1$ and X$^2$ each independently represent hydrogen, halogen, CF$_3$ or methyl, and X$^3$ represents halogen, CF$_3$ or methyl.

8. The compound as claimed in claim 7, wherein
X$^1$ and X$^2$ each independently represent hydrogen, halogen or methyl, and X$^3$ represents halogen.

9. The compound as claimed in claim 8, wherein
X$^1$ and X$^2$ each independently represent hydrogen, chlorine, bromine or methyl, and X$^3$ represents chlorine or bromine.

10. The compound as claimed in claim 6, wherein
R$^2$ represents C$_{1-6}$alkyl and R$^3$ represents hydrogen.

11. The compound as claimed in claim 1, which is selected from:
- 2-((S)-1-Carboxy-2-phenyl-ethylamino)-6-chloro-quinoline-3-carboxylic acid,
- 2-[1-Carboxy-2-(1H-indol-3-yl)-ethylamino]-6-chloro-quinoline-3-carboxylic acid,
- 2-(1-Carboxy-butylamino)-6-chloro-quinoline-3-carboxylic acid,
- 2-(Carboxymethyl-amino)-6-chloro-quinoline-3-carboxylic acid,
- 2-[(Carboxy-phenyl-methyl)-amino]-6-chloro-quinoline-3-carboxylic acid,
- 2-((R)-1-Carboxy-2-phenyl-ethylamino)-6-chloro-quinoline-3-carboxylic acid,
- 6-Chloro-2-((R)-2-hydroxy-1-phenylethylamino)-quinoline-3-carboxylic acid,
- 2-{(S)-1-Carboxy-2-[4-(3-carboxy-6-chloroquinolin-2-yloxy)-phenyl]-ethylamino}-6-chloro-quinoline-3-carboxylic acid,
- 2-[(S)-1-Carboxy-2-(4-nitro-phenyl)-ethylamino]-6-chloro-quinoline-3-carboxylic acid,
- 6-Chloro-2-((R)-1-hydroxymethyl-2-phenyl-ethylamino)-quinoline-3-carboxylic acid,
- 6-Chloro-2-((S)-2-hydroxy-1-phenyl-ethylamino)-quinoline-3-carboxylic acid,
- 2-[(R)-1-Carboxy-2-(1H-indol-3-yl)-ethylamino]-6-chloro-quinoline-3-carboxylic acid,
- 6-Chloro-2-((S)-1-hydroxymethyl-2-phenyl-ethylamino)-quinoline-3-carboxylic acid,
- 6-Chloro-2-[(S)-1-hydroxymethyl-2-(1H-indol-3-yl)-ethylamino]-quinoline-3-carboxylic acid,
- 2-[(S)-1-Carboxy-2-(1-methyl-1H-indol-3-yl)-ethylamino]-6-chloro-quinoline-3-carboxylic acid,
- 2-((S)-5-Benzyloxycarbonylamino-1-carboxy-pentylamino)-6-chloro-quinoline-3-carboxylic acid,
- 2-[(S)-1-Carboxy-2-(4-methoxy-phenyl)-ethylamino]-6-chloro-quinoline-3-carboxylic acid,
- 2-[1-Carboxy-2-(5-methoxy-1H-indol-3-yl)-ethylamino]-6-chloro-quinoline-3-carboxylic acid,
- 2-((R)-2-Benzyloxy-1-carboxy-ethylamino)-6-chloro-quinoline-3-carboxylic acid,
- 2-[(R)-1-Carboxy-2-(1-methyl-1H-indol-3-yl)-ethylamino]-6-chloro-quinoline-3-carboxylic acid,
- 2-[1-Carboxy-2-(5-methyl-1H-indol-3-yl)-ethylamino]-6-chloro-quinoline-3-carboxylic acid,
- 2-[(S)-2-(4-Benzyloxy-phenyl)-1-carboxy-ethylamino]-6-chloro-quinoline-3-carboxylic acid,
- 2-[(S)-1-Carboxy-2-(4-chloro-phenyl)-ethylamino]-6-chloro-quinoline-3-carboxylic acid,
- 2-(1-Carboxy-indan-1-ylamino)-6-chloro-quinoline-3-carboxylic acid,
- 2-[1-Carboxy-2-(5-fluoro-1H-indol-3-yl)-ethylamino]-6-chloro-quinoline-3-carboxylic acid,
- 2-(1-Carboxy-ethylamino)-6-chloro-quinoline-3-carboxylic acid,
- 2-((S)-5-Amino-1-carboxy-pentylamino)-6-chloro-quinoline-3-carboxylic acid,
- 2-(1-Carboxy-3-phenyl-propylamino)-6-chloro-quinoline-3-carboxylic acid,
- 2-[1-Carboxy-2-(1H-imidazol-4-yl)-ethylamino]-quinoline-3-carboxylic acid, erythro-2-(1-Carboxy-2-phenyl-propylamino)-6-chloro-quinoline-3-carboxylic acid,
threo-2-(1-Carboxy-2-phenyl-propylamino)-6-chloro-quinoline-3-carboxylic acid,
2-((S)-1-Carboxy-2-phenyl-ethylamino)-6,7-dichloro-quinoline-3-carboxylic acid,
2-[1-Carboxy-2-(6-fluoro-1H-indol-3-yl)-ethylamino]-6-chloro-quinoline-3-carboxylic acid,
2-[(S)-1-Carboxy-2-(4-hydroxy-phenyl)-ethylamino]-6-chloro-quinoline-3-carboxylic acid,
2-((S)-1-Carboxy-2-cyclohexyl-ethylamino)-6-chloro-quinoline-3-carboxylic acid,
2-[(R)-1-Carboxy-2-(1H-indol-3-yl)-ethylamino]-6,7-dichloro-quinoline-3-carboxylic acid,
2-[(S)-1-Carboxy-2-(3,4-dihydroxy-phenyl)-ethylamino]-6-chloro-quinoline-3-carboxylic acid,
2-[1-Carboxy-2-(3-carboxy-6-chloro-quinolin-2-ylamino)-ethylamino]-6-chloro-quinoline-3-carboxylic acid,
2-[1-Carboxy-2-(4-fluoro-phenyl)-ethylamino]-6-chloro-quinoline-3-carboxylic acid,
2-[1-Carboxy-2-(2-fluoro-phenyl)-ethylamino]-6-chloro-quinoline-3-carboxylic acid,
2-[(S)-1-Carboxy-2-(4-hydroxy-3-nitro-phenyl)-ethylamino]-6-chloro-quinoline-3-carboxylic acid,
2-((S)-1-Carboxy-2-phenyl-ethylamino)-6,8-dichloro-quinoline-3-carboxylic acid,
6-Chloro-2-[1-(naphthalen-2-ylcarbamoyl)-ethylamino]-quinoline-3-carboxylic acid,
2-((R)-1-Carboxy-2-phenyl-ethylamino)-quinoline-3-carboxylic acid,
2-[(R)-1-Carboxy-2-(1H-indol-3-yl)-ethylamino]-quinoline-3-carboxylic acid,
2-[1-(1-Carbamoyl-2-phenyl-ethylcarbamoyl)-2-phenyl-ethylamino]-6-chloro-quinoline-3-carboxylic acid,
6-Bromo-2-((R)-1-carboxy-2-phenyl-ethylamino)-quinoline-3-carboxylic acid,
2-{(S)-2-[3-Amino-4-(3-carboxy-6-chloro-quinolin-2-yloxy)-phenyl]-1-carboxy-ethylamino}-6-chloro-quinoline-3-carboxylic acid,
2-[(S)-2-(3-Amino-4-hydroxy-phenyl)-1-carboxy-ethylamino]-6-chloro-quinoline-3-carboxylic acid,
2-[(S)-1-Carboxy-4-(6-chloro-3-carboxy-quinolin-2-ylamino)-butylamino]-6-chloro-quinoline-3-carboxylic acid,
2-[(S)-1-Carboxy-2-(3-chloro-4-hydroxy-phenyl)-ethylamino]-6-chloro-quinoline-3-carboxylic acid,
2-[1-Carboxy-2-(3-fluoro-4-hydroxy-phenyl)-ethylamino]-6-chloro-quinoline-3-carboxylic acid,
2-[1-Carboxy-2-(4-carboxy-phenyl)-ethylamino]-6-chloro-quinoline-3-carboxylic acid,
2-[1-[1-Carboxy-2-(4-carboxy-phenyl)-ethylcarbamoyl]-2-(4-carboxy-phenyl)-ethylamino]-6-chloro-quinoline-3-carboxylic acid,
2-((S)-1-Carboxy-2-pyridin-4-yl-ethylamino)-6-chloro-quinoline-3-carboxylic acid,
6,8-Dibromo-2-(1-carboxy-2-phenyl-ethylamino)-quinoline-3-carboxylic acid,
2-[1-Carboxy-2-(3,5-dimethyl-pyrazol-1-yl)-ethylamino]-6-chloro-quinoline-3-carboxylic acid,
2-[2-(4-Amino-phenyl)-1-carboxy-ethylamino]-6-chloro-quinoline-3-carboxylic acid,
2-{1-Carboxy-2-[4-(3-carboxy-6-chloro-quinolin-2-ylamino)-phenyl]-ethylamino}-6-chloro-quinoline-3-carboxylic acid,
2-[1-[1-Carboxy-2-(3-carboxy-phenyl)-ethylcarbamoyl]-2-(3-carboxy-phenyl)-ethylamino]-6-chloro-quinoline-3-carboxylic acid,
2-[1-Carboxy-2-(3-methoxy-phenyl)-ethylamino]-6-chloro-quinoline-3-carboxylic acid,
2-[1-Carboxy-2-(4-phenylethynyl-phenyl)-ethylamino]-6-chloro-quinoline-3-carboxylic acid,
2-[1-Carboxy-2-(3-hydroxy-phenyl)-ethylamino]-6-chloro-quinoline-3-carboxylic acid,
2-[1-Carboxy-2-(3-hydroxy-phenyl)-ethylamino]-6,8-dichloro-quinoline-3-carboxylic acid,
2-[1-Carboxy-2-(2-methyl-benzooxazol-5-yl)-ethylamino]-6-chloro-quinoline-3-carboxylic acid,
2-[1-Carboxy-2-(phenylcarbamoyl-ethylamino)]-6-chloro-quinoline-3-carboxylic acid,
2-[1-Carboxy-2-(1H-indol-3-yl)-ethylamino]-6,8-dichloro-quinoline-3-carboxylic acid,
2-[1-Carboxy-2-(2-chloro-5-methoxy-phenyl)-ethylamino]-6-chloro-quinoline-3-carboxylic acid,
6-Chloro-2-[2-hydroxy-1-(3-methoxy-phenylcarbamoyl)-ethylamino]-quinoline-3-carboxylic acid,
6-Chloro-2-(phenylcarbamoyl-methyl-amino)-quinoline-3-carboxylic acid,
6,8-Dichloro-2-(phenylcarbamoyl-methyl-amino)-quinoline-3-carboxylic acid,
2-[1-Carboxy-2-(2-methoxy-phenyl)-ethylamino]-6-chloro-quinoline-3-carboxylic acid,
2-(2-Carbamoyl-1-carboxy-ethylamino)-6-chloro-quinoline-3-carboxylic acid,
2-[1-Carboxy-2-(1-phenyl-ethylcarbamoyl)-ethylamino]-6-chloro-quinoline-3-carboxylic acid,
2-(2-Carboxy-1-phenylcarbamoyl-ethylamino)-6-chloro-quinoline-3-carboxylic acid,
6-Chloro-2-(2-hydroxy-1-phenylcarbamoyl-ethylamino)-quinoline-3-carboxylic acid,
2-(3-Carbamoyl-1-carboxy-propylamino)-6-chloro-quinoline-3-carboxylic acid,
2-{1-Carboxy-2-[1-(3-methyl-4-nitro-benzyl)-1H-imidazol-4-yl]-ethylamino}-6-chloro-quinoline-3-carboxylic acid,
2-(3-Carboxy-6-chloro-quinolin-2-ylamino)-3-phenyl-succinic acid,
2-{4-[2-(3-carboxy-6-chloro-quinolin-2-yl)amino-2-carboxy-ethyl]phenyl]-1-carboxy-ethylamino}-6-chloro-quinoline-3-carboxylic acid,
2-{2-[3-(3-carboxy-6-chloro-quinolin-2-yloxy)-phenyl]-1-carboxy-ethylamino}-6-chloro-quinoline-3-carboxylic
2-{2-[3-[2-(3-carboxy-6-chloro-quinolin-2-yl)amino-2-carboxy-ethyl]-phenyl]-1-carboxy-ethylamino}-6-chloro-quinoline-3-carboxylic acid,
2-(1-Carboxy-2-thiophen-2-yl-ethylamino)-6-chloro-quinoline-3-carboxylic acid,
2-(1-Carbamoyl-2-phenyl-ethylamino)-6-chloro-quinoline-3-carboxylic acid,
6-Chloro-2-(1-methylcarbamoyl-2-phenyl-ethylamino)-quinoline-3-carboxylic acid,
6,8-Dichloro-2-(1-methylcarbamoyl-2-phenyl-ethylamino)-quinoline-3-carboxylic acid,
2-(2-Benzoylamino-1-carboxy-ethylamino)-6-chloro-quinoline-3-carboxylic acid,
6,8-Dichloro-2-(2-hydroxy-1-phenylcarbamoyl-ethylamino)-quinoline-3-carboxylic acid,
2-(1-Carboxy-2-phenylacetylamino-ethylamino)-6-chloro-quinoline-3-carboxylic acid, 2-[1-[1-Carboxy-2-(2-methoxy-phenyl)-ethylcarbamoyl]-2-(2-methoxy-phenyl)-ethylamino]-6-chloro-quinoline-3-carboxylic acid,
2-[1-[1-Carboxy-2-(2-chloro-5-methoxy-phenyl)-ethylcarbamoyl]-2-(2-chloro-5-methoxy-phenyl)-ethylamino]-6-chloro-quinoline-3-carboxylic acid,
2-[(1-Carboxy-2-thiophen-2-yl-ethylcarbamoyl)-2-thiophen-2-yl-ethylamino]-6-chloro-quinoline-3-carboxylic acid,
2-[1-Carboxy-2-(3-carboxy-phenyl)-ethylamino]-6-chloro-quinoline-3-carboxylic acid,
2-[1-[1-Carboxy-2-(4-phenylethynyl-phenyl)-ethylcarbamoyl]-2-(4-phenylethynyl-phenyl)-ethylamino]-6-chloro-quinoline-3-carboxylic acid,
2-(1-Carboxy-2-phenyl-ethylamino)-6-chloro-8-methylquinoline-3-carboxylic acid,
2-{1-Carboxy-2-[4-(quinolin-2-yloxy)-phenyl]-ethylamino}-6-chloro-quinoline-3-carboxylic acid,
2-[1-Carboxy-2-(1H-indol-3-yl)-ethylamino]-6-chloro-8-methylquinoline-3-carboxylic acid,
2-[1-Carboxy-2-(3-fluoro-phenyl)-ethylamino]-6-chloro-quinoline-3-carboxylic acid,
2-(1-Carboxy-2-pyridin-3-yl-ethylamino)-6-chloro-quinoline-3-carboxylic acid,
2-{(S)-1-Carboxy-2-[4-(3-carboxy-pyridin-2-yloxy)-phenyl]-ethylamino}-6-chloro-quinoline-3-carboxylic acid,
2-{(S)-2-[4-(5-Bromo-pyridin-2-yloxy)-phenyl]-1-carboxy-ethylamino}-6-chloro-quinoline-3-carboxylic acid,
6-Bromo-2-[1-carboxy-2-(4-hydroxy-phenyl)-ethylamino]-quinoline-3-carboxylic acid,
6-Bromo-2-{1-carboxy-2-[4-(3-carboxy-quinolin-2-yloxy)-phenyl]-ethylamino}-quinoline-3-carboxylic acid,
2-{1-Carboxy-2-[4-(quinolin-4-ylamino)-phenyl]-ethylamino}-6-chloro-quinoline-3-carboxylic acid,
2-{1-Carboxy-2-[4-(3-carboxy-pyridin-2-ylamino)-phenyl]-ethylamino}-6-chloro-quinoline-3-carboxylic acid,
2-{1-Carboxy-2-[4-(7-chloro-quinolin-4-ylamino)-phenyl]-ethylamino}-6-chloro-quinoline-3-carboxylic acid,
2-{1-Carboxy-2-[3-(3-carboxy-6-bromo-quinolin-2-yloxy)-phenyl]-ethylamino}-6-bromo-quinoline-3-carboxylic acid,
2-{1-Carboxy-2-[4-(quinolin-2-ylamino)-phenyl]-ethylamino}-6-chloro-quinoline-3-carboxylic acid,
2-{(S)-1-Carboxy-2-[4-(quinolin-4-yloxy)-phenyl]-ethylamino}-6-chloro-quinoline-3-carboxylic acid,
2-{1-Carboxy-2-[4-(3-carboxy-quinolin-2-yloxy)-phenyl]-ethylamino}-6-chloro-quinoline-3-carboxylic acid,
6-Bromo-2-{2-[4-(5-bromo-pyridin-2-yloxy)-phenyl]-1-carboxy-ethylamino}-quinoline-carboxylic acid,
6-Bromo-2-{1-carboxy-2-[4-(quinolin-2-yloxy)-phenyl]-ethylamino}-quinoline-3-carboxylic acid,
2-[2-(4-Bromo-phenyl)-1-carboxy-ethylamino]-6-chloro-quinoline-3-carboxylic acid,
(S)-2-(3-Carboxy-6-chloro-quinolin-2-ylamino)-succinic acid ammonia hydrate, 2-[1-Carboxy-2-(3-fluoro-phenyl)-ethylamino]-6,8-dichloro-quinoline-3-carboxylic acid,
2-(3-Carboxy-6,8-dichloro-quinolin-2-ylamino)-3-phenyl-succinic acid,
2-(2-Benzyloxy-1-phenylcarbamoyl-ethylamino)-6-chloro-quinoline-3-carboxylic acid,
2-[(S)-1-Carboxy-2-(4-hydroxy-phenyl)-ethylamino]-6,8-dichloro-quinoline-3-carboxylic acid,
2-(3-Carboxy-6-chloro-quinolin-2-ylamino)-3-(3-fluoro-phenyl)-succinic acid,
2-((S)-1-Carboxy-2-phenyl-ethylamino)-6,8-dimethyl-quinoline-3-carboxylic acid,
2-(2-Benzylcarbamoyl-1-carboxy-ethylamino)-6-chloro-quinoline-3-carboxylic acid,
2-{(S)-1-Carboxy-2-[4-(3-carboxy-6,8-dichloro-quinolin-2-yloxy)-phenyl]-ethylamino}-6,8-dichloro-quinoline-3-carboxylic acid,
2-[(S)-1-Carboxy-2-(1-methyl-1H-indol-3-yl)-ethylamino]-6,8-dichloro-quinoline-3-carboxylic acid,
2-{(S)-1-Carboxy-2-[4-(6-chloro-qunolin-2-yloxy)-phenyl]-ethylamino}6-chloro-quinoline-3-carboxylic acid,
2-{(S)-1-Carboxy-2-[4-(8-chloro-quinolin-2-yloxy)-phenyl]-ethylamino}6-chloro-quinoline-3-carboxylic acid,
2-{(S)-1-Carboxy-2-[4-(3-chloro-pyridin-2-yloxy)-phenyl]-ethylamino}-6-chloro-quinoline-3-carboxylic acid,
2-{(S)-1-Carboxy-2-[4-(5-trifluoromethyl-pyridin-2-yloxy)-phenyl]-ethylamino}-6-chloro-quinoline-3-carboxylic acid,
2-{(S)-1-Carboxy-2-[4-(5-chloro-pyridin-2-yloxy)-phenyl]-ethylamino}-6-chloro-quinoline-3-carboxylic acid,
2-{(S)-1-Carboxy-2-[4-(3-trifluoromethyl-pyridin-2-yloxy)-phenyl]-ethylamino}-6-chloro-quinoline-3-carboxylic acid,
2-{(S)-1-Carboxy-2-[4-(5-phenyl-[1,6]naphthyridin-2-yloxy)-phenyl]-ethylamino}-6-chloro-quinoline-3-carboxylic acid,
2-{1-Carboxy-2-[4-(5-iodo-pyridin-2-yloxy)-phenyl]-ethylamino}-6-chloro-quinoline-3-carboxylic acid,
6-Chloro-2-[(S)-1-(2-methoxy-ethoxycarbonyl)-2-phenyl-ethylamino]-quinoline-3-carboxylic acid,
2-{(S)-1-Carboxy-2-[4-(5-methyl-pyridin-2-yloxy)-phenyl]-ethylamino}-6-chloro-quinoline-3-carboxylic acid,
2-{(S)-1-Carboxy-2-[4-(4-methyl-pyridin-2-yloxy)-phenyl]-ethylamino}-6-chloro-quinoline-3-carboxylic acid,
2-{(S)-1-Carboxy-2-[4-(3-methyl-pyridin-2-yloxy)-phenyl]-ethylamino}-6-chloro-quinoline-3-carboxylic acid,
2-(3-Carboxy-6-chloro-quinolin-2-ylamino)-3-(3,5-difluoro-phenyl)-succinic acid,
6-Chloro-2-[1-(2-dimethylamino-ethoxycarbonyl)-2-pyridin-2-yl-ethylamino]-quinoline-3-carboxylic acid,
6-Chloro-2-(1-ethoxycarbonyl-2-pyridin-2-yl-ethylamino)-quinoline-3-carboxylic acid,
2-{(S)-2-[4-(3-Bromo-pyridin-2-yloxy)-phenyl]-1-carboxy-ethylamino}-6-chloro-quinoline-3-carboxylic acid,
2-{(S)-1-Carboxy-2-[4-(3,5-dichloro-pyridin-2-yloxy)-phenyl]-ethylamino}-6-chloro-quinoline-3-carboxylic acid,
2-{(S)-2-[4-(5-Amino-pyridin-2-yloxy)-phenyl]-1-carboxy-ethylamino}-6-chloro-quinoline-3-carboxylic acid,
2-{(S)-1-Carboxy-2-[4-(7-chloro-quinolin-4-yloxy)-phenyl]-ethylamino}-6-chloro-quinoline-3-carboxylic acid,
2-{(S)-1-Carboxy-2-[4-(5-chloro-3-fluoro-pyridin-2-yloxy)-phenyl]-ethylamino}-6-chloro-quinoline-3-carboxylic acid, 2-{(S)-2-[4-(3-Bromo-pyridin-4-yloxy)-phenyl]-1-carboxy-ethylamino}-6-chloro-quinoline-3-carboxylic acid,
2-{(S)-2-[4-(7-Bromo-isoquinolin-1-yloxy)-phenyl]-1-carboxy-ethylamino}-6-chloro-quinoline-3-carboxylic acid,
2-{(S)-1-Carboxy-2-[4-(2-chloro-pyridin-4-yloxy)-phenyl]-ethylamino}-6-chloro-quinoline-3-carboxylic acid,
2-{(S)-2-[4-(6-Bromo-[1,8]naphthyridin-4-yloxy)-phenyl]-1-carboxy-ethylamino}-6-chloro-quinoline-3-carboxylic acid,
2-{(S)-1-Carboxy-2-[4-(6-methyl-pyridin-2-yloxy)-phenyl]-ethylamino}-6-chloro-quinoline-3-carboxylic acid,
2-(1-Carboxy-2-pyridin-2-yl-ethylamino)-6-chloro-quinoline-3-carboxylic acid,
6-Chloro-2-((S)-2-phenyl-1-propylcarbamoyl-ethylamino)-quinoline-3-carboxylic acid,
6-Chloro-2-((S)-2-phenyl-1-phenylcarbamoyl-ethylamino)-quinoline-3-carboxylic acid,
2-((S)-1-Carboxy-2-hydroxy-ethylamino)-6-chloro-quinoline-3-carboxylic acid,
6-Chloro-2-[(S)-1-(2-hydroxy-ethylcarbamoyl)-2-phenyl-ethylamino]-quinoline-3-carboxylic acid,
6-Chloro-2-[(S)-2-phenyl-1-(1H-tetrazol-5-ylcarbamoyl)-ethylamino]-quinoline-3-carboxylic acid,
2-[(S)-1-Carboxy-2-(1H-indol-3-yl)-ethylamino]-6,8-dichloro-quinoline-3-carboxylic acid,
2-((S)-1-Carboxy-2-thiophen-2-yl-ethylamino)-6-chloro-quinoline-3-carboxylic acid, and
optical isomers, and pharmaceutically-acceptable acid and base addition salts thereof.

12. A pharmaceutical composition comprising as active ingredient a compound as claimed in claim 1, optionally together with one or more pharmaceutically acceptable excipients.

* * * * *

UNITED STATES PATENT AND TRADEMARK OFFICE
CERTIFICATE OF CORRECTION

PATENT NO.       : 8,288,549 B2
APPLICATION NO.  : 12/998246
DATED            : October 16, 2012
INVENTOR(S)      : Markus Henrich et al.

Page 1 of 1

It is certified that error appears in the above-identified patent and that said Letters Patent is hereby corrected as shown below:

Column 107, Line 26: "$C_{1-6}$alkoxy, hydroxy-$C_{1-6}$alkyl, amino-$C_{1}$-" Should Be
-- $C_{1-6}$alkoxy, hydroxy-$C_{1-6}$alkyl, $\underline{C_{1-6}\text{alkoxy-}C_{1-6}\text{alkyl,}}$ amino-$C_{1}$- --

Column 109, Line 43: "$X^2$ represents hydrogen, halogen, nitro, trifluoromethyl," Should Be
-- $X^2$ represents hydrogen, halogen, nitro, trifluoromethyl, $\underline{C_{1-6}\text{alkyl,}}$ --

Column 109, Line 47: "$C_{2-6}$alkenyl, $C_{2-6}$alkynyl, hydroxy-$C_{1-6}$alkyl, carboxy" Should Be
-- $C_{2-6}$alkenyl, $C_{2-6}$alkynyl, hydroxy-$C_{1-6}$alkyl, $\underline{\text{amino-}C_{1-6}\text{alkyl,}}$ carboxy --

Column 110, Line 28: "COOH, $CONH_2$, $CONHR^5$," Should Be
-- COOH, $CONH_2$, $CONHR^5$, $\underline{C_{1-6}\text{alkyl,}}$ --

Column 110, Line 39: "$CH_2OH$, trifluoromethyl, $C_{2-6}$alkenyl, $C_{2-6}$alkynyl," Should Be
-- $CH_2OH$, trifluoromethyl, $\underline{C_{1-6}\text{alkyl,}}$ $C_{2-6}$alkenyl, $C_{2-6}$alkynyl, --

Column 114, Line 50: "lic" Should Be
-- lic $\underline{\text{acid,}}$ --

Column 115, Line 55: "ethylamino}-quinoline-carboxylic acid," Should Be
-- ethylamino}-quinoline-$\underline{3}$-carboxylic acid, --

Signed and Sealed this
Twenty-fifth Day of December, 2012

David J. Kappos
*Director of the United States Patent and Trademark Office*